US011085091B2

(12) United States Patent
Arsac et al.

(10) Patent No.: US 11,085,091 B2
(45) **Date of Patent: *Aug. 10, 2021**

(54) METHOD FOR IN VITRO DIAGNOSIS OR PROGNOSIS OF TESTICULAR CANCER

(71) Applicant: BIOMERIEUX, Marcy l'Etoile (FR)

(72) Inventors: Maud Arsac, Saint-Chamond (FR); Bertrand Bonnaud, Verin (FR); Francois Mallet, Villeurbanne (FR); Jean-Philippe Pichon, Clermont-Ferrand (FR)

(73) Assignee: BIOMERIEUX, Marcy l'Etoile (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/353,386

(22) Filed: Mar. 14, 2019

(65) Prior Publication Data

US 2019/0203306 A1 Jul. 4, 2019

Related U.S. Application Data

(63) Continuation of application No. 13/739,447, filed on Jan. 11, 2013, now Pat. No. 10,240,213, which is a continuation of application No. 13/138,000, filed on Sep. 23, 2011, now abandoned, which is a continuation of application No. 12/918,166, filed as application No. PCT/FR2009/050390 on Mar. 10, 2009, now abandoned.

(30) Foreign Application Priority Data

Mar. 12, 2008 (FR) ...................................... 0851619

(51) Int. Cl.
*C12Q 1/70* (2006.01)
*C12Q 1/6886* (2018.01)

(52) U.S. Cl.
CPC .......... *C12Q 1/702* (2013.01); *C12Q 1/6886* (2013.01); *C12Q 2600/154* (2013.01); *C12Q 2600/158* (2013.01)

(58) Field of Classification Search
CPC .......................... C12Q 1/702; C12Q 2600/158
See application file for complete search history.

(56) References Cited

U.S. PATENT DOCUMENTS 5,858,723 A 1/1999 Mueller-Lantzsch et al.
2001/0051344 A1 12/2001 Shalon et al.

OTHER PUBLICATIONS

Examiner's Table 1 (Prepared on May 19, 2017 using the online BLAST tool).
Nellaker et al. Retrovirology 2006. 3:44, 11 pages. (Year: 2006).
Yao et al. Genes, Brain and Behavior. 2008. 7(1):103-12. Epub date of Jun. 7, 2007. (Year: 2007).
Shaw et al. Am Fam Physician. 2008. 77(4):469-476. (Year: 2008).

(Continued)

*Primary Examiner* — Joseph G. Dauner
(74) *Attorney, Agent, or Firm* — Oliff PLC

(57) ABSTRACT

The invention relates to a method for in vitro diagnosis or prognosis of testicular cancer which comprises a step of detecting the presence or absence of at least one expression product from at least one nucleic acid sequence selected from the sequences identified in SEQ ID NOS: 1 to 6 or from the sequences which exhibit at least 99% identity with one of the sequences identified in SEQ ID NOS: 1 to 6, to isolated nucleic acid sequences and to the use thereof as a testicular cancer marker.

23 Claims, 9 Drawing Sheets

Specification includes a Sequence Listing.

| Locus | Chromosome | Position (*Ensembl* V39) | Locus structure |
|---|---|---|---|
| HW4TT | 4 | 41982184:41989670 | U3 R U5 gag pol U3 R U5 env |
| HW2TT | 2 | 17383689:17391462 | U3 R U5 gag pol U3 R U5 env |
| HW13TT | 13 | 68693759:68699228 | W L U3 R U5 gag pol U3 R |
| HWXTT | X | 113026618:113027400 | U3 R U5 |
| HW21TT | 21 | 27148627:27156168 | U3 R U5 gag pol U3 R U5 env |
| ERVWE1 | 7 | 91935221:91945670 | U3 R U5 gag pol env(Syncytin-1) U3 R U5 activator |

(56) References Cited

OTHER PUBLICATIONS

Kim et al. Arch Virol. 2008.153:1587-1591.
Parseval et al. Journal of Virology. 2003. 77(19):10414-10422.
Yi et al. Journal of General Virology. 2004. 85:1203-1210.
Choi. The Scientist. Dec. 21, 2006. Retrieved on Sep. 19, 2016 from the internet: http://www.the-scientist.com/?articles.view/articleNo/24630/title/-Silent--mutations-are-not-always-silent/.
Pagani et al. PNAS. 2005. 102(18):6368-6372.
Sauna et al. Cancer Res. 2007. 67(20):9609-6912.
Kimchi-Sarafty et al. Science. 2007. 315(5811):525-528.
Crowell et al. Biochem Soc Trans. 2007. 35(Pt 3):629-633.
Casau et al. J. Virol. 1999. 73(12): 9976-9983.
Flockerzi et al. BMC Genomics. 2008. 9:354.
Schon et al. Virology. 2001. 279:280-291.
Seifarth et al. Journal of Virology. 2005. 79(1):341-352.
Fossa et al. Journal of the National Cancer Institute. 2005. 97(14): 1056-1066.
Travis et al. Journal of the National Cancer Institute. 2005. 97(18): 1354-1365.
Sant et al. European Journal of Cancer. 2007.43: 585-592.
Stephenson et al. J Clin Oncol. 2005. 23: 2781-2788.
Goedert et al; "High Prevalence of Antibodies against HERV-K10 in Patients with Testicular Cancer but not with AIDS;" Cancer Epidemiology, Biomarkers & Prevention; Apr. 1999; pp. 293-296; vol. 8.
Yi et al.; "Expression and Identification of HERV-W Family in Japanese Monkeys (*Macaca fuscata*);" Zoological Science; 2004; pp. 649-659; vol. 21; Zoological Society of Japan.
Nickerson et al; "DNA sequence diversity in a 9.7-kb region of the human lipoprotein lipase gene;" Nature Genetics; Jul. 1998; pp. 233-240; vol. 19; Nature America Inc.
Cottrell; "Molecular diagnostic applications of DNA methylation technology; Clinical Biochemistry;" 2004; pp. 595-604: vol. 37; The Canadian Society of Clinical Chemists.
International Search Report dated Sep. 15, 2009 in corresponding International Application No. PCT/FR2009/050390.
Written Opinion of the International Searching Authority dated Sep. 15, 2009 in corresponding International Application No. PCT/FR2009/050390.
Genbank Accession No. AC024022.6. Available May 13, 2005.
Genbank Accession No. AC092843.4. Available Apr. 21, 2005.
Genbank Accession No. NT_024524.13. Available Feb. 29, 2008.
Genbank Accession No. AC0030141.1. Available Feb. 4, 2000.
Genbank Accession No. AP001599.1. Available Apr. 29, 2000.
Genbank Accession No. NT_007933.14. Available Feb. 29, 2008.
Pichon et al., "Multiplex Degenerate PCR Coupled with an Oligo Sorbent Array for Human Endogenous Retrovirus Expression Profiling;" Nucleic Acids Research, vol. 34, No. 6, pp. 1-10, Mar. 22, 2006.
Forsman et al., "Development of Broadly Targeted Human Endogenous Gammaretroviral pol-based Real Time PCRs Quantitation of RNA Expression in Human Tissues;" Journal of Virological Methods, vol. 129, pp. 16-30, 2005.
Whitehead et al., "Variation in Tissue-Specific Gene Expression Among Natural Populations;" Genome Biology, vol. 6, pp. R13-R13.14, 2005.
Roman-Roman et al., "Identification of Genes Regulated During Osteoblastic Differentiation by Genome-Wide Expression Analysis of Mouse Calvaria Primary Osteoblasts In Vitro;" Bone, vol. 32, pp. 474-482, 2003.
Chan et al., "Integrating Transcriptomics and Proteomics;" G&P Magazine, vol. 6, No. 3, pp. 20-26, 2006.
Hoshikawa et al., "Hypoxia Induces Different Genes in the Lungs of Rats Compared with Mice;" Physical Genomics. vol. 12, pp. 209-219, 2003.
Thisted, "What is a P-Value?;" The University of Chicago, pp. 1-6, 1998.

HW2TT Locus

Normal testicle 12 clones

Tumoral testicle 12 clones

HW13TT Locus

Normal testicle

10 clones

Tumoral testicle

10 clones

HWXTT Locus

Normal testicle 8 clones

Tumoral testicle 9 clones

ERVWE1 Locus

Normal testicle

10 clones

Tumoral testicle

10 clones

SEQUENCE LISTING

```
<160> NUMBER OF SEQ ID NOS: 62

<210> SEQ ID NO 1
<211> LENGTH: 7487
<212> TYPE: DNA
<213> ORGANISM: Homo sapiens

<400> SEQUENCE: 1

tgagaaacag gactagttag atttcctagg ccaactaaga atccctaagc ctagctggga      60

aggtgatcgc atccaccttt aaacacgggc ttgcaactta gctcacacct gaccaatcag     120

gtagtaaaga gagctcacta aaatgctaat taggcaaaaa caggaggtaa agaaatagcc     180

aatcatctat tgcctgacac cacacgggga gggacaatga ttgggatata aacccaggaa     240

ttcgagctgg caacggcaac tccctttggg tctcctctca ttgtatggga gctctgtttt     300

cactctatta aatcttgcaa ctgcacactc ttctggtctg tgtttgttat ggcttgagct     360

gagcttttgc tggctgtcca ccactgctgt ttgctgccgt cgcagacccc ttgctgactc     420

ccacccctgc ggatctggca gggtgtctgc tgcgctcctg atccagccag gcacccactg     480

ctgctcccaa tcaggctaaa ggcttgccat tgttcctgca tggctaagtg cccgggttcg     540

tgctaattga gctgaacact agtcgctggg ttccacagtt ctcttccgtg acccacagct     600

tctaatagag ctataacact cactgcatgg cccaacattc cattccttgg aatctgtgag     660

gccaagaacc cccggtcaga gaacaagaag cttgccacca tcttggaagc agcccgccac     720

cattttggga gctctaagaa caaggacccc ccagtaacat tttggtgacc acgaagggac     780

ctccaaagca gtgagtaata ttgaaccact tccgcttgct attctgtcct aaccttcctt     840

agaattggag gaaaataccg ggcacctgtc ggccagttaa gaacgattag cgtggccgcc     900

agacttaaga ctctggtgtg aggctgtctg ggaaagggct ttctaacaac ccccaaccct     960

tccgggttgg gagctttggt ctgcctggaa ccagcttcca ctttcaattt tcctggggaa    1020

tccaagggct gactagaggc agaaagctgt catcccgaac tcctggcatt agacagttga    1080

gatcgtggcg cagccagaag tctctactca acagtcaccc atgcgtgcac ccctaccttt    1140

ccttctaacc catacctccc gggtcccaac catgactttc ttgaaagtgt agcccctaaa    1200

ttctctttac ctctaaatct acttcttctc atccctgctt cctaggtact aatggttcag    1260

actttcattt cctctagcaa gttctatctc cagagggatc taaggaaggg atctatgctg    1320

tgtccttagg cccctaggct atgaacccag agagtcttct ccctgttatc tctccccatt    1380

taggcataca gctctcaaca tggacagtta tgtgggaccc attccctacc acccttgcca    1440

gggccccaag ttttcaaagg gctagaagaa aaaagagaga aagagagaga gaggcagagg    1500

ggagagaaag agagagagac aaagagggag tcaaagagag atagaaagag aaagatagaa    1560

ctagtaaaga aaaaaagtat gccccattcc tttaaaagcc agggtaaatt taaaacctat    1620

aattgataat tgaaggtctt ctccatgacc ctataacact ccaataccac cttgttttca    1680

gtgtaaacaa gggtgtagcc cgaaaacact gagaccactg acaacccata gccttcctat    1740
```

```
caaaaatcct taacccagga acccatggat ggcccaaatg cattcaatct gtagcagcaa   1800
ctgctttgct aacagaagaa agtagaaaag taacttttag agaaaacctc attgtgagca   1860
cacctcacca gttcagaatt attctaagtc aaaaaagcaa aaaggtagct tactaactca   1920
aaaatcttaa agtatggggt tattctgtta gaaaaaggtg atttaacatt aaccactgaa   1980
aattccctta acccagcagg tttcctaatg ggatttaaat cttcattacc atacaaaggt   2040
ccgaccagac ccagcaggaa ctccctttag gacaggatga tagatggttc ctcctgggtg   2100
attgaggggg tgaaaaacca caatgggtgt tcagtaattg atagggagac tcttgtggaa   2160
ggagagttag gaaaattgcc taataattgg tctgctcaaa tgtgcgagct gtttgcactc   2220
agccaagcct taaagtactt acagaatcaa aaagactcta tctcaatcct gactcaaaat   2280
gttacctaca ccatctctga catgaatttg cataagaact gttgtttatg ggaatgcatc   2340
ttgatggggc agctgggttg ttatgaaata ctcaggaacc cagcccaggt ctagaattca   2400
cctctgagcg caaaggcaat gttggccatg ctggtaaagg accactagaa tccaggagcc   2460
tggacccctt tctttgtggt caagaaaggc gggaaaacag gtgcaggact gctacatcag   2520
agagcataac aaatccgata agcagagttc catgagtggt taagcaccct ggaaaggaac   2580
tcacctctga gtgcaaaggc aatgttaggc acaccagtaa aggaccacta gaatccagca   2640
gcccagaccc ctttctttgt gatcaagaaa ggcgggaaaa ggggtgcagg actgctacat   2700
cagtgagcgt aactaatctg ataagcagaa gtccatgggt ggttacgcac cctggaaagg   2760
aataagcatt aggaccacag aggacactct aagactaatg ctcattggaa aatgactagg   2820
ggtgctggca tccctatgtt ttttttcag atgggaaaca ttccccccaa ggcaaaaacg   2880
cccataagat atattctgga gaattcggcc cagagtgtat gtatcttttt tccctgtcag   2940
acttgaagca aacctaggta aattatcaga tagccctgat ggctatattg atgctttaca   3000
agggttagga caatcctttg atctaacatg gagagatata ctgttactgc tagatcagac   3060
actaatccca aatgaaagaa gtgccaccat aactgcagcc agagagtttg atgatctctg   3120
gtatctcagt caggtcaatg ataggatgac aacagaagaa agaaaacaat tccccacagg   3180
ccagcaggca gttcccagcg tagaccttca ttgggacaca gaatcagaac atggagattg   3240
gtgccgcaga catttactaa cttgcgcgct agaagcacta aggaaaacta ggaagaagcc   3300
tatgaattat tcaatgatgt ccactataac acagggaaag gaagaaaatc ctactgcctt   3360
tctggagaga ctaagggagg cattgagaaa gcatacctct ctgtcacctg actctattga   3420
aggccaacta atcttaaagg ataagttttc cactcagtca gctgcagaca ttagaaaaaa   3480
acttcaaaag tctgcgttag gccgggagca aaacttagaa accctattga acttggcaac   3540
ctcagttttt tatgatagag atcaggagga tcaggtggaa tggacaaatg agattttaaa   3600
aaaaggccac cactttagtc atggccctca ggcaagcaga ctttggacac tctggaaaag   3660
ggaaaagctg ggcaaatcga atgcctaata agacttgctt ccagtgtggt ctacaaggac   3720
actttaaaaa agattgtcca aatagaaata agccaccccc tcgtccatgc tccttatgtc   3780
aagggaatca ctggaaggcc tactgcccca ggggatgaag gtcctctgag tcagaagcca   3840
ctaaccagat gattcagccc caggactcag ggtgcccagg gcaagcgcca gcctatgcca   3900
tcaccctcac agagccctgg gtatgcttga ccattgaggg tcaggaggtt aactatctcc   3960
tggacactgg cgtggccttc tcagtcttac tctcctgtcc cggacaactg tcctccagat   4020
ctgtcactat ccgagggttt ctacgacagc cagccactag atacttctcc cagccactaa   4080
```

-continued

```
gttgtgactg gggaactcta ctcttttcac atgtttttct aattatgcct gaaagcccca   4140
ctcctttgtt agggaaagac attctagcaa aagcaggggc cattatacac ctgaacatag   4200
gagaaggaac acctgtttgt tgtcccctgc ttgaagaagg aattaatcct gaagtctgga   4260
caacagaagg acaatacaga tgagcaacaa atgcctgtcc tgttcaagtt aaactaaagg   4320
attatgcctc ctttccctac caaaggcagt acccccttag acccgaggcc caacaaggac   4380
tccaaaagat tgttaaggac ctaaaagctc aaagcctagc aaaaccatgc agtagcccct   4440
gcaatactcc aattttagga gtacagaaaa ccaacagaca gtggaggtta gtgcaagatc   4500
tcaggattat caatgaggct gttgttccta acccttatac tctgctttcc caaataccag   4560
aagaagcaga gtggtttaca gtcctggacc ttaaggatgg ctttttctgc atccctgtac   4620
atcctgactc tcaattcttg tttgcctttg gagatccttc gaacccaatg tctcaactca   4680
gcttgactgt tttaccccaa gggttcaggg atagccccca tctagttggc caagcattag   4740
ccgagccagt tctcctacct ggacactctt gtcctctggt acatggatga tttattttta   4800
gctgcccgtt cagaaacctt gtgccatcaa gccacccaag tgctcttaaa tttcctcgcc   4860
acctgtggct acaaggtttc caaaccaaag gctcagctct gctcacagca ggttaaatac   4920
ttagggctaa aattatccaa aggcaccagg gccctcagtg aggaatgtat ccagcctgta   4980
ttggcttatc ctcatcccaa aaccctaaag caactaagag ggttccttgg cataacaggt   5040
ttctgccaaa tgtggattcc caggtacggt gaaatagcca ggccattata taccctaatt   5100
aaggaaactc agaaagccaa cacccattta ttaagatgga cacctgaagc agaagcagct   5160
ttccaggccc taaagaaggc cctaacccaa gccccagtgt taagcttgcc aacggggaag   5220
acttttcttt atatgtcaca gaaaaaacag gaatagctct aggagtcctt agacaggtcc   5280
aagggatgag cttgcaacct gtggcatacc tgagtaagga aattgatgta gttgcaaagg   5340
gttgacctca ttgtttacag gtagtggcgg cagtagcagt cttagtatct gaagcagtta   5400
aaataataca gggaagagat cttactgtgt ggacatctca tgatgtaaac ggcgtactca   5460
cttctaaagg agacttgtgg ctgtcagaca accgtttact taaatatcag gctctattac   5520
ttgaagggcc agtgctgcga ctgcccactt gttcaactct taacccagcc acatttcttt   5580
cagacaatga agaaaagata gaacataact gtcaacaggt gattgctcaa acctacggcg   5640
ctcgagggga ccttctagag gttcccttga ctgatcccaa cctcaacttg tatactgatg   5700
gaagctcctt tgtagaaaaa ggactttgaa aggtggggta tgcagtggtc agtgataatg   5760
gaatacttga aagtaattcc ttcactccag gaactagtgc tcagctggca gaactaatag   5820
ccctcactca ggcactagaa ttaggagaag gaaaaagggt aaatatatat gcagactcta   5880
agtatgctta cccagtcctc cacgcccaca cagcaatatg gagagatagg aaattcctaa   5940
cttctgaggg aacaccgatc aaacatcagg aagccattag gagattatta ttggctgtac   6000
agaaacctaa agaggtggca gtcttacact gctggggtca tcagaaagga aaggaaaagg   6060
aaatagaaag gaaccaccaa gtggatattg aagccaaaag agccacaagg caggccctcc   6120
attagaaatg cttatagaag gatccctagt atggggtaat cccctccggg aaaccaagcc   6180
ccagtactca gcaggagaaa tagacacgag gacatagttt cctcccctca ggatggctag   6240
ccaccgaaaa agggaaaata cttttgcctg cagctaatca atggaaatta cttaaaaccc   6300
ttcaccaaac ctttcacttg ggcatggata gcatctatca gatggccaat ttattattta   6360
ctggaccagg ccttttcaaa actatcaagc agatagtcag ggcctgtgaa atgtgccaaa   6420
gaaataatcc cctgcacttc aagccataca tttcaatccc tgtatcttta acctcctgtt   6480
```

```
gtttgtctct tccagactca aagctgtaaa actgcaaatg gttcctcata tggagcccca   6540

gatgcagtcc atgactaaga tctaccacag agccctagac cggcctgtta gcccatgctc   6600

cgatgttgat gacatcaaag gcacaccttc cgaggaaatc tcaactgcac gacccctact   6660

aagccccaat tcagcaggaa gcagttaaga gcagtcgttg gctaacatcc ccaatagtat   6720

gtgggttttc ctgttgagag gggggactga gagacaggac tagctggatt tcctaggcca   6780

actaagaatc cctaagccta gttgggaagg tgaccgcatc cacctttaaa cacggggctt   6840

gcaacttagc tcacacccga ccaatcaggt agtaaagaga gctcactaaa atgctaatta   6900

ggcaaaaaca agaggtaaag aaatagccaa tcatctatcg cctgagagca cagtggggag   6960

ggacaatgat cgggatataa acccaggcat tcgggccggc aacggcaacc cccattgcgt   7020

cccctcccat tgtatgggag ctctgttttc attctattaa atcttgcaac tgcacactct   7080

tctggtctat gtttgttatg gctcgagctg agctttcgct cgctgtccac cactgctgtt   7140

tgccgccatc gcagacccac cactgacttc cacctctgca gatctggcag ggtgtccgct   7200

gtgctcctga cccagcgagc cacccattgc tgctcccaat caggctaaag gcttgccatt   7260

gttcctgcat ggctaagagc ccagggttcg tcctaatcga gctgaacgct agtagctggg   7320

ttccacagtt ctcttccgtg acccacggct cctaatagag ctataacact caccacatgg   7380

cccaaggttc cattcattgg aatccgtgag gccaagaacc cccggtcaga gaacaagaag   7440

cttgccacca tcttggaagc tctaaaaaca gagacacccc agtaaca                 7487
```

<210> SEQ ID NO 2
<211> LENGTH: 7774
<212> TYPE: DNA
<213> ORGANISM: Homo sapiens

<400> SEQUENCE: 2

```
tgagacacag gactagctgg atttcctagg ccgactaaga atccctaagc ctagctggga     60

aggtgaccac atccaccttt aaacacgggg tttacaactt agctcacacc cagccaatca    120

gagagctcac taaaatgcta attaggcaaa aacaggaggt aaagaaatag ccaatcatct    180

attgcctgag agcacagcgg gagggacaag gattgggata taaacccagg cattcgagct    240

ggcaacggca acccccttg ggtctcctcc ctttgcatag gagctctgtt ttcactctat    300

taagtcttgc aactgcactc ttctggtccg tgtttcttac cgcttgagct gagctttccc    360

tcactgtcca ccactgctgt tttgccaccg tcacaggccc accgctgact tccattcttc    420

tggatctagc aggctgtcca ctgtgctcct gatccagcga ggcgcccatt gccgctcccg    480

attgggctaa aggcttgcca ttgttcctgc atggctacgt gcctgggttc atcctaatca    540

agccgaacac tagtcactgg gttccacggt tctcttccat gacccacgac ttctaataga    600

actataacac tcacctcatg gcccaagatt ccattccttg gaatccatga ggccaagaac    660

cccaggtcag agaacacgag gcttgccacc atcttggaag tggccccacc accatcttgg    720

gagctctggg agcaaggacc cccggtaaca ttttggcgac cacaaaggga catccaaagt    780

ggtgagtaat attggaccac tttcacttgc tattctgttc tatccttcct tagaactgga    840

ggaaaatacc aggcacaggc acctgtcagc cagttaaaaa caattagcgt cgccgccaca    900

cttaagactc aggtgtgagg ctatctgggg aaagactttc taacaacccc caacccatct    960

agtggggatg ttggtctgcc tggagacagc ttccactttc aattttcttg gggaagccga   1020

gggctcacta gaggcagaca gctgttgtcc caaactccgg gcagtagccg gttgagatca   1080
```

-continued

```
tggtgcagcc aggagtctct actcagcagt cgccgatgca tgtgccccta ccttcccttc   1140

tgacccatac atcctgagtc ccgactgtga ctttcttgaa agtgtagccc caaaattctc   1200

cttacctctg aatctacttc ctctgatccc tgcctcctgg gtactaatga ttcagacttt   1260

catttcctct agcaagttgt gtctccaaag ggatctaagg aggctctacg ctgcatcctt   1320

aggcacctag gctataaccc aaggagtctt atccctggtg tccctcccga tttgggtata   1380

caactctcaa catgggcagt tatgtaggac ccattcccca ccacacttgc cagggcccca   1440

agtttgtaat ggctaagaga gagacacaga gagagagaga gagatggaga gagagacaag   1500

gagggagtca aagagaaaaa gaaagaaaaa gaaatagtag aaaaaaaagt gtgccctatt   1560

cctttaaaag ccagggtaaa tttaaaacct gtaattgata attgaaggtc ttctccgtga   1620

ccctgtaaca ctccaatgcc attttgttgt cagtgtaaat aagggcatag cccaaaagca   1680

ctgaggtcac tgacaacccg tagctttccc atcaaaaatc cttaacccag taatccgcgg   1740

atgggccaaa tgcattcagt cggtagcagc aaccgctttg ctaaaagtag aaaagtaact   1800

tttagaggaa acctcattgt gagcgcacac ctcaccagtt cagaattatt ctaagtcaaa   1860

aaaaaaaaaa gcaaaaaggt aacttactaa ctcaaaaatc ttaaagtata ggtctatcat   1920

attagaaaag ggtaatgtaa ctccaaccac tgataattcc cttaacccag cagatttcct   1980

aacaggggat ttaaaactta attaccatac aaaggtccca ccagacctag gaggaactcc   2040

cttcaggaca ggacgataaa cggttcctcc caggtgattg aggaaaaaaa ccacaatggg   2100

tattcagtaa ttgatacaga gactcatgtg gaagcagtta gaaaaattgc ctaataattg   2160

gtctcctcaa acgtgtaagc tgtttgcact cagccaagcc ttaaagtact tacagaatca   2220

aaaagactct gaatcctgac tcaaaaggtt tgctacaccc tctgtgaaac aaatttgcat   2280

aagaactgtt gtttatggga aggcatcttg atggggcagc tgggttgtta tgaaatactc   2340

aggaccccag cccggctcta ggactcaccc ctgagcgcaa aaggcaatgt tgggcacgct   2400

ggtaaaggac cactagaatc cagcagcccg gacccctttc tttgtggtca agagaggcgg   2460

gaaaacaggt gcaggactgc tacatcagtg agcataacta atccagtaag cagaggtcca   2520

tgggtggtta tgcaccctgg aaaagaatac gcattaggcc cttagaggat gctctaggac   2580

taatgctcat cggaaaatga ctaggggtgc tgacatccct atgttctttt ttcagatggg   2640

aaacgttcct cccaccccaa ggcaaaaaac accccctaaga tgtattttgg agaattagga   2700

ccaatttgac cctcagacac taagaaagaa atgacttaca ttcttctgca gtaccatgat   2760

atcctcttca agggggagaa acctggcctc ctgagagaag tataaattat aacaccatct   2820

tacagtgaga cctcttctgt agaaaggagg gcaaatggag tgaagtgcaa actttccttt   2880

cattaagaga caactcgcaa ttatgtaaaa agtgtgattt atgccctaca gaaagccctc   2940

agtctacctc cctatcccag ggtccccccg attcctttcc caactaataa ggacccccct   3000

tttacccaaa tggtccaaag gagatagatg aagggataaa caatgaacca aacagtgcca   3060

atattccctg attatgcccc ctccaggcag tgggaggagg agaattcggc ccagccagag   3120

tgcatgtacc tttttttttc tctcagactt aaagcaaatt aaaatagacc taggtaaatt   3180

ctcagataac cctgatggct atattgatgt tttacaaggg ttaggacaat cctttgctct   3240

gacatggaga gatataatgt tactgctaaa tcagacacta accccaaatg agagaagtgt   3300

caccatagct gcagcccaag agtttggcaa tctctggtat ctcagtcagg tcaatgatag   3360

gatgacaaca gaggaaaggg aatgattccc cacaggccag caggcagttc tcagtgtaga   3420

ccctcactgg gacacagaat aagaacatgg agatcggtgc cgcagatatt tgctaacttg   3480
```

```
cgtgctagga ctaaggaaaa ctaggaagaa gcctatgaat tattcagtga tgtccactat   3540
aacacaggga aaggaagaaa atcatactgc ctttccggaa atactaaggg aggcattgag   3600
gaagcatacc tctctgtcac ctgactgtat tgaagtccaa ctaatcttaa aggatatgtt   3660
tatcactcag tcagctgcag acattagaaa aaacttcaaa agtccacctt aggcccagag   3720
caaaacttag aaaccctatt gaacttgtta acctcagttt tttataatag agatcaggag   3780
gagcaggcgg aacaggacaa acaggattaa aaaaagacca ccgctttagt catggccctc   3840
aggcaagtgg actttggaag ctctggaaaa gggaaaagct gggcaaattg aatgcctaat   3900
agggcttgct tccagtgtgg tctacaagga cacttaaaaa aagattgtcc aagtagaaat   3960
aagctgcccc ttcgtccatg cctcttatgt caagggaatc actggaaggc ccattgcccc   4020
aggggaggaa ggtcctctga gtcagaagcc actaaccaga tgatccagca gcaggactaa   4080
gggtgcccag ggcaagcccc agcccatgcc atcaccctca cagagccccg ggtatgcttg   4140
accattgagg gccaggaggt taactgtctc ctgaacactg gcacagcctt ctcagtctta   4200
ctttcctgtc ccggacaact gtcctccaga tctgtcacta tctgagcggt cctaggacag   4260
ccagtcacta gatatttctc ccagccacta agttgtgact ggggaacttt actcttttca   4320
catgcttttc taattatgcc tgaaagcccc actcctttgt tagggagaga cattctagca   4380
aaagcagggg ccattataca tctgaacata ggagaaggaa cacccgtttg ttgtcacctg   4440
cttgaggaag gaattaatgc tgaagtctgg gcaacagaag gacaatatgg atgagcaaag   4500
aatgcccatc ctgttcaagt taaattaaag gattccgcct cctttcccta ccaaaggcaa   4560
taccccctta gacccgaggc ccaacaagga ctccaaaaga ttgttaagga cctaaaagcc   4620
caaggcctag taaaaccatg caatagcccc tgccatactc caattttagg agtaaggaaa   4680
cccaacggac agtggaggtt agtgcaagaa ctcaggatta tcaatgaggc tgttgttcct   4740
ctatacccag ctgtacctaa cccttataca gtgctttccc aaataccaga ggaagcagag   4800
tggtttacag tcctggacct taaggatgcc tttttctgca tccctgtacg tcctgactct   4860
caattcttgt ttgcctttga agatcctttg aacccaacgt ctcaactcac ctggactgtt   4920
ttaccccaag ggttcaagga tagcccccat ctatttggcc aggcattagc ccaagacttg   4980
agccaattct catacctgga cactcttatc cttcggtatg ggatgatttt aattttagct   5040
acccattcag aaacgttgtg ccatcaagcc acccaagtgc tcttaaattt cctcgctacc   5100
tgtggctaca ggtttccaaa cgaaaggctc agctctgctc acagcaggtt aaatacttag   5160
ggctaaaatt atccaaaggc accagggccc tcagtgagga acgtatccag cctatactgg   5220
cttattctca tcccaaaacc ctaaagcaac taagagcatt ccttggcata acaggctgct   5280
gctgaatatg gattcccagg tacagtgaaa tagccaggcc attatacaca ctaattaagg   5340
aaactcagaa agccaatacc catttagtaa gatggacacc ttaagcagaa gcggctttcc   5400
aggccttaaa gaaggcccta acccaagccc cagtggtaag cttgccaaca gggcaagact   5460
tttctttata tgtcacagaa gaaacaggaa tagctctagg agtccttaca caggtctgag   5520
ggatgagctt gcaacccatg gcatacctga gtaaggaaac tgatgtagtg gcaaagggtt   5580
ggcctcattg tttacgggta gtggcagcag tagcagtctt agtatctgaa gtagttaaaa   5640
taatacaggg aagagatctt actgtgtgaa catctcatga tgtgaatggc atagtcactg   5700
ctaaaggaga cttgtggctg tcagacaact gtttacttaa ataccaggct ctattacttg   5760
aagggccagt gctgcgactg tgcacttgtg caactcttaa cccagacaca tttcttccag   5820
```

```
acaatgaaga aaagatagaa cataactgcc aacaagtaat tgctcaaacc tatgccactc   5880
gaggggacct tttagaggtt cccttgactg atcccaacct caacttgtat actgatggaa   5940
gttcctctgt agaaaaagga ctttgaaaag tggggtatgc agtggtcagt gataatggaa   6000
tacttgaaag taatcccctc actccaggaa ctagtgctca gctggcagaa ctaatagccc   6060
tcactcgggc actagaatta ggagaagaga aaagggtaaa tatatacaga ctctaagtat   6120
gcttacctag tcctccatgc ccatgcagca atatggagag aaagggaatt cctaatttcc   6180
aagggaacac ctatccaaca tcaggaagcc attaggagat tactattggc tgtacagaaa   6240
cataaagagg tggcaatctt acactgccgg tgtcaccaga aaggaaagga aagggaaata   6300
gaaaggaacc accaagcgga tattgaagcc aaaagagccg caaggcagga ccctccatta   6360
gaaatgctta tagaaggacc cctagtatgg ggtaatcccc tccaggaaac caagccccag   6420
tactcagaag aagaaataga atgaggaacc tcacaagcac atagtttcct cccctcagga   6480
tggctagcca ctgaagaagg aaaaatactt ttgcctgcag ctaaccaatg gaaattactt   6540
aaaacccttc accaaacatt tcccttaggc attgatagca cccatcagat ggccaaatta   6600
ttatttactg gaccaggcct tttcaaaact atcaagcaga tagtcagggc ctgtaaagtg   6660
tgccaaacaa gtaatcccct gcactgcagg ccatacattt caatccctgt atctttaacc   6720
tccttgttaa gtttgtctct tccagaatca aagctgtaaa actacaaata gttcttcaaa   6780
tggagcccca gatgtagtcc atgactaaga tctaccgcgg acccctggac aagcctgcta   6840
gcccatgctc tgatgttaat gacatggaag gcacccctcc cgaggaaatc gcaactgcac   6900
aacccctatt acaccccaat tcagcaggaa gcagttagag cattcatcag ccaacctccc   6960
caacagcact tgggttttcc tattgagagg gggtactgag agacaggact agctggatgt   7020
cctaggctga ctaagaatcc ctaagcctag ctgggaaggt gaccacatcc acctttaaat   7080
acggggcttg caacctagct cacacccaac agatcagaga gctcgttaaa atgctaatta   7140
ggcaaaaaca ggaggtaaag aaatagccaa tcatctattg cctgagagca cagcaggagg   7200
gacaaggatt gggatataat cccaggcatt cgagctggca acagcaaccc cctttgggtc   7260
ccctcccttt gtatgggagc tgttttcact ctatttcact ctattaaatc ttgcaactgc   7320
actcttctgg tgcatgtttg ttactgcttg agctgaactt tcactcgcca tctaccactg   7380
ctgttttgcc gccgtcgcag acccactgct gacttccatt cttctggatc cagcagggtg   7440
tccactgtgc tcctgatcca gtgaggcacc cattgccgct cccgatctgg ctaaaggctt   7500
gccattgttc ctgcatcgct aagtgcctgg gttcgtccta atcaagctga acactagtca   7560
ctgggttcca cagttctctt ccatgaccca cgacttctaa tagagctata acactcacct   7620
tatggcccaa gattccattc cttggaatcc atgaggccaa aaaccccagg tcagagaaca   7680
tgagacttgc caccatgttg aagtggcctg ctgccatttt ggaagtggcc caccaccatc   7740
ttgggagctc tgggagcaag gacccctggt aaca                               7774
```

<210> SEQ ID NO 3
<211> LENGTH: 5470
<212> TYPE: DNA
<213> ORGANISM: Homo sapiens

<400> SEQUENCE: 3

```
tgagagacag ctggatttcc taggccgact aagaatccct aagcctagct gggaaggtga     60
ccgcatccac ctttaaacac agggcttgca acttagctca cacccaacca atcagagagc    120
tcactaaaat gctaattagg caaaaacagg aggtaaagaa atagcaagtc atctattgcc    180
```

-continued

```
tgagagcaca gtgggaggga caaggaccag gatataaacc caggcatttg agccagcaac    240
ggcaacctcc tttgagtccc ctccctttgt ataggagctc tgttttcact gtgtttcact    300
ctattaaatc ttgcaattgc actcttctgg tccatatttg tcacggcttg agctgagctt    360
tcacttgccg tccaccacta ctgtttgctg ctgtcacaga cccgccgctg actcccatcc    420
cgctgctgac tcccatccct ccggatccgg cagggtgtcc gctgtgctcc tgatccagca    480
agactcccat tgccactccc gatagtgcta aaggcttgcc attgttcctg catggctaag    540
tgcctgggtt cgtcctaatc cagctgaaca ctagtcactg ggttccacgg ttctcttcca    600
tgacccgcgg cttctaatag agctataaca ctcaccacat ggcccaatat tccattcctt    660
ggaatccgtg aggccaagaa ccccaggtca gagaacacga ggcttgccac catcttggaa    720
gcagcctgcc accatcttgg aagtggctca ccaccgtctt gggagttctg tgaacaagga    780
cccctggtaa cattttggcg accacgaagg gacatccaaa gctgtgagta atattggacc    840
actttcgctt gctattctgt tctatcctta gaactggagg aaaatactgg gcacctgtcg    900
ccagttaaaa atgattagca tggccgccgg acttaagact caggtgtgag gctatctggg    960
aaagggcttt ctaacaaccc ccaagccttc tgttgggaac tttggtctgc ctggagccag   1020
cttccacttt caattttctt ggggaagcca agggctgact ggaggcagaa agctgttgtc   1080
ccgaactccc ggcagtagcc ggttgagatc atggcgcagc cagaagtctc tactcggcag   1140
tcgcccatgc gtgcgccctt acctttcctt ctgaattata cctccggggt cccgactccg   1200
actttcttga gagtttagcc ccaaaattct ccttacctct gaatctactt cctttgatcc   1260
ctgcctcctg cctcctaggt actaatagtt cagactttca tttcctctag caagttgtgt   1320
ctccaaaggg atctaaggag gctctatgct gtgtccttag gcacctaggc tataacccag   1380
ggagtcttat ccctggtatc cctcccgatt taggtataca gctcttgaca tgggcagtta   1440
tgtgggacct gttccccacc acccttgtga gggccccaag tttgtaatgg ctaagaaaga   1500
gagacggaga gagagagaga cggagaaaga gacaaagagg gagtcaaaga gaaaaagaaa   1560
gaaaaagata gaaatagtta aaaaaaaaaa aaagtgtgcc ctattccttt aaaagccagg   1620
gtaaatttaa aacctgtaat tgataattgc cactttgttg tcagtgtaaa taagggcgta   1680
gcaaatcctt aacccagtaa cccgcggata ggccaaatgc attcagtcgg tagcggcaac   1740
agctttgcta aaagtagaaa agtaactttt agaggaaacc tcattgtgag cacacctcac   1800
cagttcagag ttattctaag taaaaaaaaa aaaaaaaaaa aaagcaaaaa ggtagcttac   1860
taactcaata atcttaaagt atggggctac tatgctagaa aagggtaatg taactccaac   1920
cactgataac tcccttaacc cagcagattt cctaacaggg gatttaaatc ttaattacca   1980
cacgaaggtc cgaccagacc taggaggaac tcccttcagc acaggacgat agatggttcc   2040
tcccaggtga ctgaggaaaa aactacaatg ggtattcagt aattggtatg gagactcttg   2100
tggaagcaga gttaaaaatt tgcctaataa ttggtctcct caaatgtgcg agctgtttgc   2160
actcagccaa gccttaaagt acttacagaa tcaaaagact atctcaatcc tgactcaaaa   2220
ggttagctac acagtctctg aaatgaattt gcagaagaac tgttgtttat gggaatgcat   2280
cttgatgggg cagctgggtt gttatgaaat actcaggaac ccagcccagc tctaggactc   2340
accgctgagc gcaaaggcaa tgttgggcac gctggtaaag gaccactaga atccagcagc   2400
ccaggcccct ttctttgtgg tcaagaaagg caggaaaagg agtgcagaac tgctacattg   2460
gtgagcgtaa ctaatccaat aagcagaggt ccatgagtgg ttatgcacgc tggaaaagaa   2520
```

```
taagcattag gcccttagag gatgctctag gactaatgct catcggaaaa tgactagggg   2580
tgctggcatc cttatgttct ttcttcagat gggaaacgtt ccccccaagg caaaagcgcc   2640
cctaagatgt attctggaga attagaacca atttgaccct cagatgtcaa gaaagaaacg   2700
acttatattc ttctgcagta ctgcctggcc acgatatcct cttcaagggg gagaaacctg   2760
gcctcctgag ggaagtacaa attataacac catcttacag ctagacctct tttgtagaaa   2820
agaaggcaaa tggagtgaag tgccatatgt gcaaactttc ttttcattaa gagacaactc   2880
acaattatgt aaaaagtgtg gtttatgtct tacaggaagc cctcagagtc tacctcccta   2940
tcccagcatt cccccgactc cttccccaac taataagcac caccccttgaa cccaaacagt   3000
ccaaaaggag atagacaaac aggtaaacaa tgaaccaaag agtgtcagta ttccccgatt   3060
atgcccctc caagcagtgg gaggaggaga attcggccca gccagagtgc atgtaccttt   3120
ttctctctca gacttaacgc aaattaaaat agacttaggt aaattctcag ataaccctga   3180
tggctacatt gatgttttac aagggttagg gcaatccttt gatctgacat ggagagatat   3240
aatgttactg ctaaatcaga cactaacccc aaatgagaga agtgccgccg taactgcagc   3300
ccgagagttt ggtgatctct ggtatctcag tcaggtcaat gataggatga caacagagaa   3360
aagagaacga ttccccacag gccagcaggc agtttccagt gtagaccctc attaggacac   3420
agaatcagaa catggagatt ggtgccacag atatttgcta acttgagtgc tagaaggact   3480
aaggaaaact aggaagaagc ctatgaatta ttcagtgatg tccactataa cacaaggaaa   3540
ggaagaaaat cctactgcct ttctggagag agtaagggag gcattaagga agcatacctc   3600
cctgtcacct gactctattg aaggccaact aatcttaaag gataagtttg tcactcagtt   3660
agctgcagac attagaaaaa aacttcaaaa gtccgactta ggcctggagt acggctgagt   3720
gcccaatttg gcagcaggca agaccaacac tgagcccttc atatggcacc atgctttgtg   3780
gtgatcagcc aactacttga tggcaggttg attatattgg acatctttca tcagagaaat   3840
ggcagtggtt tgtccttcct ggaatagaca cttattctcg atatgggttt gtctatcctg   3900
caggcaatgc ttctgccagg agtaccatct gtggactcat ggaaagcctt atccaccatc   3960
atggcattcc acacagcatt gcctctaaac aaggcactta ttttatagct aaggaagtgt   4020
ggcagtgggc tcatgctcat ggaattcact gattgtatct tgttgcccat tatcttaaag   4080
cagctggatt gatagaacag tggaaaggcc atttgaaatc acaattacac caccaactag   4140
gtgacaatac tttgcagggc tcggcaaagt tctcttgaag gctgagtatg tcctgaatca   4200
gcatccaata tatggtactg tttccctcat agccagcatt cacaggccta agaatcaagg   4260
ggtagaagta gaagtggcac cactcaccat cactcctagt gacccactag caaaaatttt   4320
acttccagtt cccccaacat tatgttctgc tggccttagt tccagaggga agaattctgc   4380
caccagtcga cacaagaatg ataccattaa actgaaagtt aaaattgcca cctggccact   4440
ttgggctcct cccacctcta agtcaacagg tcaagaaagg agttacagtg ttgacttggg   4500
tgattgacct ggactatcaa gatgaaatca ggttactact ccacagtgga ggtaaggaag   4560
aatatgtgtg gaatacagga gatcccttag gccgtctttt agtactacca tgccctgtga   4620
ttaaggtcag tggaaaacta caacaatcca atctaggcag gactacaaat ggcccagact   4680
cttcaggaat gaagggttgg gtgacttcac caggtaaaaa aataacagcc tgctgaggtg   4740
ctagctgaag gcaaagggaa tacagaatgg ttagtagaaa aaggtagtca tcaataccag   4800
ctatgaccac aagaccagtt gcagaaatga gacctgtaat tgtcatgtgg atttcctcct   4860
tacatgtttg tgcatgtata cacttctact aagaaaatac ctttatttat ttcctttgct   4920
```

```
tttcccttat caagtgacat tattaacttc atatcagcag ttaagtgtta ttaactttat   4980

gtaatagcat ttcggttaat aattcacttc tggttgtatg aaggatagcc gtattaagtt   5040

aggtgtaatt atgacatcat tattgtcttt atttgaagat tatgtgtaat ttcaggagat   5100

gtgtatgggt tcaagttgac aagggatgga cttgtgatgg ctaatgttga gtgtcaactt   5160

gactgaggat gcaaagtatt gttcctgggt gtgtctgtga gggtgttgcc aaaggagatt   5220

aacatttgtg tcagtgaact gggagatgca gacccacccg caatctgggt gagcaccatg   5280

taatcagctg ccagagcagc tagaataaag caagcagaag aaggtggaag gagctgactt   5340

gctgagtctt ctagtattct tcgttcttct atgctggttg cttcctgccc ccaaacatca   5400

gtctgcaagt tcttctgctt ttggactctt ggacttacac cagtggtttg ccagggactc   5460

tcgggccttc                                                          5470
```

<210> SEQ ID NO 4
<211> LENGTH: 783
<212> TYPE: DNA
<213> ORGANISM: Homo sapiens

<400> SEQUENCE: 4

```
tgagagacag gactaactgg atttcctagg ccgactaaga atccctaagc ctagctggga     60

aggtgaccgc atccatcttt aaacacgggg cttgaaactt agctcacacc taaccagtca    120

gagagctcac taaaatgcta attaggcaaa aaacaggagg taaagaaata gccaatcatc    180

tattgcctga gagcacagcg ggagggacaa ggatcgggat ataaacccag gcattcgagc    240

cagcaatggc aaccccccttt gggtcccctt cccttgtatg ggagctctgt tttcactcta    300

tttcactcta ttaaatcttg caactgcact cttctggtcc atgtttgtta cggctcgagc    360

tgagctttgg ctcgccatcc accactgctg tttgccgccg tcgcacacct gctgctgact    420

cccatccctc cggatccagc agggtgtgtc cgctgtgctc ctgatccagc gaggtgccca    480

ttgccgctcc tgattggact aaaggcttgc cattgttcct gcacggctaa gtgcccgggt    540

tcgtcctaat ccagctgaac actagtcact gggttccacg gttctcttcc ttgacccacg    600

gcttctaata gagctataac actcaccgca tggcccaaga ttccattcct tggaatctgt    660

gaggccaaga accccaggtc agagaacacg aggcttgcca ccatcttgga agcggcctgc    720

caacatcttg gaagtggctc gccaccatct tgggagctct gtgagcaagg acccctggta    780

aca                                                                  783
```

<210> SEQ ID NO 5
<211> LENGTH: 7542
<212> TYPE: DNA
<213> ORGANISM: Homo sapiens

<400> SEQUENCE: 5

```
tgagagacag gactagctgg atttcctagg ccgactaaga atccctaagc ctagctggga     60

aggtgaccgc ttccaccttt aaacacgggg cttgcaactt agctcacacc cgaccaatca    120

gatagtaaag agagcacact aaaatgctaa ttaggcaaaa acaggaggta aagaaatagc    180

caatcatcta ttgcctgaga gcaaagcggg agggacaatg atcgggatag aaacccaggc    240

attcaagccg gaatggctac cctctttggg tcccctccct ttgtatggga gctctgtttt    300

cactctattc aatcttgcaa ctgcactctt ctggtccgtg tttgttacag cttgagctga    360

gctttcgctc gccttccacc actgctgttt gccgccatcg cagacctgcc gtgctgactt    420
```

```
ccatccctct agatctggca gggtgtccgc tgtgctcttg atccagcgag gcgcccattg    480
ccgctcccga ttgggctaaa ggcttgcaat tgttcctgca cgctaagtgc ctgggttcat    540
cctcatcaag ctgggttcca cggttctctt catgacccgc agcttctaac agagctataa    600
aactctgtgc atggcccaag attccattcc ttggaatctg tgaggccaag aaccccaggt    660
cagagaacag gaggcttgcc accatcttgg aagtggctcg ccaccatctt aggagctctg    720
tgagcggaga cccccacccc ccggtaacat tttggcgacc acgaagggac ctccaaagcg    780
gtgagtaata ttggatcact ttcgcttgct attctgtcct atccttcttt agaattggag    840
gaaaatactg ggcacctgtc ggccagttaa aaacaattag cgtggctgcc cgacttaaga    900
ctcaggtgtg aggctatctg ggaagggct ttctaacaac ccccaaccct tctgggttgg    960
ggacgttggt ctgccccttc cactttcaat ttttcttgggg aagccaaggg tcgactagag   1020
gcagaaagct gtcgtccgga actcctggca gtagccggtt gagatcatgg cgcagccaga   1080
agtctctact caacagtcgc ccatgcgtgc gctcctacct ttcctcctga cccatacctc   1140
ctgggtcccg acgatgactt tcttgaaagt gtagccccaa aattctgctt acctctgaat   1200
ctacttcccc tgatccctgg ctcctaggta ctaatggttc agtttcattt cctctagcaa   1260
gttgtatctc caaagggatc taaggaagct ctacgctgcg tccttaggca tctaggctat   1320
aaacccagga agtcttgtcc ctggtgtccc tcccgattta ggcatacagc tctcgacatg   1380
ggcagttatg tgggacccgt tccccatcac ccttgtcaag gccccaagtt tgtaatggct   1440
aagaggagag agagagaaag agagagagac ggaggggaga gagagagaga gagatggagg   1500
ggagagagag agagagagac ggaggggaga gagagagaga gagagagacg gaggggagag   1560
agagagagac ggaggggaga gagagagaga tggaggagag aaagacaaag ggagtcaaag   1620
agaaaaagaa agagaaagac agaaatggta aaacaaacaa aaaacagcgt gccctattcc   1680
tttaaaagcc ggggtaaatt taaaacctat aattgataat tgaaggtctt ctccatgacc   1740
ctataatact ccaatactac cttgttgtca gtgtaaacaa gggcgtagcc tgaaaacact   1800
gagaccactg acaacctgca gctttcctat caaaaaatcc ttaacccagt aaccggcaga   1860
tgcattcaat ctgtagcagc aactgttttg ctaacagaag aaagtagaaa agtaactttt   1920
agaggaaacc tcattgtgag cacaccttac cagttcagaa ttattctaag tcaaaaaagc   1980
aaaaaggtag cttactaact caaaaatctt aaagtatggg gctattgtgt ttaaaaaaaa   2040
aaaaaggtaa tttaacacca accactgata attctcttaa cccagcaggt ttcctaacag   2100
gggatttaaa tcttaattac catacaaagg tctgaccaca cctaggagga actcccttca   2160
ggacaggact atagagggtt cctcccaggt gattgaggaa aaaaccacag tgggtattca   2220
gtaattgata gggagactct tgtggaagca gagttagaaa aattgcctaa taaatggtgt   2280
cctcaaaagt gtgagctgtt tgcactcagc caagccttaa agtacttaca gaatcgtaaa   2340
aactatctca atcctgactc aaaagtttac ttacaccctc tctgaaatga atttacataa   2400
gaactgcttt tttgggaatg catcttgatg gggcagctgg gtggttatga aatactcagg   2460
aaaccagccc agctctagga cacatccctg agcacaaagg caatgttggg cacgctggta   2520
aaggaccact agaatccagc agcctggact cctttctttg tggtcaagaa aggcaggaaa   2580
acaggtgcag gactgctaca tcagtgagca taactaatct gataagcaga gggccttggg   2640
tggttacaca ccctggaaag gaattcaact ctgagcgcaa aggcaatgtt gggcacattg   2700
gtaaaggacc actagaatcc agcagcccag gcccctttct ttatggtcaa gaaaggcggg   2760
aaaaggggtg caggactgtt acctcggtga gcgtaactaa tccgataagc agaggtccat   2820
```

```
gggtgattac gcaccctgaa aagaataagc attaggccct taaaggatgc tctaggacta   2880

atgctcattg gaaaatgact aggggtgctg gcatccctat gttcttttct cagacgggaa   2940

atgttctcca ccctccccaa ggcaaaaaca ccccctaagat gtattctgga gaattgggac  3000

caatttgacc cccagacgct aagaaagaga tgacttatgt tcttctgcag taccacctgg   3060

ccacgatatc ctcttcaagg gggagaaacc tggcctcctg agggaagtat aaattataac   3120

accatcttac agctagacct cttctgtaga aaggagggca aatggagtga agtgccatat   3180

gtgcaaactt tcttttcatt aagagacaac ttgcaattat gtaagaagtg tgatttatgc   3240

cctacaggaa gccctcagag tctacctccc taccccagca tccccctgac tccttctcca   3300

actaataagg aaccccttc aacccaaacg gtccaaaagg agatagacaa aggggtaaac    3360

aatgaaccaa agcgtgccaa tgttccctga ttatgccccc tctaagcagt gggaggagga   3420

gaatttggcc cagccagtgt gcatgtgcct tttctctct cagacttaaa gcaaattaaa    3480

atagacctag gtaaattctc agataaccct gatggctata ttgatgtttt ataagggtta   3540

ggataatcct ttgatctgac atggagagat ataatgttac tgctagatca gacactaacc   3600

ccaaatgaga caagtgccgc cataactgca gcctgagagt ttggcgatct ctggtatctc   3660

actcgggtca atgataggag gacaacagag gaaagagaat gattccccac agaccagcag   3720

gcagttccca gtgtagaccc tcactgggac acagaatcag aacatggaca ttggtgctgc   3780

agacatttgc taacttacat gctagaagga ctaaggaaaa ctaggaagaa gcctacgaat   3840

tattcaatga tgtccactat aacacaggga aaggaagaaa atcctactgc ctttctggag   3900

cgactaaggg aggcattgag gaagcatact tccctgtcac ctgactctat tgaaggccaa   3960

ctaatcttaa aggataagtt tatcactcag tcagctgaag acattaggaa aaaacttcaa   4020

aagtctgcct taggcccaga gcaaaactta gaaaccccat tgaacttggc aacctcggtt   4080

ttttataata gagatcagga ggagcaggcg gaacaggaca aacggggtaa aaaaaaggcc   4140

accgctttag ttatggccct caggcaagtg gactttggag gctctggaaa agggaaaagc   4200

tgggcaaatc gaatgcctac tagggcttgc ttccagagtg gtctacaagg acactttgaa   4260

aaagattgtc caagtagaaa taagtcgccc cttcgtccat gccccttata tcaagggaat   4320

cactggaagg cccactatcc caggggacaa atgtcctctg agtcagaagc cactaaccag   4380

atgatccagc agcaggactg agggtgccca gggcaagcac tagcccatgc cgtcaccctc   4440

acagagcccc aggtatgctt gaccattgag ggccaggagg ttaactgtct cctggacact   4500

agcacggcct tctcagtctt actctccttt cccggacaac tgtcctccag atctgtcact   4560

atccgagggt tcctaggaca gtcagtcact agatacttat cccagtcact aagttgtgac   4620

tggtgaactt tactcttttc acatgctttt ctaattatcc ctgaaagcac cactcccttg   4680

ttagggcgag acattctagc aaaagcaggg gccattatac acctgaacat aggagaagga   4740

acacctgttt gttgtcccct gcttgaggaa ggaattaatc ccgaagtctg ggcaacagaa   4800

ggacaatacg gacgagcaaa gaatgcctgt gctgttcaag ttaaactaaa ggattccgcc   4860

tcctttccct accaaaggca gtaccccctt agacctgagg cccaacaagg actccaaaag   4920

attgttaagg acctaaaagc ccatggccta gtaaaaccat gcaatagccc ctgcaatact   4980

ccaattttag gagtacagaa acccaacaga cagtggaggt tagtgcaaga tctcaggatt   5040

atcattgagg ctgttgttcc tgtatagcca gctgtaccta acccttatac tctgctttcc   5100

caaataccac aggaagcaga ggggtttaca gtccggggcc ttaaggacac ctttttctgc   5160
```

```
atccctgtat atcctgactc tcaattcttg tttgcctttg aagatccttc aaactcaacg   5220
tctcaactca cctggaatgt tttaccccaa gggttcaggg atagccccca ttagcccaag   5280
acttgagcca gttcttatac ctggacactc ttgtcctttg gtacgtggat gatttacttt   5340
tagccacctg ttcagaaacc ttgtgccatc aagccaccca agcactcttt aatttcctcg   5400
ccacctgtgg ctacaggttt ccaaaccaaa ggctcagctc tgctcacagc aatttaaatg   5460
cttagggcta aaattatcca aaggcaccag ggccctcagt gaggaaagta tccggcctat   5520
actggcttat cctcatccca aaaccctaaa gcaactaaga gtgttccttg gcataacggg   5580
tttctgccga atatggattc ccaggtacag cgaaatagcc agaccattat atacactaat   5640
taaggaaact cagaaagcca atacccattt ggtaagatgg acacctgaag cagaagcaga   5700
tttccaggcc ctaaagaagg ccctgaccca agccccagtg ttaagcttgc caatggggca   5760
agacttttct ttatatgtca cagaaaaaac aggaatagct ccaggagtcc ttacgcagat   5820
ccaagggacg agcctgcaac ccatggcata cctgagtaag gaaattagtg gcaaagggtt   5880
ggcctcattg tttatgggta gtggcagcag tcacagtctt agtaactgaa gcagttaaaa   5940
tgatacaagg aagagatctt actgtgtgga catctcatga tgtgaatggc atactcactg   6000
ctaaaggaga cttgtgactg tcagacaact gtttacttaa atatcaggct ctattacttg   6060
aagggccagt gttgcgactg tgcacttgtg caactcttaa cccagccaca ttgcttccag   6120
acaatgaaga aaagatagaa cataactgtc aacaaataat tgctcaaacc tacactgctc   6180
gaggggacct tttagaagtt cccttgactg atcccgatct caacttgtat actgatggaa   6240
gttcctttgc agaaaaagga cttcaaaagg cggtgtatgc agtagtcctt caaaatcgaa   6300
gagctttaga attgctaatc actgagagag gggaacgtt tttatttttta ggggaagaat   6360
gctgttatta tgttaatcaa ttcggaatca tcaccaagaa agttaaagaa attcaagatc   6420
gaatacaacg tagaacagag gagcttaaaa aacactggac cctggggcct cctcagccaa   6480
tggatgccct ggattctccc cttcttagga cctctagcag ctatatttct actcctcttt   6540
ggaccctgta tctttaacct ccgtgttaag tttgtctctt ccagaatcga agatgtaaaa   6600
ctacaaatcg ttcttcaaat ggacccccag atgcagtcca tgactaagat ctactgagga   6660
cccctggacc agcctgctag cccatgctcc aatgttaatg acattgaagg cacccctccc   6720
aaggaaatct caactgcaca acccctacta tgctccaatt cagcaggaag cagttacagt   6780
ggtcctcggc caacctcccc aacagcattt gtattttcct gttgggaggg ggcactgaga   6840
gacaggacta gctggatttc ctaggctgac tgagaatccc taagcctagc tgggaaggtg   6900
accacttcca cctttaaaca cagggcttgc aacttagctc acaccctacc aattggatag   6960
taaagagagg tcactaaaat gctaattagg caaaaacagg aggtaaagaa atagccaatc   7020
atccattgcc tgagagcaca gcgggaggga caatgaccag gatataaacc caggcattcc   7080
agcctgcaac ggcaaccccc tttgggtccc ctctctttgt atgggagctc tgttttcact   7140
ctattcaatc ttgcaactgc actcttctgg tccgtgtttg ttacggctca agctgagctt   7200
ttgctcacca tccaccactg ctgtttgccg ccgttgcaga cccgtcgctg acttccatcc   7260
ctccagatct ggcagggtgt ccactgtgct cctgatccag cgaggcaccc attgccactc   7320
ccgatcaggc taaaggcttg ccattgttcc tgcacagcta agtgcctggg ttcgtcctaa   7380
tcaagctgaa cactagtcac tgggttccat ggttctcttc catgacccat ggcttctaat   7440
agagctataa cactcaccgc atggcccaag attccattcc ttggaatccg tgaggccaag   7500
aaccccaggt cagagaacac gaggctgccg ccatcttgga ag                       7542
```

<210> SEQ ID NO 6
<211> LENGTH: 10288
<212> TYPE: DNA
<213> ORGANISM: Homo sapiens

<400> SEQUENCE: 6

```
cctggggcgg gcttcctttc tgggatgagg gcaaaacgcc tggagataca gcaattatct     60

tgcaactgag agacaggact agctggattt cctaggccga ctaagaatcc ctaagcctag    120

ctgggaaggt gaccacgtcc acctttaaac acggggcttg caacttagct cacacctgac    180

caatcagaga gctcactaaa atgctaatta ggcaaagaca ggaggtaaag aaatagccaa    240

tcatctattg cctgagagca cagcaggagg gacaacaatc gggatataaa cccaggcatt    300

cgagctggca acagcagccc ccctttgggt cccttccctt tgtatgggag ctgttttcat    360

gctatttcac tctattaaat cttgcaactg cactcttctg gtccatgttt cttacggctc    420

gagctgagct tttgctcacc gtccaccact gctgtttgcc accaccgcag acctgccgct    480

gactcccatc cctctggatc ctgcagggtg tccgctgtgc tcctgatcca gcgaggcgcc    540

cattgccgct cccaattggg ctaaaggctt gccattgttc ctgcacggct aagtgcctgg    600

gtttgttcta attgagctga acactagtca ctgggttcca tggttctctt ctgtgaccca    660

cggcttctaa tagaactata acacttacca catggcccaa gattccattc cttggaatcc    720

gtgaggccaa gaactccagg tcagagaata cgaggcttgc caccatcttg gaagcggcct    780

gctaccatct tggaagtggt tcaccaccat cttgggagct ctgtgagcaa ggacccccg    840

gtaacatttt ggcaaccacg aacggacatc caaagtggtg agtaatattg gaccactttc    900

acttgctatt ctgtcctatc cttccttaga attggaggaa aataccgggc acttgtcggc    960

cagttaaaaa cgattagtgt ggccaccgga cttaagactc aggtgtgagg ctatctgggg   1020

aagggctttc taacaacccc caacccttct gggttgggga cttggtttgc ctcaagccag   1080

cttccacttt cagttttctt ggggaagccg agggccgact agaggcagaa agctgtcgtc   1140

ctgaactccc ggcagtagcc ggttgagatc atggtgtagc cagaagtctc aacagtcgcc   1200

catgcatgca cccctatctt tccttctgac ccatacctcc tgggtcccaa ccacaacttt   1260

cttcaaagtg tagccccaaa attctcctta cctctgaata tacttcctct gatccctgcc   1320

tcctaggtac tattggttca gacttccatt tcctctagca agttgtatct ccaaagggat   1380

ctaaggaagc tctgcgctgc gtccttaggc acctaggcta taacccaggg agtcttatcc   1440

ctggtgtccc tcccaattta ggcatacagc tcttgacatg ggcagttatg taggacccac   1500

tccccaccac ccttgccagg gccccaagtt tgtaaatggc tgagggaaaa gagagacaga   1560

ggagagagag agaaatggag gagaaagaga gagagacaga gaggagagag agacagtgag   1620

agagacagaa gagagagaga gacaaagagg agagagagag agtcaaagag agaaagaaag   1680

agaaagaaat agtaaaaaac agtgtgccct attcctttaa aagccagggt aaatttaaaa   1740

cctgtacttg ataattgaag gtcttctctg tgaccctata gcactccaat ccactttgtg   1800

gtcagtgtaa ataagagcat aggccgaaag cactgaggcc attgacaacc cgtagcttcc   1860

ctatcaaaaa tccttaaccc agtaacccgc agatggacca aatgcattca gtcggtagcg   1920

caactgcttt gctaaaagta gaaaagtaac ttttagagga aacctcattg tgagcacacc   1980

tcacctgttc agaattattc taataaaaaa agcaaaaagg tagcttacta actcaaaaat   2040

cttaaagtat ggggctattc tgttagaaaa aggtaatgta actccaacca ctgataattc   2100
```

```
ccttaaccca gcagatttcc taacgggatt taaatcttaa ttaccataca aaggtccgac   2160
cagacctagg cggaactccc ttcaggacag gacgatagat ggttcctccc aggtgattga   2220
ggaaaaaaac cacaatgggt attcagtaat tgatacgggg actcttgtgg aagcagagtt   2280
agaaaaattg cctaataact ggtctcctca aacgtgtgag ctgtttgcac tcagccaagc   2340
cttaaagtac ttacagaatc aaaagactat ctcaatcctg attcaaaagg ttagctacac   2400
cctctctgta atgcatttgc ataagaactt gtttatggga atgcatcttg atggggcagc   2460
tgggttgtta taaaatagga acccagccca gctctaggac tcacccctga gcgcaaaggc   2520
aatgttgggc atgctggtaa aggaccacta gaatccagca gcccagaccc ctttctttgt   2580
ggtcaagaaa ggcgggaaaa ggggtgcagg actgctacat cggtaagcat aactaatccg   2640
ataaacagag gtccatgggt ggttacgcac cctggaaagg aactcacccc tgagcacaaa   2700
ggcaatgttg ggcacgctgg taaaggacca ctagaatcca gcagcctgga cccctttctt   2760
tgtggtcaag agaggcagga aaacaggtgc aggactgcaa catcagtgag cataactaat   2820
tcgataagca gaggtccatg ggtggtgatg caccctggaa agaataagca ttaggaccat   2880
agaggacact ccaggactaa agctcatcgg aaaatgacta gggttgctgg catccctatg   2940
ttcttttttc agatgggaaa cgttccccgc aagacaaaaa cgcccctaag acgtattctg   3000
gagaattggg accaatttga ccctcagaca ctaagaaaga aacgacttat attcttctgc   3060
agtgccgcct ggcactcctg agggaagtat aaattataac accatcttac agctagacct   3120
cttttgtaga aaaggcaaat ggagtgaagt gccataagta caaactttct tttcattaag   3180
agacaactca caattatgta aaaagtgtga tttatgccct acaggaagcc ttcagagtct   3240
acctccctat cccagcatcc ccgactcctt ccccaactaa taaggacccc ccttcaaccc   3300
aaatggtcca aaaggagata gacaaaaggg taaacagtga accaaagagt gccaatattc   3360
cccaattatg accccctccaa gcagtgggag gaagagaatt cggcccagcc agagtgcatg  3420
tgccttttc tctcccagac ttaaagcaaa taaaaacaga cttaggtaaa ttctcagata    3480
accctgatgg ctatattgat gttttacaag ggttaggaca attctttgat ctgacatgga   3540
gagatataat gtcactgcta aatcagacac taaccccaaa tgagagaagt gccaccataa   3600
ctgcagcctg agagtttggc gatctctggt atctcagtca ggtcaatgat aggatgacaa   3660
cagaggaaag agaatgattc cccacaggcc agcaggcagt tcccagtcta gaccctcatt   3720
gggacacaga atcagaacat ggagattggt gctgcagaca tttgctaact tgtgtgctag   3780
aaggactaag gaaaactagg aagaagtcta tgaattactc aatgatgtcc accataacac   3840
agggaaggga agaaaatcct actgcctttc tggagagact aagggaggca ttgaggaagc   3900
gtgcctctct gtcacctgac tcttctgaag gccaactaat cttaaagcgt aagtttatca   3960
ctcagtcagc tgcagacatt agaaaaaaac ttcaaaagtc tgccgtaggc ccggagcaaa   4020
acttagaaac cctattgaac ttggcaacct cggtttttta taatagagat caggaggagc   4080
aggcggaaca ggacaaacgg gattaaaaaa aaggccaccg ctttagtcat gaccctcagg   4140
caagtggact ttggaggctc tggaaaaggg aaaagctggg caaattgaat gcctaatagg   4200
gcttgcttcc agtgcggtct acaaggacac tttaaaaaag attgtccaag tagaagtaag   4260
ccgccccctc gtccatgccc cttatttcaa gggaatcact ggaaggccca ctgccccagg   4320
ggacaaaggt cctctgagtc agaagccact aaccagatga tccagcagca ggactgaggg   4380
tgcctggggc aagcgccatc ccatgccatc accctcacag agccctgggt atgcttgacc   4440
attgagggcc aggaggttgt ctcctggaca ctggtgcggt cttcttagtc ttactcttct   4500
```

```
gtcccggaca actgtcctcc agatctgtca ctatctgagg gggtcctaag acgggcagtc   4560
actagatact tctcccagcc actaagttat gactggggag ctttattctt ttcacatgct   4620
tttctaatta tgcttgaaag ccccactacc ttgttaggga gagacattct agcaaaagca   4680
ggggccatta tacacctgaa cataggagaa ggaacacccg tttgttgtcc cctgcttgag   4740
gaaggaatta atcctgaagt ctgggcaaca gaaggacaat atggacgagc aaagaatgcc   4800
cgtcctgttc aagttaaact aaaggattcc acctcctttc cctaccaaag gcagtacccc   4860
ctcagaccca aggcccaaca aggactccaa aagattgtta aggacctaaa agcccaaggc   4920
ctagtaaaac catgcagtaa cccctgcagt actccaattt taggagtaca gaaacccaac   4980
agacagtgga ggttagtgca agatctcagg attatcaatg aggctgttgt tcctctatag   5040
ccagctgtac ctagccctta tactctgctt tcccaaatac cagaggaagc agagtggttt   5100
acagtcctgg accttcagga tgccttcttc tgcatccctg tacatcctga ctctcaattc   5160
ttgtttgcct ttgaagatac ttcaaaccca acatctcaac tcacctggac tattttaccc   5220
caagggttca gggatagtcc ccatctattt ggccaggcat tagcccaaga cttgagccaa   5280
tcctcatacc tggacacttg tccttcggta ggtggatgat ttacttttgg ccgcccattc   5340
agaaaccttg tgccatcaag ccacccaagc gctcttcaat ttcctcgcta cctgtggcta   5400
catggtttcc aaaccaaagg ctcaactctg ctcacagcag gttacttagg gctaaaatta   5460
tccaaaggca ccagggccct cagtgaggaa cacatccagc ctatactggc ttatcctcat   5520
cccaaaaccc taaagcaact aaggggattc cttggcgtaa taggtttctg ccgaaaatgg   5580
attcccaggt atggcgaaat agccaggtca ttaaatacac taattaagga aactcagaaa   5640
gccaataccc atttagtaag atggacaact gaagtagaag tggctttcca ggccctaacc   5700
caagccccag tgttaagttt gccaacaggg caagactttt cttcatatgt cacagaaaaa   5760
acaggaatag ctctaggagt ccttacacag atccgaggga tgagcttgca acctgtggca   5820
tacctgacta aggaaattga tgtagtggca aagggttgac ctcattgttt acgggtagtg   5880
gtggcagtag cagtcttagt atctgaagca gttaaaataa tacagggaag agatcttact   5940
gtgtggacat ctcatgatgt gaatggcata ctcactgcta aaggagactt gtggctgtca   6000
gacaactgtt tacttaaatg tcaggctcta ttacttgaag ggccagtgct gcgactgtgc   6060
acttgtgcaa ctcttaaccc agccacattt cttccagaca atgaagaaaa gataaaacat   6120
aactgtcaac aagtaatttc tcaaacctat gccactcgag ggaccttttt agaggttcct   6180
ttgactgatc ccgacctcaa cttgtatact gatggaagtt cctttgtaga aaaaggactt   6240
cgaaaagtgg ggtatgcagt ggtcagtgat aatggaatac ttgaaagtaa tcccctcact   6300
ccaggaacta gtgctcagct agcagaacta atagccctca cttgggcact agaattagga   6360
gaagaaaaaa gggcaaatat atatacagac tctaaatatg cttacctagt cctccatgcc   6420
catgcagcaa tatggaaaga aagggaattc ctaacttctg agagaacacc tatcaaacat   6480
caggaagcca ttaggaaatt attattggct gtacagaaac ctaaagaggt ggcagtctta   6540
cactgccggg gtcatcagaa aggaaaggaa agggaaatag aagagaactg ccaagcagat   6600
attgaagcca aaagagctgc aaggcaggac cctccattag aaatgcttat aaaacaaccc   6660
ctagtatagg gtaatcccct ccgggaaacc aagccccagt actcagcagg agaaacagaa   6720
tggggaacct cacgaggaca gttttctccc ctcgggacgg ctagccactg aagaagggaa   6780
aatacttttg cctgcaacta tccaatggaa attacttaaa acccttcatc aaacctttca   6840
```

```
cttaggcatc gatagcaccc atcagatggc caaatcatta tttactggac caggcctttt   6900
caaaactatc aagcagatag tcagggcctg tgaagtgtgc cagagaaata atcccctgcc   6960
ttatcgccaa gctccttcag gagaacaaag aacaggccat taccctggag aagactggca   7020
actgatttta cccacaagcc caaacctcag ggatttcagt atctactagt ctgggtagat   7080
actttcacgg gttgggcaga ggccttcccc tgtaggacag aaaaggccca agaggtaata   7140
aaggcactag ttcatgaaat aattcccaga ttcggacttc cccgaggctt acagagtgac   7200
aatagccctg ctttccaggc cacagtaacc cagggagtat cccaggcgtt aggtatacga   7260
tatcacttac actgcgcctg aaggccacag tcctcaggga aggtcgagaa aatgaatgaa   7320
acactcaaag gacatctaaa aaagcaaacc caggaaaccc acctcacatg gcctgctctg   7380
ttgcctatag ccttaaaaag aatctgcaac tttccccaaa aagcaggact tagcccatac   7440
gaaatgctgt atggaaggcc cttcataacc aatgaccttg tgcttgaccc aagacagcca   7500
acttagttgc agacatcacc tccttagcca aatatcaaca agttcttaaa acattacaag   7560
gaacctatcc ctgagaagag ggaaaagaac tattccaccc ttgtgacatg gtattagtca   7620
agtcccttcc ctctaattcc ccatccctag atacatcctg ggaaggaccc tacccagtca   7680
ttttatctac cccaactgcg gttaaagtgg ctggagtgga gtcttggata catcacactt   7740
gagtcaaatc ctggatactg ccaaaggaac ctgaaaatcc aggagacaac gctagctatt   7800
cctgtgaacc tctagaggat ttgcgcctgc tcttcaaaca acaaccagga ggaaagtaac   7860
taaaatcata aatccccatg gccctccctt atcatatttt tctctttact gttcttttac   7920
cctctttcac tctcactgca ccccctccat gccgctgtat gaccagtagc tccccttacc   7980
aagagtttct atggagaatg cagcgtcccg gaaatattga tgccccatcg tataggagtc   8040
tttctaaggg aacccccacc ttcactgccc acacccatat gccccgcaac tgctatcact   8100
ctgccactct ttgcatgcat gcaaatactc attattggac aggaaaaatg attaatccta   8160
gttgtcctgg aggacttgga gtcactgtct gttggactta cttcacccaa actggtatgt   8220
ctgatggggg tggagttcaa gatcaggcaa gagaaaaaca tgtaaaagaa gtaatctccc   8280
aactcacccg ggtacatggc acctctagcc cctacaaagg actagatctc tcaaaactac   8340
atgaaaccct ccgtacccat actcgcctgg taagcctatt taataccacc ctcactgggc   8400
tccatgaggt ctcggcccaa aaccctacta actgttggat atgcctcccc ctgaacttca   8460
ggccatatgt ttcaatccct gtacctgaac aatggaacaa cttcagcaca gaaataaaca   8520
ccacttccgt tttagtagga cctcttgttt ccaatctgga aataacccat acctcaaacc   8580
tcacctgtgt aaaatttagc aatactacat acacaaccaa ctcccaatgc atcaggtggg   8640
taactcctcc cacacaaata gtctgcctac cctcaggaat attttttgtc tgtggtacct   8700
cagcctatcg ttgtttgaat ggctcttcag aatctatgtg cttcctctca ttcttagtgc   8760
cccctatgac catctacact gaacaagatt tatacagtta tgtcatatct aagccccgca   8820
acaaaagagt acccattctt ccttttgtta taggagcagg agtgctaggt gcactaggta   8880
ctggcattgg cggtatcaca acctctactc agttctacta caaactatct caagaactaa   8940
atggggacat ggaacgggtc gccgactccc tggtcacctt gcaagatcaa cttaactccc   9000
tagcagcagt agtccttcaa aatcgaagag ctttagactt gctaaccgct gaaagagggg   9060
gaacctgttt atttttaggg gaagaatgct gttattatgt taatcaatcc ggaatcgtca   9120
ctgagaaagt taaagaaatt cgagatcgaa tacaacgtag agcagaggag cttcgaaaca   9180
ctggaccctg gggcctcctc agccaatgga tgccctggat tctccccttc ttaggacctc   9240
```

```
tagcagctat aatattgcta ctcctctttg gaccctgtat ctttaacctc cttgttaact   9300

ttgtctcttc cagaatcgaa gctgtaaaac tacaaatgga gcccaagatg cagtccaaga   9360

ctaagatcta ccgcagaccc ctggaccggc ctgctagccc acgatctgat gttaatgaca   9420

tcaaaggcac ccctcctgag gaaatctcag ctgcacaacc tctactacgc cccaattcag   9480

caggaagcag ttagagcggt cgtcggccaa cctccccaac agcacttagg ttttcctgtt   9540

gagatggggg actgagagac aggactagct ggatttccta ggctgactaa gaatccctaa   9600

gcctagctgg gaaggtgacc acatccacct ttaaacacgg ggcttgcaac ttagctcaca   9660

cctgaccaat cagagagctc actaaaatgc taattaggca aagacaggag gtaaagaaat   9720

agccaatcat ctattgcctg agagcacagc aggagggaca atgatcggga tataaaccca   9780

agtcttcgag ccggcaacgg caaccccctt tgggtcccct ccctttgtat gggagctctg   9840

ttttcatgct atttcactct attaaatctt gcaactgcac tcttctggtc catgtttctt   9900

acggcttgag ctgagctttc gctcgccatc caccactgct gtttgccgcc accgcagacc   9960

cgccgctgac tcccatccct ctggatcatg cagggtgtcc gctgtgctcc tgatccagcg  10020

aggcacccat tgccgctccc aatcgggcta aaggcttgcc attgttcctg catggctaag  10080

tgcctgggtt catcctaatt gagctgaaca ctagtcactg ggttccatgg ttctcttctg  10140

tgacccacag cttctaatag agctataaca ctcaccgcat ggcccaaggt tccattcctt  10200

gaatccataa ggccaagaac cccaggtcag agaacacgag gcttgccacc atcttgggag  10260

ctctgtgagc aaggaccccc aagtaaca                                     10288
```

<210> SEQ ID NO 7
<211> LENGTH: 6818
<212> TYPE: DNA
<213> ORGANISM: Homo sapiens

<400> SEQUENCE: 7

```
gcaactccct ttgggtctcc tctcattgta tgggagctct gttttcactc tattaaatct     60

tgcaactgca cactcttctg gtctgtgttt gttatggctt gagctgagct tttgctggct    120

gtccaccact gctgtttgct gccgtcgcag accccttgct gactcccacc cctgcggatc    180

tggcagggtg tctgctgcgc tcctgatcca gccaggcacc cactgctgct cccaatcagg    240

ctaaaggctt gccattgttc ctgcatggct aagtgcccgg gttcgtgcta attgagctga    300

acactagtcg ctgggttcca cagttctctt ccgtgaccca cagcttctaa tagagctata    360

acactcactg catggcccaa cattccattc cttggaatct gtgaggccaa gaaccccccgg   420

tcagagaaca agaagcttgc caccatcttg gaagcagccc gccaccattt tgggagctct    480

aagaacaagg accccccagt aacattttgg tgaccacgaa gggacctcca aagcagtgag    540

taatattgaa ccacttccgc ttgctattct gtcctaacct tccttagaat tggaggaaaa    600

taccgggcac ctgtcggcca gttaagaacg attagcgtgg ccgccagact taagactctg    660

gtgtgaggct gtctgggaaa gggctttcta acaaccccca acccttccgg gttgggagct    720

ttggtctgcc tggaaccagc ttccactttc aattttcctg ggaatccaa gggctgacta    780

gaggcagaaa gctgtcatcc cgaactcctg gcattagaca gttgagatcg tggcgcagcc    840

agaagtctct actcaacagt cacccatgcg tgcaccccta cctttccttc taacccatac    900

ctcccgggtc ccaaccatga ctttcttgaa agtgtagccc ctaaattctc tttacctcta    960

aatctacttc ttctcatccc tgcttcctag gtactaatgg ttcagacttt catttcctct   1020
```

```
agcaagttct atctccagag ggatctaagg aagggatcta tgctgtgtcc ttaggcccct   1080
aggctatgaa cccagagagt cttctccctg ttatctctcc ccatttaggc atacagctct   1140
caacatggac agttatgtgg gacccattcc ctaccaccct tgccagggcc ccaagttttc   1200
aaagggctag aagaaaaaag agagaaagag agagagaggc agaggggaga gaaagagaga   1260
gagacaaaga gggagtcaaa gagagataga aagagaaaga tagaactagt aaagaaaaaa   1320
agtatgcccc attcctttaa aagccagggt aaatttaaaa cctataattg ataattgaag   1380
gtcttctcca tgaccctata acactccaat accaccttgt tttcagtgta aacaagggtg   1440
tagcccgaaa acactgagac cactgacaac ccatagcctt cctatcaaaa atccttaacc   1500
caggaaccca tggatggccc aaatgcattc aatctgtagc agcaactgct ttgctaacag   1560
aagaaagtag aaaagtaact tttagagaaa acctcattgt gagcacacct caccagttca   1620
gaattattct aagtcaaaaa agcaaaaagg tagcttacta actcaaaaat cttaaagtat   1680
ggggttattc tgttagaaaa aggtgattta acattaacca ctgaaaattc ccttaaccca   1740
gcaggtttcc taatgggatt taaatcttca ttaccataca aaggtccgac cagacccagc   1800
aggaactccc tttaggacag gatgatagat ggttcctcct gggtgattga gggggtgaaa   1860
aaccacaatg ggtgttcagt aattgatagg gagactcttg tggaaggaga gttaggaaaa   1920
ttgcctaata attggtctgc tcaaatgtgc gagctgtttg cactcagcca agccttaaag   1980
tacttacaga atcaaaaaga ctctatctca atcctgactc aaaatgttac ctacaccatc   2040
tctgacatga atttgcataa gaactgttgt ttatgggaat gcatcttgat ggggcagctg   2100
ggttgttatg aaatactcag gaacccagcc caggtctaga attcacctct gagcgcaaag   2160
gcaatgttgg ccatgctggt aaaggaccac tagaatccag gagcctggac ccctttcttt   2220
gtggtcaaga aaggcgggaa aacaggtgca ggactgctac atcagagagc ataacaaatc   2280
cgataagcag agttccatga gtggttaagc accctggaaa ggaactcacc tctgagtgca   2340
aaggcaatgt taggcacacc agtaaaggac cactagaatc cagcagccca gacccctttc   2400
tttgtgatca agaaaggcgg gaaaaggggt gcaggactgc tacatcagtg agcgtaacta   2460
atctgataag cagaagtcca tgggtggtta cgcaccctgg aaaggaataa gcattaggac   2520
cacagaggac actctaagac taatgctcat tggaaaatga ctaggggtgc tggcatccct   2580
atgttttttt ttcagatggg aaacattccc cccaaggcaa aaacgcccat aagatatatt   2640
ctggagaatt cggcccagag tgtatgtatc ttttttccct gtcagacttg aagcaaacct   2700
aggtaaatta tcagatagcc ctgatggcta tattgatgct ttacaagggt taggacaatc   2760
ctttgatcta acatggagag atatactgtt actgctagat cagacactaa tcccaaatga   2820
aagaagtgcc accataactg cagccagaga gtttgatgat ctctggtatc tcagtcaggt   2880
caatgatagg atgacaacag aagaaagaaa acaattcccc acaggccagc aggcagttcc   2940
cagcgtagac cttcattggg acacagaatc agaacatgga gattggtgcc gcagacattt   3000
actaacttgc gcgctagaag cactaaggaa aactaggaag aagcctatga attattcaat   3060
gatgtccact ataacacagg gaaaggaaga aaatcctact gcctttctgg agagactaag   3120
ggaggcattg agaaagcata cctctctgtc acctgactct attgaaggcc aactaatctt   3180
aaaggataag ttttccactc agtcagctgc agacattaga aaaaaacttc aaaagtctgc   3240
gttaggccgg gagcaaaact tagaaaccct attgaacttg gcaacctcag ttttttatga   3300
tagagatcag gaggatcagg tggaatggac aaatgagatt ttaaaaaaag gccaccactt   3360
tagtcatggc cctcaggcaa gcagactttg gacactctgg aaaagggaaa agctgggcaa   3420
```

```
atcgaatgcc taataagact tgcttccagt gtggtctaca aggacacttt aaaaaagatt   3480

gtccaaatag aaataagcca cccccctcgtc catgctcctt atgtcaaggg aatcactgga   3540

aggcctactg ccccagggga tgaaggtcct ctgagtcaga agccactaac cagatgattc   3600

agccccagga ctcagggtgc ccagggcaag cgccagccta tgccatcacc ctcacagagc   3660

cctgggtatg cttgaccatt gagggtcagg aggttaacta tctcctggac actggcgtgg   3720

ccttctcagt cttactctcc tgtcccggac aactgtcctc cagatctgtc actatccgag   3780

ggtttctacg acagccagcc actagatact tctcccagcc actaagttgt gactggggaa   3840

ctctactctt ttcacatgtt tttctaatta tgcctgaaag ccccactcct ttgttaggga   3900

aagacattct agcaaaagca ggggccatta tacacctgaa cataggagaa ggaacacctg   3960

tttgttgtcc cctgcttgaa gaaggaatta atcctgaagt ctggacaaca gaaggacaat   4020

acagatgagc aacaaatgcc tgtcctgttc aagttaaact aaaggattat gcctcctttc   4080

cctaccaaag gcagtacccc cttagacccg aggcccaaca aggactccaa aagattgtta   4140

aggacctaaa agctcaaagc ctagcaaaac catgcagtag cccctgcaat actccaattt   4200

taggagtaca gaaaaccaac agacagtgga ggttagtgca agatctcagg attatcaatg   4260

aggctgttgt tcctaaccct tatactctgc tttcccaaat accagaagaa gcagagtggt   4320

ttacagtcct ggaccttaag gatggctttt tctgcatccc tgtacatcct gactctcaat   4380

tcttgtttgc ctttggagat ccttcgaacc caatgtctca actcagcttg actgttttac   4440

cccaagggtt cagggatagc cccccatctag ttggccaagc attagccgag ccagttctcc   4500

tacctggaca ctcttgtcct ctggtacatg gatgatttat ttttagctgc ccgttcagaa   4560

accttgtgcc atcaagccac ccaagtgctc ttaaatttcc tcgccacctg tggctacaag   4620

gtttccaaac caaaggctca gctctgctca cagcaggtta aatacttagg gctaaaatta   4680

tccaaaggca ccagggccct cagtgaggaa tgtatccagc ctgtattggc ttatcctcat   4740

cccaaaaccc taaagcaact aagagggttc cttggcataa caggtttctg ccaaatgtgg   4800

attcccaggt acggtgaaat agccaggcca ttatataccc taattaagga aactcagaaa   4860

gccaacaccc atttattaag atggacacct gaagcagaag cagctttcca ggccctaaag   4920

aaggccctaa cccaagcccc agtgttaagc ttgccaacgg ggaagacttt tctttatatg   4980

tcacagaaaa aacaggaata gctctaggag tccttagaca ggtccaaggg atgagcttgc   5040

aacctgtggc atacctgagt aaggaaattg atgtagttgc aaagggttga cctcattgtt   5100

tacaggtagt ggcggcagta gcagtcttag tatctgaagc agttaaaata atacagggaa   5160

gagatcttac tgtgtggaca tctcatgatg taaacggcgt actcacttct aaaggagact   5220

tgtggctgtc agacaaccgt ttacttaaat atcaggctct attacttgaa gggccagtgc   5280

tgcgactgcc cacttgttca actcttaacc cagccacatt tctttcagac aatgaagaaa   5340

agatagaaca taactgtcaa caggtgattg ctcaaaccta cggcgctcga ggggaccttc   5400

tagaggttcc cttgactgat cccaacctca acttgtatac tgatggaagc tcctttgtag   5460

aaaaaggact ttgaaaggtg gggtatgcag tggtcagtga taatggaata cttgaaagta   5520

attccttcac tccaggaact agtgctcagc tggcagaact aatagccctc actcaggcac   5580

tagaattagg agaaggaaaa agggtaaata tatatgcaga ctctaagtat gcttacccag   5640

tcctccacgc ccacacagca atatggagag ataggaaatt cctaacttct gagggaacac   5700

cgatcaaaca tcaggaagcc attaggagat tattattggc tgtacagaaa cctaaagagg   5760
```

```
tggcagtctt acactgctgg ggtcatcaga aaggaaagga aaaggaaata gaaaggaacc   5820

accaagtgga tattgaagcc aaaagagcca caaggcaggc cctccattag aaatgcttat   5880

agaaggatcc ctagtatggg gtaatcccct ccgggaaacc aagccccagt actcagcagg   5940

agaaatagac acgaggacat agtttcctcc cctcaggatg gctagccacc gaaaaaggga   6000

aaatactttt gcctgcagct aatcaatgga aattacttaa aacccttcac caaacctttc   6060

acttgggcat ggatagcatc tatcagatgg ccaatttatt atttactgga ccaggccttt   6120

tcaaaactat caagcagata gtcagggcct gtgaaatgtg ccaaagaaat aatcccctgc   6180

acttcaagcc atacatttca atccctgtat ctttaacctc ctgttgtttg tctcttccag   6240

actcaaagct gtaaaactgc aaatggttcc tcatatggag ccccagatgc agtccatgac   6300

taagatctac cacagagccc tagaccggcc tgttagccca tgctccgatg ttgatgacat   6360

caaaggcaca ccttccgagg aaatctcaac tgcacgaccc ctactaagcc ccaattcagc   6420

aggaagcagt taagagcagt cgttggctaa catccccaat agtatgtggg ttttcctgtt   6480

gagagggggg actgagagac aggactagct ggatttccta ggccaactaa gaatccctaa   6540

gcctagttgg gaaggtgacc gcatccacct ttaaacacgg ggcttgcaac ttagctcaca   6600

cccgaccaat caggtagtaa agagagctca ctaaaatgct aattaggcaa aaacaagagg   6660

taaagaaata gccaatcatc tatcgcctga gagcacagtg gggagggaca atgatcggga   6720

tataaaccca ggcattcggg ccggcaacgg caacccccat tgcgtcccct cccattgtat   6780

gggagctctg ttttcattct attaaatctt gcaactgc                           6818
```

<210> SEQ ID NO 8
<211> LENGTH: 7073
<212> TYPE: DNA
<213> ORGANISM: Homo sapiens

<400> SEQUENCE: 8

```
gcaaccccct ttgggtctcc tccctttgca taggagctct gttttcactc tattaagtct     60

tgcaactgca ctcttctggt ccgtgtttct taccgcttga gctgagcttt ccctcactgt    120

ccaccactgc tgttttgcca ccgtcacagg cccaccgctg acttccattc ttctggatct    180

agcaggctgt ccactgtgct cctgatccag cgaggcgccc attgccgctc ccgattgggc    240

taaaggcttg ccattgttcc tgcatggcta cgtgcctggg ttcatcctaa tcaagccgaa    300

cactagtcac tgggttccac ggttctcttc catgacccac gacttctaat agaactataa    360

cactcacctc atggcccaag attccattcc ttggaatcca tgaggccaag aaccccaggt    420

cagagaacac gaggcttgcc accatcttgg aagtggcccc accaccatct tgggagctct    480

gggagcaagg acccccggta acattttggc gaccacaaag ggacatccaa agtggtgagt    540

aatattggac cactttcact tgctattctg ttctatcctt ccttagaact ggaggaaaat    600

accaggcaca ggcacctgtc agccagttaa aaacaattag cgtcgccgcc acacttaaga    660

ctcaggtgtg aggctatctg ggaaaagact ttctaacaac ccccaaccca tctagtgggg    720

atgttggtct gcctggagac agcttccact ttcaattttc ttggggaagc cgagggctca    780

ctagaggcag acagctgttg tcccaaactc cgggcagtag ccggttgaga tcatggtgca    840

gccaggagtc tctactcagc agtcgccgat gcatgtgccc ctaccttccc ttctgaccca    900

tacatcctga gtcccgactg tgactttctt gaaagtgtag ccccaaaatt ctccttacct    960

ctgaatctac ttcctctgat ccctgcctcc tgggtactaa tgattcagac tttcatttcc   1020

tctagcaagt tgtgtctcca aagggatcta aggaggctct acgctgcatc cttaggcacc   1080
```

```
taggctataa cccaaggagt cttatccctg gtgtccctcc cgatttgggt atacaactct   1140
caacatgggc agttatgtag gacccattcc ccaccacact tgccagggcc ccaagtttgt   1200
aatggctaag agagagacac agagagagag agagagatgg agagagagac aaggagggag   1260
tcaaagagaa aaagaaagaa aaagaaatag tagaaaaaaa agtgtgccct attcctttaa   1320
aagccagggt aaatttaaaa cctgtaattg ataattgaag gtcttctccg tgaccctgta   1380
acactccaat gccattttgt tgtcagtgta aataagggca tagcccaaaa gcactgaggt   1440
cactgacaac ccgtagcttt cccatcaaaa atccttaacc cagtaatccg cggatgggcc   1500
aaatgcattc agtcggtagc agcaaccgct ttgctaaaag tagaaaagta acttttagag   1560
gaaacctcat tgtgagcgca cacctcacca gttcagaatt attctaagtc aaaaaaaaaa   1620
aaagcaaaaa ggtaacttac taactcaaaa atcttaaagt ataggtctat catattagaa   1680
aagggtaatg taactccaac cactgataat tcccttaacc cagcagattt cctaacaggg   1740
gatttaaaac ttaattacca tacaaaggtc ccaccagacc taggaggaac tcccttcagg   1800
acaggacgat aaacggttcc tcccaggtga ttgaggaaaa aaaccacaat gggtattcag   1860
taattgatac agagactcat gtggaagcag ttagaaaaat tgcctaataa ttggtctcct   1920
caaacgtgta agctgtttgc actcagccaa gccttaaagt acttacagaa tcaaaaagac   1980
tctgaatcct gactcaaaag gtttgctaca ccctctgtga aacaaatttg cataagaact   2040
gttgtttatg ggaaggcatc ttgatggggc agctgggttg ttatgaaata ctcaggaccc   2100
cagcccggct ctaggactca cccctgagcg caaaaggcaa tgttgggcac gctggtaaag   2160
gaccactaga atccagcagc ccggacccct ttctttgtgg tcaagagagg cgggaaaaca   2220
ggtgcaggac tgctacatca gtgagcataa ctaatccagt aagcagaggt ccatgggtgg   2280
ttatgcaccc tggaaaagaa tacgcattag gcccttagag gatgctctag gactaatgct   2340
catcggaaaa tgactagggg tgctgacatc cctatgttct tttttcagat gggaaacgtt   2400
cctcccaccc caaggcaaaa aacaccccta agatgtattt tggagaatta ggaccaattt   2460
gaccctcaga cactaagaaa gaaatgactt acattcttct gcagtaccat gatatcctct   2520
tcaaggggga gaaacctggc ctcctgagag aagtataaat tataacacca tcttacagtg   2580
agacctcttc tgtagaaagg agggcaaatg gagtgaagtg caaactttcc tttcattaag   2640
agacaactcg caattatgta aaaagtgtga tttatgccct acagaaagcc ctcagtctac   2700
ctccctatcc cagggtcccc ccgattcctt tcccaactaa taaggacccc ccttttaccc   2760
aaatggtcca aaggagatag atgaagggat aaacaatgaa ccaaacagtg ccaatattcc   2820
ctgattatgc cccctccagg cagtgggagg aggagaattc ggcccagcca gagtgcatgt   2880
accttttttt ttctctcaga cttaaagcaa attaaaatag acctaggtaa attctcagat   2940
aaccctgatg gctatattga tgttttacaa gggttaggac aatcctttgc tctgacatgg   3000
agagatataa tgttactgct aaatcagaca ctaaccccaa atgagagaag tgtcaccata   3060
gctgcagccc aagagtttgg caatctctgg tatctcagtc aggtcaatga taggatgaca   3120
acagaggaaa gggaatgatt ccccacaggc cagcaggcag ttctcagtgt agaccctcac   3180
tgggacacag aataagaaca tggagatcgg tgccgcagat atttgctaac ttgcgtgcta   3240
ggactaagga aaactaggaa gaagcctatg aattattcag tgatgtccac tataacacag   3300
ggaaaggaag aaaatcatac tgcctttccg gaaatactaa gggaggcatt gaggaagcat   3360
acctctctgt cacctgactg tattgaagtc caactaatct taaaggatat gtttatcact   3420
```

```
cagtcagctg cagacattag aaaaaacttc aaaagtccac cttaggccca gagcaaaact   3480

tagaaaccct attgaacttg ttaacctcag ttttttataa tagagatcag gaggagcagg   3540

cggaacagga caaacaggat taaaaaaaga ccaccgcttt agtcatggcc ctcaggcaag   3600

tggactttgg aagctctgga aaagggaaaa gctgggcaaa ttgaatgcct aatagggctt   3660

gcttccagtg tggtctacaa ggacacttaa aaaaagattg tccaagtaga aataagctgc   3720

cccttcgtcc atgcctctta tgtcaaggga atcactggaa ggcccattgc cccaggggag   3780

gaaggtcctc tgagtcagaa gccactaacc agatgatcca gcagcaggac taagggtgcc   3840

cagggcaagc cccagcccat gccatcaccc tcacagagcc ccgggtatgc ttgaccattg   3900

agggccagga ggttaactgt ctcctgaaca ctggcacagc cttctcagtc ttactttcct   3960

gtcccggaca actgtcctcc agatctgtca ctatctgagc ggtcctagga cagccagtca   4020

ctagatattt ctcccagcca ctaagttgtg actggggaac tttactcttt tcacatgctt   4080

ttctaattat gcctgaaagc cccactcctt tgttagggag agacattcta gcaaaagcag   4140

gggccattat acatctgaac ataggagaag gaacacccgt ttgttgtcac ctgcttgagg   4200

aaggaattaa tgctgaagtc tgggcaacag aaggacaata tggatgagca aagaatgccc   4260

atcctgttca agttaaatta aaggattccg cctcctttcc ctaccaaagg caataccccc   4320

ttagacccga ggcccaacaa ggactccaaa agattgttaa ggacctaaaa gcccaaggcc   4380

tagtaaaacc atgcaatagc cctgccata ctccaatttt aggagtaagg aaacccaacg   4440

gacagtggag gttagtgcaa gaactcagga ttatcaatga ggctgttgtt cctctatacc   4500

cagctgtacc taacccttat acagtgcttt cccaaatacc agaggaagca gagtggttta   4560

cagtcctgga ccttaaggat gccttttct gcatccctgt acgtcctgac tctcaattct   4620

tgtttgcctt tgaagatcct ttgaacccaa cgtctcaact cacctggact gttttacccc   4680

aagggttcaa ggatagcccc catctatttg gccaggcatt agcccaagac ttgagccaat   4740

tctcatacct ggacactctt atccttcggt atggggatga tttaatttta gctacccatt   4800

cagaaacgtt gtgccatcaa gccacccaag tgctcttaaa tttcctcgct acctgtggct   4860

acaggtttcc aaacgaaagg ctcagctctg ctcacagcag gttaaatact tagggctaaa   4920

attatccaaa ggcaccaggg ccctcagtga ggaacgtatc cagcctatac tggcttattc   4980

tcatcccaaa accctaaagc aactaagagc attccttggc ataacaggct gctgctgaat   5040

atggattccc aggtacagtg aaatagccag gccattatac acactaatta aggaaactca   5100

gaaagccaat acccatttag taagatggac accttaagca gaagcggctt tccaggcctt   5160

aaagaaggcc ctaacccaag ccccagtggt aagcttgcca acagggcaag acttttcttt   5220

atatgtcaca gaagaaacag gaatagctct aggagtcctt acacaggtct gagggatgag   5280

cttgcaaccc atggcatacc tgagtaagga aactgatgta gtggcaaagg gttggcctca   5340

ttgtttacgg gtagtggcag cagtagcagt cttagtatct gaagtagtta aaataataca   5400

gggaagagat cttactgtgt gaacatctca tgatgtgaat ggcatagtca ctgctaaagg   5460

agacttgtgg ctgtcagaca actgtttact taaataccag gctctattac ttgaagggcc   5520

agtgctgcga ctgtgcactt gtgcaactct taacccagac acatttcttc cagacaatga   5580

agaaaagata gaacataact gccaacaagt aattgctcaa acctatgcca ctcgagggga   5640

ccttttagag gttcccttga ctgatcccaa cctcaacttg tatactgatg gaagttcctc   5700

tgtagaaaaa ggactttgaa aagtggggta tgcagtggtc agtgataatg gaatacttga   5760

aagtaatccc ctcactccag gaactagtgc tcagctggca gaactaatag ccctcactcg   5820
```

```
ggcactagaa ttaggagaag agaaaagggt aaatatatac agactctaag tatgcttacc   5880
tagtcctcca tgcccatgca gcaatatgga gagaaaggga attcctaatt tccaagggaa   5940
cacctatcca acatcaggaa gccattagga gattactatt ggctgtacag aaacataaag   6000
aggtggcaat cttacactgc cggtgtcacc agaaaggaaa ggaaagggaa atagaaagga   6060
accaccaagc ggatattgaa gccaaaagag ccgcaaggca ggaccctcca ttagaaatgc   6120
ttatagaagg accccctagta tggggtaatc ccctccagga aaccaagccc cagtactcag   6180
aagaagaaat agaatgagga acctcacaag cacatagttt cctcccctca ggatggctag   6240
ccactgaaga aggaaaaata cttttgcctg cagctaacca atggaaatta cttaaaaccc   6300
ttcaccaaac atttccctta ggcattgata gcacccatca gatggccaaa ttattattta   6360
ctggaccagg ccttttcaaa actatcaagc agatagtcag ggcctgtaaa gtgtgccaaa   6420
caagtaatcc cctgcactgc aggccataca tttcaatccc tgtatcttta acctccttgt   6480
taagtttgtc tcttccagaa tcaaagctgt aaaactacaa atagttcttc aaatggagcc   6540
ccagatgtag tccatgacta agatctaccg cggacccctg gacaagcctg ctagcccatg   6600
ctctgatgtt aatgacatgg aaggcacccc tcccgaggaa atcgcaactg cacaacccct   6660
attacacccc aattcagcag gaagcagtta gagcattcat cagccaacct ccccaacagc   6720
acttgggttt tcctattgag agggggtact gagagacagg actagctgga tgtcctaggc   6780
tgactaagaa tccctaagcc tagctgggaa ggtgaccaca tccaccttta aatacggggc   6840
ttgcaaccta gctcacaccc aacagatcag agagctcgtt aaaatgctaa ttaggcaaaa   6900
acaggaggta aagaaatagc caatcatcta ttgcctgaga gcacagcagg agggacaagg   6960
attgggatat aatcccaggc attcgagctg gcaacagcaa ccccctttgg gtcccctccc   7020
tttgtatggg agctgttttc actctatttc actctattaa atcttgcaac tgc          7073
```

<210> SEQ ID NO 9
<211> LENGTH: 5068
<212> TYPE: DNA
<213> ORGANISM: Homo sapiens

<400> SEQUENCE: 9

```
gcaacctcct ttgagtcccc tccctttgta taggagctct gttttcactg tgtttcactc     60
tattaaatct tgcaattgca ctcttctggt ccatatttgt cacggcttga gctgagcttt    120
cacttgccgt ccaccactac tgtttgctgc tgtcacagac ccgccgctga ctcccatccc    180
gctgctgact cccatccctc cggatccggc agggtgtccg ctgtgctcct gatccagcaa    240
gactcccatt gccactcccg atagtgctaa aggcttgcca ttgttcctgc atggctaagt    300
gcctgggttc gtcctaatcc agctgaacac tagtcactgg gttccacggt tctcttccat    360
gacccgcggc ttctaataga gctataacac tcaccacatg gcccaatatt ccattccttg    420
gaatccgtga ggccaagaac cccaggtcag agaacacgag gcttgccacc atcttggaag    480
cagcctgcca ccatcttgga agtggctcac caccgtcttg ggagttctgt gaacaaggac    540
ccctggtaac attttggcga ccacgaaggg acatccaaag ctgtgagtaa tattggacca    600
ctttcgcttg ctattctgtt ctatccttag aactggagga aaatactggg cacctgtcgc    660
cagttaaaaa tgattagcat ggccgccgga cttaagactc aggtgtgagg ctatctggga    720
aagggctttc taacaacccc caagccttct gttgggaact ttggtctgcc tggagccagc    780
ttccactttc aattttcttg gggaagccaa gggctgactg gaggcagaaa gctgttgtcc    840
```

-continued

```
cgaactcccg gcagtagccg gttgagatca tggcgcagcc agaagtctct actcggcagt    900
cgcccatgcg tgcgccctta cctttccttc tgaattatac ctccggggtc ccgactccga    960
ctttcttgag agtttagccc caaaattctc cttacctctg aatctacttc ctttgatccc   1020
tgcctcctgc ctcctaggta ctaatagttc agactttcat ttcctctagc aagttgtgtc   1080
tccaaaggga tctaaggagg ctctatgctg tgtccttagg cacctaggct ataacccagg   1140
gagtcttatc cctggtatcc ctcccgattt aggtatacag ctcttgacat gggcagttat   1200
gtgggacctg ttccccacca cccttgtgag ggccccaagt ttgtaatggc taagaaagag   1260
agacggagag agagagagac ggagaaagag acaaagaggg agtcaaagag aaaaagaaag   1320
aaaaagatag aaatagttaa aaaaaaaaaa aagtgtgccc tattccttta aaagccaggg   1380
taaatttaaa acctgtaatt gataattgcc actttgttgt cagtgtaaat aagggcgtag   1440
caaatcctta acccagtaac ccgcggatag gccaaatgca ttcagtcggt agcggcaaca   1500
gctttgctaa aagtagaaaa gtaactttta gaggaaacct cattgtgagc acacctcacc   1560
agttcagagt tattctaagt aaaaaaaaaa aaaaaaaaaa aagcaaaaag gtagcttact   1620
aactcaataa tcttaaagta tggggctact atgctagaaa agggtaatgt aactccaacc   1680
actgataact cccttaaccc agcagatttc ctaacagggg atttaaatct taattaccac   1740
acgaaggtcc gaccagacct aggaggaact cccttcagca caggacgata gatggttcct   1800
cccaggtgac tgaggaaaaa actacaatgg gtattcagta attggtatgg agactcttgt   1860
ggaagcagag ttaaaaattt gcctaataat tggtctcctc aaatgtgcga gctgtttgca   1920
ctcagccaag ccttaaagta cttacagaat caaaagacta tctcaatcct gactcaaaag   1980
gttagctaca cagtctctga aatgaatttg cagaagaact gttgtttatg ggaatgcatc   2040
ttgatggggc agctgggttg ttatgaaata ctcaggaacc cagcccagct ctaggactca   2100
ccgctgagcg caaaggcaat gttgggcacg ctggtaaagg accactagaa tccagcagcc   2160
caggcccctt tctttgtggt caagaaaggc aggaaaagga gtgcagaact gctacattgg   2220
tgagcgtaac taatccaata agcagaggtc catgagtggt tatgcacgct ggaaaagaat   2280
aagcattagg cccttagagg atgctctagg actaatgctc atcggaaaat gactaggggt   2340
gctggcatcc ttatgttctt tcttcagatg ggaaacgttc cccccaaggc aaaagcgccc   2400
ctaagatgta ttctggagaa ttagaaccaa tttgaccctc agatgtcaag aaagaaacga   2460
cttatattct tctgcagtac tgcctggcca cgatatcctc ttcaaggggg agaaacctgg   2520
cctcctgagg gaagtacaaa ttataacacc atcttacagc tagacctctt ttgtagaaaa   2580
gaaggcaaat ggagtgaagt gccatatgtg caaactttct tttcattaag agacaactca   2640
caattatgta aaaagtgtgg tttatgtctt acaggaagcc ctcagagtct acctccctat   2700
cccagcattc ccccgactcc ttccccaact aataagcacc acccttgaac ccaaacagtc   2760
caaaaggaga tagacaaaca ggtaaacaat gaaccaaaga gtgtcagtat tccccgatta   2820
tgccccttcc aagcagtggg aggaggagaa ttcggcccag ccagagtgca tgtacctttt   2880
tctctctcag acttaacgca aattaaaata gacttaggta aattctcaga taaccctgat   2940
ggctacattg atgttttaca agggttaggg caatcctttg atctgacatg gagagatata   3000
atgttactgc taaatcagac actaacccca aatgagagaa gtgccgccgt aactgcagcc   3060
cgagagtttg gtgatctctg gtatctcagt caggtcaatg ataggatgac aacagagaaa   3120
agagaacgat tccccacagg ccagcaggca gtttccagtg tagaccctca ttaggacaca   3180
gaatcagaac atggagattg gtgccacaga tatttgctaa cttgagtgct agaaggacta   3240
```

```
aggaaaacta ggaagaagcc tatgaattat tcagtgatgt ccactataac acaaggaaag   3300

gaagaaaatc ctactgcctt tctggagaga gtaagggagg cattaaggaa gcatacctcc   3360

ctgtcacctg actctattga aggccaacta atcttaaagg ataagtttgt cactcagtta   3420

gctgcagaca ttagaaaaaa acttcaaaag tccgacttag gcctggagta cggctgagtg   3480

cccaatttgg cagcaggcaa gaccaacact gagcccttca tatggcacca tgctttgtgg   3540

tgatcagcca actacttgat ggcaggttga ttatattgga catctttcat cagagaaatg   3600

gcagtggttt gtccttcctg gaatagacac ttattctcga tatgggtttg tctatcctgc   3660

aggcaatgct tctgccagga gtaccatctg tggactcatg gaaagcctta tccaccatca   3720

tggcattcca cacagcattg cctctaaaca aggcacttat tttatagcta aggaagtgtg   3780

gcagtgggct catgctcatg gaattcactg attgtatctt gttgcccatt atcttaaagc   3840

agctggattg atagaacagt ggaaaggcca tttgaaatca caattacacc accaactagg   3900

tgacaatact ttgcagggct cggcaaagtt ctcttgaagg ctgagtatgt cctgaatcag   3960

catccaatat atggtactgt ttccctcata gccagcattc acaggcctaa gaatcaaggg   4020

gtagaagtag aagtggcacc actcaccatc actcctagtg acccactagc aaaaatttta   4080

cttccagttc cccaacatt atgttctgct ggccttagtt ccagagggaa gaattctgcc   4140

accagtcgac acaagaatga taccattaaa ctgaaagtta aaattgccac ctggccactt   4200

tgggctcctc ccacctctaa gtcaacaggt caagaaagga gttacagtgt tgacttgggt   4260

gattgacctg gactatcaag atgaaatcag gttactactc cacagtggag gtaaggaaga   4320

atatgtgtgg aatacaggag atcccttagg ccgtctttta gtactaccat gccctgtgat   4380

taaggtcagt ggaaaactac aacaatccaa tctaggcagg actacaaatg gcccagactc   4440

ttcaggaatg aagggttggg tgacttcacc aggtaaaaaa ataacagcct gctgaggtgc   4500

tagctgaagg caaagggaat acagaatggt tagtagaaaa aggtagtcat caataccagc   4560

tatgaccaca agaccagttg cagaaatgag acctgtaatt gtcatgtgga tttcctcctt   4620

acatgtttgt gcatgtatac acttctacta agaaaatacc tttatttatt tcctttgctt   4680

ttcccttatc aagtgacatt attaacttca tatcagcagt taagtgttat taactttatg   4740

taatagcatt tcggttaata attcacttct ggttgtatga aggatagccg tattaagtta   4800

ggtgtaatta tgacatcatt attgtcttta tttgaagatt atgtgtaatt tcaggagatg   4860

tgtatgggtt caagttgaca agggatggac ttgtgatggc taatgttgag tgtcaacttg   4920

actgaggatg caaagtattg ttcctgggtg tgtctgtgag ggtgttgcca aaggagatta   4980

acatttgtgt cagtgaactg ggagatgcag acccacccgc aatctgggtg agcaccatgt   5040

aatcagctgc cagagcagct agaataaa                                       5068
```

<210> SEQ ID NO 10
<211> LENGTH: 535
<212> TYPE: DNA
<213> ORGANISM: Homo sapiens

<400> SEQUENCE: 10

```
gcaaccccct ttgggtcccc ttcccttgta tgggagctct gttttcactc tatttcactc     60

tattaaatct tgcaactgca ctcttctggt ccatgtttgt tacggctcga gctgagcttt    120

ggctcgccat ccaccactgc tgtttgccgc cgtcgcacac ctgctgctga ctcccatccc    180

tccggatcca gcagggtgtg tccgctgtgc tcctgatcca gcgaggtgcc cattgccgct    240
```

```
cctgattgga ctaaaggctt gccattgttc ctgcacggct aagtgcccgg gttcgtccta    300

atccagctga acactagtca ctgggttcca cggttctctt ccttgaccca cggcttctaa    360

tagagctata acactcaccg catggcccaa gattccattc cttggaatct gtgaggccaa    420

gaaccccagg tcagagaaca cgaggcttgc caccatcttg gaagcggcct gccaacatct    480

tggaagtggc tcgccaccat cttgggagct ctgtgagcaa ggacccctgg taaca         535
```

```
<210> SEQ ID NO 11
<211> LENGTH: 6905
<212> TYPE: DNA
<213> ORGANISM: Homo sapiens

<400> SEQUENCE: 11

gctaccctct ttgggtcccc tccctttgta tgggagctct gttttcactc tattcaatct     60

tgcaactgca ctcttctggt ccgtgtttgt tacagcttga gctgagcttt cgctcgcctt    120

ccaccactgc tgtttgccgc catcgcagac ctgccgtgct gacttccatc cctctagatc    180

tggcagggtg tccgctgtgc tcttgatcca gcgaggcgcc cattgccgct cccgattggg    240

ctaaaggctt gcaattgttc ctgcacgcta agtgcctggg ttcatcctca tcaagctggg    300

ttccacggtt ctcttcatga cccgcagctt ctaacagagc tataaaactc tgtgcatggc    360

ccaagattcc attccttgga atctgtgagg ccaagaaccc caggtcagag aacaggaggc    420

ttgccaccat cttggaagtg gctcgccacc atcttaggag ctctgtgagc ggagaccccc    480

accccccggt aacattttgg cgaccacgaa gggacctcca aagcggtgag taatattgga    540

tcactttcgc ttgctattct gtcctatcct tctttagaat tggaggaaaa tactgggcac    600

ctgtcggcca gttaaaaaca attagcgtgg ctgcccgact taagactcag gtgtgaggct    660

atctggggaa gggctttcta acaacccccca acccttctgg gttggggacg ttggtctgcc    720

ccttccactt tcaatttttct tggggaagcc aagggtcgac tagaggcaga aagctgtcgt    780

ccggaactcc tggcagtagc cggttgagat catggcgcag ccagaagtct ctactcaaca    840

gtcgcccatg cgtgcgctcc taccttttcct cctgacccat acctcctggg tcccgacgat    900

gactttcttg aaagtgtagc cccaaaattc tgcttacctc tgaatctact tcccctgatc    960

cctggctcct aggtactaat ggttcagttt catttcctct agcaagttgt atctccaaag   1020

ggatctaagg aagctctacg ctgcgtcctt aggcatctag gctataaacc caggaagtct   1080

tgtccctggt gtccctcccg atttaggcat acagctctcg acatgggcag ttatgtggga   1140

cccgttcccc atcacccttg tcaaggcccc aagtttgtaa tggctaagag gagagagaga   1200

gaaagagaga gagacggagg ggagagagag agagagagat ggaggggaga gagagagaga   1260

gagacggagg ggagagagag agagagagag agacggaggg gagagagaga gagacggagg   1320

ggagagagag agagatggag gagagaaaga caaagggagt caaagagaaa aagaaagaga   1380

aagacagaaa tggtaaaaca aacaaaaaac agcgtgccct attcctttaa aagccggggt   1440

aaatttaaaa cctataattg ataattgaag gtcttctcca tgaccctata atactccaat   1500

actaccttgt tgtcagtgta aacaagggcg tagcctgaaa acactgagac cactgacaac   1560

ctgcagcttt cctatcaaaa aatccttaac ccagtaaccg gcagatgcat tcaatctgta   1620

gcagcaactg ttttgctaac agaagaaagt agaaaagtaa cttttagagg aaacctcatt   1680

gtgagcacac cttaccagtt cagaattatt ctaagtcaaa aaagcaaaaa ggtagcttac   1740

taactcaaaa atcttaaagt atggggctat tgtgtttaaa aaaaaaaaaa ggtaatttaa   1800

caccaaccac tgataattct cttaacccag caggtttcct aacaggggat ttaaatctta   1860
```

```
attaccatac aaaggtctga ccacacctag gaggaactcc cttcaggaca ggactataga   1920
gggttcctcc caggtgattg aggaaaaaac cacagtgggt attcagtaat tgatagggag   1980
actcttgtgg aagcagagtt agaaaaattg cctaataaat ggtgtcctca aaagtgtgag   2040
ctgtttgcac tcagccaagc cttaaagtac ttacagaatc gtaaaaacta tctcaatcct   2100
gactcaaaag tttacttaca ccctctctga aatgaattta cataagaact gctttttttgg  2160
gaatgcatct tgatggggca gctgggtggt tatgaaatac tcaggaaacc agcccagctc   2220
taggacacat ccctgagcac aaaggcaatg ttgggcacgc tggtaaagga ccactagaat   2280
ccagcagcct ggactccttt ctttgtggtc aagaaaggca ggaaaacagg tgcaggactg   2340
ctacatcagt gagcataact aatctgataa gcagagggcc ttgggtggtt acacaccctg   2400
gaaaggaatt caactctgag cgcaaaggca atgttgggca cattggtaaa ggaccactag   2460
aatccagcag cccaggcccc tttctttatg gtcaagaaag gcgggaaaag gggtgcagga   2520
ctgttacctc ggtgagcgta actaatccga taagcagagg tccatgggtg attacgcacc   2580
ctgaaaagaa taagcattag gcccttaaag gatgctctag gactaatgct cattggaaaa   2640
tgactagggg tgctggcatc cctatgttct tttctcagac gggaaatgtt ctccaccctc   2700
cccaaggcaa aaacacccct aagatgtatt ctggagaatt gggaccaatt tgaccccccag  2760
acgctaagaa agagatgact tatgttcttc tgcagtacca cctggccacg atatcctctt   2820
caagggggag aaacctggcc tcctgaggga agtataaatt ataacaccat cttacagcta   2880
gacctcttct gtagaaagga gggcaaatgg agtgaagtgc catatgtgca aactttcttt   2940
tcattaagag acaacttgca attatgtaag aagtgtgatt tatgccctac aggaagccct   3000
cagagtctac ctccctaccc cagcatcccc ctgactcctt ctccaactaa taaggaaccc   3060
ccttcaaccc aaacggtcca aaaggagata gacaaagggg taaacaatga accaaagcgt   3120
gccaatgttc cctgattatg ccccctctaa gcagtgggag gaggagaatt tggcccagcc   3180
agtgtgcatg tgcctttttc tctctcagac ttaaagcaaa ttaaaataga cctaggtaaa   3240
ttctcagata accctgatgg ctatattgat gttttataag ggttaggata atcctttgat   3300
ctgacatgga gagatataat gttactgcta gatcagacac taaccccaaa tgagacaagt   3360
gccgccataa ctgcagcctg agagtttggc gatctctggt atctcactcg ggtcaatgat   3420
aggaggacaa cagaggaaag agaatgattc cccacagacc agcaggcagt tcccagtgta   3480
gaccctcact gggacacaga atcagaacat ggacattggt gctgcagaca tttgctaact   3540
tacatgctag aaggactaag gaaaactagg aagaagccta cgaattattc aatgatgtcc   3600
actataacac agggaaagga agaaaatcct actgcctttc tggagcgact aagggaggca   3660
ttgaggaagc atacttccct gtcacctgac tctattgaag gccaactaat cttaaaggat   3720
aagtttatca ctcagtcagc tgaagacatt aggaaaaaac ttcaaaagtc tgccttaggc   3780
ccagagcaaa acttagaaac ccccattgaac ttggcaacct cggtttttta taatagagat  3840
caggaggagc aggcggaaca ggacaaacgg ggtaaaaaaa aggccaccgc tttagttatg   3900
gccctcaggc aagtggactt tggaggctct ggaaaaggga aaagctgggc aaatcgaatg   3960
cctactaggg cttgcttcca gagtggtcta caaggacact ttgaaaaaga ttgtccaagt   4020
agaaataagt cgccccttcg tccatgcccc ttatatcaag ggaatcactg gaaggcccac   4080
tatcccaggg gacaaatgtc ctctgagtca gaagccacta accagatgat ccagcagcag   4140
gactgagggt gcccagggca agcactagcc catgccgtca ccctcacaga gccccaggta   4200
```

-continued

```
tgcttgacca ttgagggcca ggaggttaac tgtctcctgg acactagcac ggccttctca   4260
gtcttactct cctttcccgg acaactgtcc tccagatctg tcactatccg agggttccta   4320
ggacagtcag tcactagata cttatcccag tcactaagtt gtgactggtg aactttactc   4380
ttttcacatg cttttctaat tatccctgaa agcaccactc ccttgttagg gcgagacatt   4440
ctagcaaaag caggggccat tatacacctg aacataggag aaggaacacc tgtttgttgt   4500
cccctgcttg aggaaggaat taatcccgaa gtctgggcaa cagaaggaca atacggacga   4560
gcaaagaatg cctgtgctgt tcaagttaaa ctaaaggatt ccgcctcctt tccctaccaa   4620
aggcagtacc cccttagacc tgaggcccaa caaggactcc aaaagattgt taaggaccta   4680
aaagcccatg gcctagtaaa accatgcaat agcccctgca atactccaat tttaggagta   4740
cagaaaccca acagacagtg gaggttagtg caagatctca ggattatcat tgaggctgtt   4800
gttcctgtat agccagctgt acctaaccct tatactctgc tttcccaaat accacaggaa   4860
gcagaggggt ttacagtccg gggccttaag gacacctttt tctgcatccc tgtatatcct   4920
gactctcaat tcttgtttgc ctttgaagat ccttcaaact caacgtctca actcacctgg   4980
aatgttttac cccaagggtt cagggatagc cccccattagc ccaagacttg agccagttct   5040
tatacctgga cactcttgtc ctttggtacg tggatgattt acttttagcc acctgttcag   5100
aaaccttgtg ccatcaagcc acccaagcac tctttaattt cctcgccacc tgtggctaca   5160
ggtttccaaa ccaaaggctc agctctgctc acagcaattt aaatgcttag ggctaaaatt   5220
atccaaaggc accagggccc tcagtgagga aagtatccgg cctatactgg cttatcctca   5280
tcccaaaacc ctaaagcaac taagagtgtt ccttggcata acgggtttct gccgaatatg   5340
gattcccagg tacagcgaaa tagccagacc attatataca ctaattaagg aaactcagaa   5400
agccaatacc catttggtaa gatggacacc tgaagcagaa gcagatttcc aggccctaaa   5460
gaaggccctg acccaagccc cagtgttaag cttgccaatg ggcaagact tttctttata   5520
tgtcacagaa aaaacaggaa tagctccagg agtccttacg cagatccaag ggacgagcct   5580
gcaacccatg gcatacctga gtaaggaaat tagtggcaaa gggttggcct cattgtttat   5640
gggtagtggc agcagtcaca gtcttagtaa ctgaagcagt taaaatgata caaggaagag   5700
atcttactgt gtggacatct catgatgtga atggcatact cactgctaaa ggagacttgt   5760
gactgtcaga caactgttta cttaaatatc aggctctatt acttgaaggg ccagtgttgc   5820
gactgtgcac ttgtgcaact cttaacccag ccacattgct tccagacaat gaagaaaaga   5880
tagaacataa ctgtcaacaa ataattgctc aaacctacac tgctcgaggg gaccttttag   5940
aagttccctt gactgatccc gatctcaact tgtatactga tggaagttcc tttgcagaaa   6000
aaggacttca aaaggcggtg tatgcagtag tccttcaaaa tcgaagagct ttagaattgc   6060
taatcactga gagaggggga acgtttttat ttttagggga agaatgctgt tattatgtta   6120
atcaattcgg aatcatcacc aagaaagtta aagaaattca agatcgaata caacgtagaa   6180
cagaggagct taaaaaacac tggaccctgg ggcctcctca gccaatggat gccctggatt   6240
ctccccttct taggacctct agcagctata tttctactcc tctttggacc ctgtatcttt   6300
aacctccgtg ttaagtttgt ctcttccaga atcgaagatg taaaactaca aatcgttctt   6360
caaatggacc cccagatgca gtccatgact aagatctact gaggacccct ggaccagcct   6420
gctagcccat gctccaatgt taatgacatt gaaggcaccc ctcccaagga aatctcaact   6480
gcacaacccc tactatgctc caattcagca ggaagcagtt acagtggtcc tcggccaacc   6540
tccccaacag catttgtatt ttcctgttgg gagggggcac tgagagacag gactagctgg   6600
```

```
atttcctagg ctgactgaga atccctaagc ctagctggga aggtgaccac ttccaccttt   6660

aaacacaggg cttgcaactt agctcacacc ctaccaattg gatagtaaag agaggtcact   6720

aaaatgctaa ttaggcaaaa acaggaggta aagaaatagc caatcatcca ttgcctgaga   6780

gcacagcggg agggacaatg accaggatat aaacccaggc attccagcct gcaacggcaa   6840

ccccctttgg gtcccctctc tttgtatggg agctctgttt tcactctatt caatcttgca   6900

actgc                                                               6905
```

<210> SEQ ID NO 12
<211> LENGTH: 9565
<212> TYPE: DNA
<213> ORGANISM: Homo sapiens

<400> SEQUENCE: 12

```
gcagccccc tttgggtccc ttccctttgt atgggagctg ttttcatgct atttcactct     60

attaaatctt gcaactgcac tcttctggtc catgtttctt acggctcgag ctgagctttt    120

gctcaccgtc caccactgct gtttgccacc accgcagacc tgccgctgac tcccatccct    180

ctggatcctg cagggtgtcc gctgtgctcc tgatccagcg aggcgcccat tgccgctccc    240

aattgggcta aaggcttgcc attgttcctg cacggctaag tgcctgggtt tgttctaatt    300

gagctgaaca ctagtcactg ggttccatgg ttctcttctg tgacccacgg cttctaatag    360

aactataaca cttaccacat ggcccaagat tccattcctt ggaatccgtg aggccaagaa    420

ctccaggtca gagaatacga ggcttgccac catcttggaa gcggcctgct accatcttgg    480

aagtggttca ccaccatctt gggagctctg tgagcaagga ccccccggta acattttggc    540

aaccacgaac ggacatccaa agtggtgagt aatattggac cactttcact tgctattctg    600

tcctatcctt ccttagaatt ggaggaaaat accgggcact tgtcggccag ttaaaaacga    660

ttagtgtggc caccggactt aagactcagg tgtgaggcta tctggggaag ggctttctaa    720

caaccccaa cccttctggg ttggggactt ggtttgcctc aagccagctt ccactttcag    780

ttttcttggg gaagccgagg gccgactaga ggcagaaagc tgtcgtcctg aactcccggc    840

agtagccggt tgagatcatg gtgtagccag aagtctcaac agtcgcccat gcatgcaccc    900

ctatctttcc ttctgaccca tacctcctgg gtcccaacca caactttctt caaagtgtag    960

ccccaaaatt ctccttacct ctgaatatac ttcctctgat ccctgcctcc taggtactat   1020

tggttcagac ttccatttcc tctagcaagt tgtatctcca aagggatcta aggaagctct   1080

gcgctgcgtc cttaggcacc taggctataa cccagggagt cttatccctg gtgtccctcc   1140

caatttaggc atacagctct tgacatgggc agttatgtag gacccactcc ccaccaccct   1200

tgccagggcc ccaagtttgt aaatggctga gggaaaagag agacagagga gagagagaga   1260

aatggaggag aaagagagag agacagagag gagagagaga cagtgagaga gacagaagag   1320

agagagagac aaagaggaga gagagagagt caaagagaga aagaaagaga aagaaatagt   1380

aaaaaacagt gtgccctatt cctttaaaag ccagggtaaa tttaaaacct gtacttgata   1440

attgaaggtc ttctctgtga ccctatagca ctccaatcca ctttgtggtc agtgtaaata   1500

agagcatagg ccgaaagcac tgaggccatt gacaacccgt agcttcccta tcaaaaatcc   1560

ttaacccagt aacccgcaga tggaccaaat gcattcagtc ggtagcgcaa ctgctttgct   1620

aaaagtagaa aagtaacttt tagaggaaac ctcattgtga gcacacctca cctgttcaga   1680

attattctaa taaaaaaagc aaaaaggtag cttactaact caaaaatctt aaagtatggg   1740
```

```
gctattctgt tagaaaaagg taatgtaact ccaaccactg ataattccct taacccagca   1800
gatttcctaa cgggatttaa atcttaatta ccatacaaag gtccgaccag acctaggcgg   1860
aactcccttc aggacaggac gatagatggt tcctcccagg tgattgagga aaaaaaccac   1920
aatgggtatt cagtaattga tacggggact cttgtggaag cagagttaga aaaattgcct   1980
aataactggt ctcctcaaac gtgtgagctg tttgcactca gccaagcctt aaagtactta   2040
cagaatcaaa agactatctc aatcctgatt caaaaggtta gctacaccct ctctgtaatg   2100
catttgcata agaacttgtt tatgggaatg catcttgatg gggcagctgg gttgttataa   2160
aataggaacc cagcccagct ctaggactca cccctgagcg caaaggcaat gttgggcatg   2220
ctggtaaagg accactagaa tccagcagcc cagacccctt tctttgtggt caagaaaggc   2280
gggaaaaggg gtgcaggact gctacatcgg taagcataac taatccgata aacagaggtc   2340
catgggtggt tacgcaccct ggaaaggaac tcacccctga gcacaaaggc aatgttgggc   2400
acgctggtaa aggaccacta gaatccagca gcctggaccc ctttctttgt ggtcaagaga   2460
ggcaggaaaa caggtgcagg actgcaacat cagtgagcat aactaattcg ataagcagag   2520
gtccatgggt ggtgatgcac cctggaaaga ataagcatta ggaccataga ggacactcca   2580
ggactaaagc tcatcggaaa atgactaggg ttgctggcat ccctatgttc tttttttcaga   2640
tgggaaacgt tccccgcaag acaaaaaacgc ccctaagacg tattctggag aattgggacc   2700
aatttgaccc tcagacacta agaaagaaac gacttatatt cttctgcagt gccgcctggc   2760
actcctgagg gaagtataaa ttataacacc atcttacagc tagacctctt ttgtagaaaa   2820
ggcaaatgga gtgaagtgcc ataagtacaa actttctttt cattaagaga caactcacaa   2880
ttatgtaaaa agtgtgattt atgccctaca ggaagccttc agagtctacc tccctatccc   2940
agcatccccg actccttccc caactaataa ggacccccct tcaacccaaa tggtccaaaa   3000
ggagatagac aaaagggtaa acagtgaacc aaagagtgcc aatattcccc aattatgacc   3060
cctccaagca gtgggaggaa gagaattcgg cccagccaga gtgcatgtgc ctttttctct   3120
cccagactta aagcaaataa aaacagactt aggtaaattc tcagataacc ctgatggcta   3180
tattgatgtt ttacaagggt taggacaatt ctttgatctg acatggagag atataatgtc   3240
actgctaaat cagacactaa ccccaaatga gagaagtgcc accataactg cagcctgaga   3300
gtttggcgat ctctggtatc tcagtcaggt caatgatagg atgacaacag aggaaagaga   3360
atgattcccc acaggccagc aggcagttcc cagtctagac cctcattggg acacagaatc   3420
agaacatgga gattggtgct gcagacattt gctaacttgt gtgctagaag gactaaggaa   3480
aactaggaag aagtctatga attactcaat gatgtccacc ataacacagg gaagggaaga   3540
aaatcctact gcctttctgg agagactaag ggaggcattg aggaagcgtg cctctctgtc   3600
acctgactct tctgaaggcc aactaatctt aaagcgtaag tttatcactc agtcagctgc   3660
agacattaga aaaaaacttc aaaagtctgc cgtaggcccg gagcaaaact tagaaaccct   3720
attgaacttg gcaacctcgg ttttttataa tagagatcag gaggagcagg cggaacagga   3780
caaacgggat taaaaaaaag gccaccgctt tagtcatgac cctcaggcaa gtggactttg   3840
gaggctctgg aaaagggaaa agctgggcaa attgaatgcc taatagggct tgcttccagt   3900
gcggtctaca aggacacttt aaaaaagatt gtccaagtag aagtaagccg ccccctcgtc   3960
catgcccctt atttcaaggg aatcactgga aggcccactg ccccagggga caaaggtcct   4020
ctgagtcaga agccactaac cagatgatcc agcagcagga ctgagggtgc ctggggcaag   4080
cgccatccca tgccatcacc ctcacagagc cctgggtatg cttgaccatt gagggccagg   4140
```

```
aggttgtctc ctggacactg gtgcggtctt cttagtctta ctcttctgtc ccggacaact   4200
gtcctccaga tctgtcacta tctgaggggg tcctaagacg ggcagtcact agatacttct   4260
cccagccact aagttatgac tggggagctt tattcttttc acatgctttt ctaattatgc   4320
ttgaaagccc cactaccttg ttagggagag acattctagc aaaagcaggg gccattatac   4380
acctgaacat aggagaagga acacccgttt gttgtcccct gcttgaggaa ggaattaatc   4440
ctgaagtctg ggcaacagaa ggacaatatg gacgagcaaa gaatgcccgt cctgttcaag   4500
ttaaactaaa ggattccacc tcctttccct accaaaggca gtacccccctc agacccaagg   4560
cccaacaagg actccaaaag attgttaagg acctaaaagc ccaaggccta gtaaaaccat   4620
gcagtaaccc ctgcagtact ccaattttag gagtacagaa acccaacaga cagtggaggt   4680
tagtgcaaga tctcaggatt atcaatgagg ctgttgttcc tctatagcca gctgtaccta   4740
gcccttatac tctgctttcc caaataccag aggaagcaga gtggtttaca gtcctggacc   4800
ttcaggatgc cttcttctgc atccctgtac atcctgactc tcaattcttg tttgcctttg   4860
aagatacttc aaacccaaca tctcaactca cctggactat tttaccccaa gggttcaggg   4920
atagtcccca tctatttggc caggcattag cccaagactt gagccaatcc tcatacctgg   4980
acacttgtcc ttcggtaggt ggatgattta cttttggccg cccattcaga aaccttgtgc   5040
catcaagcca cccaagcgct cttcaatttc ctcgctacct gtggctacat ggtttccaaa   5100
ccaaaggctc aactctgctc acagcaggtt acttagggct aaaattatcc aaaggcacca   5160
gggccctcag tgaggaacac atccagccta tactggctta tcctcatccc aaaaccctaa   5220
agcaactaag ggattcctt ggcgtaatag gtttctgccg aaaatggatt cccaggtatg   5280
gcgaaatagc caggtcatta aatacactaa ttaaggaaac tcagaaagcc aatacccatt   5340
tagtaagatg gacaactgaa gtagaagtgg ctttccaggc cctaacccaa gccccagtgt   5400
taagtttgcc aacagggcaa gacttttctt catatgtcac agaaaaaaca ggaatagctc   5460
taggagtcct tacacagatc cgagggatga gcttgcaacc tgtggcatac ctgactaagg   5520
aaattgatgt agtggcaaag ggttgacctc attgtttacg ggtagtggtg gcagtagcag   5580
tcttagtatc tgaagcagtt aaaataatac agggaagaga tcttactgtg tggacatctc   5640
atgatgtgaa tggcatactc actgctaaag gagacttgtg gctgtcagac aactgtttac   5700
ttaaatgtca ggctctatta cttgaagggc cagtgctgcg actgtgcact tgtgcaactc   5760
ttaacccagc cacatttctt ccagacaatg aagaaaagat aaaacataac tgtcaacaag   5820
taatttctca aacctatgcc actcgagggg accttttaga ggttcctttg actgatcccg   5880
acctcaactt gtatactgat ggaagttcct ttgtagaaaa aggacttcga aaagtggggt   5940
atgcagtggt cagtgataat ggaatacttg aaagtaatcc cctcactcca ggaactagtg   6000
ctcagctagc agaactaata gccctcactt gggcactaga attaggagaa gaaaaaaggg   6060
caaatatata tacagactct aaatatgctt acctagtcct ccatgcccat gcagcaatat   6120
ggaaagaaag ggaattccta acttctgaga gaacacctat caaacatcag gaagccatta   6180
ggaaattatt attggctgta cagaaaccta aagaggtggc agtcttacac tgccggggtc   6240
atcagaaagg aaaggaaagg gaaatagaag agaactgcca agcagatatt gaagccaaaa   6300
gagctgcaag gcaggaccct ccattagaaa tgcttataaa acaacccccta gtatagggta   6360
atcccctccg ggaaaccaag ccccagtact cagcaggaga aacagaatgg ggaacctcac   6420
gaggacagtt ttctcccctc gggacggcta gccactgaag aagggaaaat acttttgcct   6480
```

-continued

```
gcaactatcc aatggaaatt acttaaaacc cttcatcaaa cctttcactt aggcatcgat   6540
agcacccatc agatggccaa atcattattt actggaccag gccttttcaa aactatcaag   6600
cagatagtca gggcctgtga agtgtgccag agaaataatc ccctgcctta tcgccaagct   6660
ccttcaggag aacaaagaac aggccattac cctggagaag actggcaact gattttaccc   6720
acaagcccaa acctcaggga tttcagtatc tactagtctg ggtagatact ttcacgggtt   6780
gggcagaggc cttcccctgt aggacagaaa aggcccaaga ggtaataaag gcactagttc   6840
atgaaataat tcccagattc ggacttcccc gaggcttaca gagtgacaat agccctgctt   6900
tccaggccac agtaacccag ggagtatccc aggcgttagg tatacgatat cacttacact   6960
gcgcctgaag gccacagtcc tcagggaagg tcgagaaaat gaatgaaaca ctcaaaggac   7020
atctaaaaaa gcaaacccag gaaacccacc tcacatggcc tgctctgttg cctatagcct   7080
taaaaagaat ctgcaacttt ccccaaaaag caggacttag cccatacgaa atgctgtatg   7140
gaaggccctt cataaccaat gaccttgtgc ttgacccaag acagccaact tagttgcaga   7200
catcacctcc ttagccaaat atcaacaagt tcttaaaaca ttacaaggaa cctatccctg   7260
agaagaggga aaagaactat tccacccttg tgacatggta ttagtcaagt cccttccctc   7320
taattcccca tccctagata catcctggga aggaccctac ccagtcattt tatctacccc   7380
aactgcggtt aaagtggctg gagtggagtc ttggatacat cacacttgag tcaaatcctg   7440
gatactgcca aaggaacctg aaaatccagg agacaacgct agctattcct gtgaacctct   7500
agaggatttg cgcctgctct tcaaacaaca accaggagga aagtaactaa aatcataaat   7560
ccccatggcc ctcccttatc atatttttct ctttactgtt cttttaccct ctttcactct   7620
cactgcaccc cctccatgcc gctgtatgac cagtagctcc ccttaccaag agtttctatg   7680
gagaatgcag cgtcccggaa atattgatgc cccatcgtat aggagtcttt ctaagggaac   7740
ccccaccttc actgcccaca cccatatgcc ccgcaactgc tatcactctg ccactctttg   7800
catgcatgca aatactcatt attggacagg aaaaatgatt aatcctagtt gtcctggagg   7860
acttggagtc actgtctgtt ggacttactt cacccaaact ggtatgtctg atgggggtgg   7920
agttcaagat caggcaagag aaaaacatgt aaaagaagta atctcccaac tcacccgggt   7980
acatggcacc tctagcccct acaaaggact agatctctca aaactacatg aaaccctccg   8040
tacccatact cgcctggtaa gcctatttaa taccaccctc actgggctcc atgaggtctc   8100
ggcccaaaac cctactaact gttggatatg cctcccccctg aacttcaggc catatgtttc   8160
aatccctgta cctgaacaat ggaacaactt cagcacagaa ataaacacca cttccgtttt   8220
agtaggacct cttgtttcca atctggaaat aacccatacc tcaaacctca cctgtgtaaa   8280
atttagcaat actacataca caaccaactc ccaatgcatc aggtgggtaa ctcctcccac   8340
acaaatagtc tgcctaccct caggaatatt ttttgtctgt ggtacctcag cctatcgttg   8400
tttgaatggc tcttcagaat ctatgtgctt cctctcattc ttagtgcccc ctatgaccat   8460
ctacactgaa caagatttat acagttatgt catatctaag ccccgcaaca aaagagtacc   8520
cattcttcct tttgttatag gagcaggagt gctaggtgca ctaggtactg gcattggcgg   8580
tatcacaacc tctactcagt tctactacaa actatctcaa gaactaaatg gggacatgga   8640
acgggtcgcc gactccctgg tcaccttgca agatcaactt aactccctag cagcagtagt   8700
ccttcaaaat cgaagagctt tagacttgct aaccgctgaa agagggggaa cctgtttatt   8760
tttaggggaa gaatgctgtt attatgttaa tcaatccgga atcgtcactg agaaagttaa   8820
agaaattcga gatcgaatac aacgtagagc agaggagctt cgaaacactg gaccctgggg   8880
```

```
cctcctcagc caatggatgc cctggattct cccccttctta ggacctctag cagctataat   8940

attgctactc ctctttggac cctgtatctt taacctcctt gttaactttg tctcttccag   9000

aatcgaagct gtaaaactac aaatggagcc caagatgcag tccaagacta agatctaccg   9060

cagaccccctg gaccggcctg ctagcccacg atctgatgtt aatgacatca aaggcacccc   9120

tcctgaggaa atctcagctg cacaacctct actacgcccc aattcagcag gaagcagtta   9180

gagcggtcgt cggccaacct ccccaacagc acttaggttt tcctgttgag atgggggact   9240

gagagacagg actagctgga tttcctaggc tgactaagaa tccctaagcc tagctgggaa   9300

ggtgaccaca tccaccttta aacacggggc ttgcaactta gctcacacct gaccaatcag   9360

agagctcact aaaatgctaa ttaggcaaag acaggaggta aagaaatagc caatcatcta   9420

ttgcctgaga gcacagcagg agggacaatg atcgggatat aaacccaagt cttcgagccg   9480

gcaacggcaa cccccctttgg gtcccctccc tttgtatggg agctctgttt tcatgctatt   9540

tcactctatt aaatcttgca actgc                                        9565


<210> SEQ ID NO 13
<211> LENGTH: 543
<212> TYPE: DNA
<213> ORGANISM: Homo sapiens

<400> SEQUENCE: 13

atgacaacag aagaaagaaa acaattcccc acaggccagc aggcagttcc cagcgtagac     60

cttcattggg acacagaatc agaacatgga gattggtgcc gcagacattt actaacttgc    120

gcgctagaag cactaaggaa aactaggaag aagcctatga attattcaat gatgtccact    180

ataacacagg gaaaggaaga aaatcctact gcctttctgg agagactaag ggaggcattg    240

agaaagcata cctctctgtc acctgactct attgaaggcc aactaatctt aaaggataag    300

ttttccactc agtcagctgc agacattaga aaaaaacttc aaaagtctgc gttaggccgg    360

gagcaaaact tagaaaccct attgaacttg gcaacctcag ttttttatga tagagatcag    420

gaggatcagg tggaatggac aaatgagatt ttaaaaaaag gccaccactt tagtcatggc    480

cctcaggcaa gcagactttg gacactctgg aaaagggaaa agctgggcaa atcgaatgcc    540

taa                                                                543


<210> SEQ ID NO 14
<211> LENGTH: 180
<212> TYPE: PRT
<213> ORGANISM: Homo sapiens

<400> SEQUENCE: 14

Met Thr Thr Glu Glu Arg Lys Gln Phe Pro Thr Gly Gln Gln Ala Val
1               5                   10                  15

Pro Ser Val Asp Leu His Trp Asp Thr Glu Ser Glu His Gly Asp Trp
            20                  25                  30

Cys Arg Arg His Leu Leu Thr Cys Ala Leu Glu Ala Leu Arg Lys Thr
        35                  40                  45

Arg Lys Lys Pro Met Asn Tyr Ser Met Met Ser Thr Ile Thr Gln Gly
    50                  55                  60

Lys Glu Glu Asn Pro Thr Ala Phe Leu Glu Arg Leu Arg Glu Ala Leu
65                  70                  75                  80

Arg Lys His Thr Ser Leu Ser Pro Asp Ser Ile Glu Gly Gln Leu Ile
                85                  90                  95
```

```
Leu Lys Asp Lys Phe Ser Thr Gln Ser Ala Ala Asp Ile Arg Lys Lys
            100                 105                 110

Leu Gln Lys Ser Ala Leu Gly Arg Glu Gln Asn Leu Glu Thr Leu Leu
        115                 120                 125

Asn Leu Ala Thr Ser Val Phe Tyr Asp Arg Asp Gln Glu Asp Gln Val
    130                 135                 140

Glu Trp Thr Asn Glu Ile Leu Lys Lys Gly His His Phe Ser His Gly
145                 150                 155                 160

Pro Gln Ala Ser Arg Leu Trp Thr Leu Trp Lys Arg Glu Lys Leu Gly
                165                 170                 175

Lys Ser Asn Ala
            180


<210> SEQ ID NO 15
<211> LENGTH: 435
<212> TYPE: DNA
<213> ORGANISM: Homo sapiens

<400> SEQUENCE: 15

atgattcagc cccaggactc agggtgccca gggcaagcgc cagcctatgc catcaccctc     60

acagagccct gggtatgctt gaccattgag ggtcaggagg ttaactatct cctggacact    120

ggcgtggcct tctcagtctt actctcctgt cccggacaac tgtcctccag atctgtcact    180

atccgagggt ttctacgaca gccagccact agatacttct cccagccact aagttgtgac    240

tggggaactc tactcttttc acatgttttt ctaattatgc ctgaaagccc cactcctttg    300

ttagggaaag acattctagc aaaagcaggg gccattatac acctgaacat aggagaagga    360

acacctgttt gttgtcccct gcttgaagaa ggaattaatc ctgaagtctg gacaacagaa    420

ggacaataca gatga                                                     435


<210> SEQ ID NO 16
<211> LENGTH: 144
<212> TYPE: PRT
<213> ORGANISM: Homo sapiens

<400> SEQUENCE: 16

Met Ile Gln Pro Gln Asp Ser Gly Cys Pro Gly Gln Ala Pro Ala Tyr
1               5                   10                  15

Ala Ile Thr Leu Thr Glu Pro Trp Val Cys Leu Thr Ile Glu Gly Gln
            20                  25                  30

Glu Val Asn Tyr Leu Leu Asp Thr Gly Val Ala Phe Ser Val Leu Leu
        35                  40                  45

Ser Cys Pro Gly Gln Leu Ser Ser Arg Ser Val Thr Ile Arg Gly Phe
    50                  55                  60

Leu Arg Gln Pro Ala Thr Arg Tyr Phe Ser Gln Pro Leu Ser Cys Asp
65                  70                  75                  80

Trp Gly Thr Leu Leu Phe Ser His Val Phe Leu Ile Met Pro Glu Ser
                85                  90                  95

Pro Thr Pro Leu Leu Gly Lys Asp Ile Leu Ala Lys Ala Gly Ala Ile
            100                 105                 110

Ile His Leu Asn Ile Gly Glu Gly Thr Pro Val Cys Cys Pro Leu Leu
        115                 120                 125

Glu Glu Gly Ile Asn Pro Glu Val Trp Thr Thr Glu Gly Gln Tyr Arg
    130                 135                 140


<210> SEQ ID NO 17
```

<211> LENGTH: 312
<212> TYPE: DNA
<213> ORGANISM: Homo sapiens

<400> SEQUENCE: 17
atgccccctc caggcagtgg gaggaggaga attcggccca gccagagtgc atgtaccttt 60
ttttttctct cagacttaaa gcaaattaaa atagacctag gtaaattctc agataaccct 120
gatggctata ttgatgtttt acaagggtta ggacaatcct ttgctctgac atggagagat 180
ataatgttac tgctaaatca gacactaacc ccaaatgaga gaagtgtcac catagctgca 240
gcccaagagt ttggcaatct ctggtatctc agtcaggtca atgataggat gacaacagag 300
gaaagggaat ga 312

<210> SEQ ID NO 18
<211> LENGTH: 103
<212> TYPE: PRT
<213> ORGANISM: Homo sapiens

<400> SEQUENCE: 18

Met Pro Pro Pro Gly Ser Gly Arg Arg Arg Ile Arg Pro Ser Gln Ser
1 5 10 15

Ala Cys Thr Phe Phe Phe Leu Ser Asp Leu Lys Gln Ile Lys Ile Asp
20 25 30

Leu Gly Lys Phe Ser Asp Asn Pro Asp Gly Tyr Ile Asp Val Leu Gln
35 40 45

Gly Leu Gly Gln Ser Phe Ala Leu Thr Trp Arg Asp Ile Met Leu Leu
50 55 60

Leu Asn Gln Thr Leu Thr Pro Asn Glu Arg Ser Val Thr Ile Ala Ala
65 70 75 80

Ala Gln Glu Phe Gly Asn Leu Trp Tyr Leu Ser Gln Val Asn Asp Arg
85 90 95

Met Thr Thr Glu Glu Arg Glu
100

<210> SEQ ID NO 19
<211> LENGTH: 207
<212> TYPE: DNA
<213> ORGANISM: Homo sapiens

<400> SEQUENCE: 19
atgggcagtt atgtaggacc cattccccac cacacttgcc agggccccaa gtttgtaatg 60
gctaagagag agacacagag agagagagag agatggagag agagacaagg agggagtcaa 120
agagaaaaag aaagaaaaag aaatagtaga aaaaaaagtg tgccctattc ctttaaaagc 180
cagggtaaat ttaaaacctg taattga 207

<210> SEQ ID NO 20
<211> LENGTH: 68
<212> TYPE: PRT
<213> ORGANISM: Homo sapiens

<400> SEQUENCE: 20

Met Gly Ser Tyr Val Gly Pro Ile Pro His His Thr Cys Gln Gly Pro
1 5 10 15

Lys Phe Val Met Ala Lys Arg Glu Thr Gln Arg Glu Arg Glu Arg Trp
20 25 30

Arg Glu Arg Gln Gly Gly Ser Gln Arg Glu Lys Glu Arg Lys Arg Asn
35 40 45

```
Ser Arg Lys Lys Ser Val Pro Tyr Ser Phe Lys Ser Gln Gly Lys Phe
    50                  55                  60

Lys Thr Cys Asn
65


<210> SEQ ID NO 21
<211> LENGTH: 306
<212> TYPE: DNA
<213> ORGANISM: Homo sapiens

<400> SEQUENCE: 21

atgtcaagaa agaaacgact tatattcttc tgcagtactg cctggccacg atatcctctt     60

caagggggag aaacctggcc tcctgaggga agtacaaatt ataacaccat cttacagcta    120

gacctctttt gtagaaaaga aggcaaatgg agtgaagtgc catatgtgca aactttcttt    180

tcattaagag acaactcaca attatgtaaa aagtgtggtt tatgtcttac aggaagccct    240

cagagtctac ctccctatcc cagcattccc ccgactcctt ccccaactaa taagcaccac    300

ccttga                                                               306


<210> SEQ ID NO 22
<211> LENGTH: 101
<212> TYPE: PRT
<213> ORGANISM: Homo sapiens

<400> SEQUENCE: 22

Met Ser Arg Lys Lys Arg Leu Ile Phe Phe Cys Ser Thr Ala Trp Pro
1               5                   10                  15

Arg Tyr Pro Leu Gln Gly Gly Glu Thr Trp Pro Pro Glu Gly Ser Thr
            20                  25                  30

Asn Tyr Asn Thr Ile Leu Gln Leu Asp Leu Phe Cys Arg Lys Glu Gly
        35                  40                  45

Lys Trp Ser Glu Val Pro Tyr Val Gln Thr Phe Phe Ser Leu Arg Asp
    50                  55                  60

Asn Ser Gln Leu Cys Lys Lys Cys Gly Leu Cys Leu Thr Gly Ser Pro
65                  70                  75                  80

Gln Ser Leu Pro Pro Tyr Pro Ser Ile Pro Pro Thr Pro Ser Pro Thr
                85                  90                  95

Asn Lys His His Pro
            100


<210> SEQ ID NO 23
<211> LENGTH: 603
<212> TYPE: DNA
<213> ORGANISM: Homo sapiens

<400> SEQUENCE: 23

atgctagaag gactaaggaa aactaggaag aagcctacga attattcaat gatgtccact     60

ataacacagg gaaaggaaga aaatcctact gcctttctgg agcgactaag ggaggcattg    120

aggaagcata cttccctgtc acctgactct attgaaggcc aactaatctt aaaggataag    180

tttatcactc agtcagctga agacattagg aaaaaacttc aaaagtctgc cttaggccca    240

gagcaaaact tagaaacccc attgaacttg gcaacctcgg ttttttataa tagagatcag    300

gaggagcagg cggaacagga caaacggggt aaaaaaaagg ccaccgcttt agttatggcc    360

ctcaggcaag tggactttgg aggctctgga aaagggaaaa gctgggcaaa tcgaatgcct    420

actagggctt gcttccagag tggtctacaa ggacactttg aaaaagattg tccaagtaga    480
```

```
aataagtcgc cccttcgtcc atgcccctta tatcaaggga atcactggaa ggcccactat    540

cccaggggac aaatgtcctc tgagtcagaa gccactaacc agatgatcca gcagcaggac    600

tga                                                                  603


<210> SEQ ID NO 24
<211> LENGTH: 200
<212> TYPE: PRT
<213> ORGANISM: Homo sapiens

<400> SEQUENCE: 24

Met Leu Glu Gly Leu Arg Lys Thr Arg Lys Lys Pro Thr Asn Tyr Ser
1               5                   10                  15

Met Met Ser Thr Ile Thr Gln Gly Lys Glu Glu Asn Pro Thr Ala Phe
            20                  25                  30

Leu Glu Arg Leu Arg Glu Ala Leu Arg Lys His Thr Ser Leu Ser Pro
        35                  40                  45

Asp Ser Ile Glu Gly Gln Leu Ile Leu Lys Asp Lys Phe Ile Thr Gln
    50                  55                  60

Ser Ala Glu Asp Ile Arg Lys Lys Leu Gln Lys Ser Ala Leu Gly Pro
65                  70                  75                  80

Glu Gln Asn Leu Glu Thr Pro Leu Asn Leu Ala Thr Ser Val Phe Tyr
                85                  90                  95

Asn Arg Asp Gln Glu Glu Gln Ala Glu Gln Asp Lys Arg Gly Lys Lys
            100                 105                 110

Lys Ala Thr Ala Leu Val Met Ala Leu Arg Gln Val Asp Phe Gly Gly
        115                 120                 125

Ser Gly Lys Gly Lys Ser Trp Ala Asn Arg Met Pro Thr Arg Ala Cys
    130                 135                 140

Phe Gln Ser Gly Leu Gln Gly His Phe Glu Lys Asp Cys Pro Ser Arg
145                 150                 155                 160

Asn Lys Ser Pro Leu Arg Pro Cys Pro Leu Tyr Gln Gly Asn His Trp
                165                 170                 175

Lys Ala His Tyr Pro Arg Gly Gln Met Ser Ser Glu Ser Glu Ala Thr
            180                 185                 190

Asn Gln Met Ile Gln Gln Gln Asp
        195                 200


<210> SEQ ID NO 25
<211> LENGTH: 1617
<212> TYPE: DNA
<213> ORGANISM: Homo sapiens

<400> SEQUENCE: 25

atggccctcc cttatcatat ttttctcttt actgttcttt taccctcttt cactctcact     60

gcacccccctc catgccgctg tatgaccagt agctcccctt accaagagtt tctatggaga   120

atgcagcgtc ccggaaatat tgatgcccca tcgtatagga gtctttctaa gggaaccccc    180

accttcactg cccacaccca tatgccccgc aactgctatc actctgccac tctttgcatg    240

catgcaaata ctcattattg gacaggaaaa atgattaatc ctagttgtcc tggaggactt    300

ggagtcactg tctgttggac ttacttcacc caaactggta tgtctgatgg gggtggagtt    360

caagatcagg caagagaaaa acatgtaaaa gaagtaatct cccaactcac ccgggtacat    420

ggcacctcta gcccctacaa aggactagat ctctcaaaac tacatgaaac cctccgtacc    480

catactcgcc tggtaagcct atttaatacc accctcactg ggctccatga ggtctcggcc    540
```

```
caaaacccta ctaactgttg gatatgcctc cccctgaact tcaggccata tgtttcaatc    600
cctgtacctg aacaatggaa caacttcagc acagaaataa acaccacttc cgttttagta    660
ggacctcttg tttccaatct ggaaataacc catacctcaa acctcacctg tgtaaaattt    720
agcaatacta catacacaac caactcccaa tgcatcaggt gggtaactcc tcccacacaa    780
atagtctgcc taccctcagg aatatttttt gtctgtggta cctcagccta tcgttgtttg    840
aatggctctt cagaatctat gtgcttcctc tcattcttag tgccccctat gaccatctac    900
actgaacaag atttatacag ttatgtcata tctaagcccc gcaacaaaag agtacccatt    960
cttccttttg ttataggagc aggagtgcta ggtgcactag gtactggcat tggcggtatc   1020
acaacctcta ctcagttcta ctacaaacta tctcaagaac taaatgggga catggaacgg   1080
gtcgccgact ccctggtcac cttgcaagat caacttaact ccctagcagc agtagtcctt   1140
caaaatcgaa gagctttaga cttgctaacc gctgaaagag ggggaacctg tttatttta   1200
ggggaagaat gctgttatta tgttaatcaa tccggaatcg tcactgagaa agttaaagaa   1260
attcgagatc gaatacaacg tagagcagag gagcttcgaa acactggacc ctggggcctc   1320
ctcagccaat ggatgccctg gattctcccc ttcttaggac ctctagcagc tataatattg   1380
ctactcctct ttggaccctg tatctttaac ctccttgtta actttgtctc ttccagaatc   1440
gaagctgtaa aactacaaat ggagcccaag atgcagtcca agactaagat ctaccgcaga   1500
cccctggacc ggcctgctag cccacgatct gatgttaatg acatcaaagg caccccctcct   1560
gaggaaatct cagctgcaca acctctacta cgccccaatt cagcaggaag cagttag      1617
```

<210> SEQ ID NO 26
<211> LENGTH: 538
<212> TYPE: PRT
<213> ORGANISM: Homo sapiens

<400> SEQUENCE: 26

```
Met Ala Leu Pro Tyr His Ile Phe Leu Phe Thr Val Leu Leu Pro Ser
1               5                   10                  15

Phe Thr Leu Thr Ala Pro Pro Pro Cys Arg Cys Met Thr Ser Ser Ser
            20                  25                  30

Pro Tyr Gln Glu Phe Leu Trp Arg Met Gln Arg Pro Gly Asn Ile Asp
        35                  40                  45

Ala Pro Ser Tyr Arg Ser Leu Ser Lys Gly Thr Pro Thr Phe Thr Ala
    50                  55                  60

His Thr His Met Pro Arg Asn Cys Tyr His Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Val Thr Val Cys Trp Thr Tyr Phe Thr Gln Thr
            100                 105                 110

Gly Met Ser Asp Gly Gly Gly Val Gln Asp Gln Ala Arg Glu Lys His
        115                 120                 125

Val Lys Glu Val Ile Ser Gln Leu Thr Arg Val His Gly Thr Ser Ser
    130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys Leu Pro Leu
```

```
            180                 185                 190

Asn Phe Arg Pro Tyr Val Ser Ile Pro Val Pro Glu Gln Trp Asn Asn
        195                 200                 205

Phe Ser Thr Glu Ile Asn Thr Thr Ser Val Leu Val Gly Pro Leu Val
    210                 215                 220

Ser Asn Leu Glu Ile Thr His Thr Ser Asn Leu Thr Cys Val Lys Phe
225                 230                 235                 240

Ser Asn Thr Thr Tyr Thr Thr Asn Ser Gln Cys Ile Arg Trp Val Thr
                245                 250                 255

Pro Pro Thr Gln Ile Val Cys Leu Pro Ser Gly Ile Phe Phe Val Cys
            260                 265                 270

Gly Thr Ser Ala Tyr Arg Cys Leu Asn Gly Ser Ser Glu Ser Met Cys
        275                 280                 285

Phe Leu Ser Phe Leu Val Pro Pro Met Thr Ile Tyr Thr Glu Gln Asp
    290                 295                 300

Leu Tyr Ser Tyr Val Ile Ser Lys Pro Arg Asn Lys Arg Val Pro Ile
305                 310                 315                 320

Leu Pro Phe Val Ile Gly Ala Gly Val Leu Gly Ala Leu Gly Thr Gly
                325                 330                 335

Ile Gly Gly Ile Thr Thr Ser Thr Gln Phe Tyr Tyr Lys Leu Ser Gln
            340                 345                 350

Glu Leu Asn Gly Asp Met Glu Arg Val Ala Asp Ser Leu Val Thr Leu
        355                 360                 365

Gln Asp Gln Leu Asn Ser Leu Ala Ala Val Val Leu Gln Asn Arg Arg
    370                 375                 380

Ala Leu Asp Leu Leu Thr Ala Glu Arg Gly Gly Thr Cys Leu Phe Leu
385                 390                 395                 400

Gly Glu Glu Cys Cys Tyr Tyr Val Asn Gln Ser Gly Ile Val Thr Glu
                405                 410                 415

Lys Val Lys Glu Ile Arg Asp Arg Ile Gln Arg Arg Ala Glu Glu Leu
            420                 425                 430

Arg Asn Thr Gly Pro Trp Gly Leu Leu Ser Gln Trp Met Pro Trp Ile
        435                 440                 445

Leu Pro Phe Leu Gly Pro Leu Ala Ala Ile Ile Leu Leu Leu Leu Phe
    450                 455                 460

Gly Pro Cys Ile Phe Asn Leu Leu Val Asn Phe Val Ser Ser Arg Ile
465                 470                 475                 480

Glu Ala Val Lys Leu Gln Met Glu Pro Lys Met Gln Ser Lys Thr Lys
                485                 490                 495

Ile Tyr Arg Arg Pro Leu Asp Arg Pro Ala Ser Pro Arg Ser Asp Val
            500                 505                 510

Asn Asp Ile Lys Gly Thr Pro Pro Glu Glu Ile Ser Ala Ala Gln Pro
        515                 520                 525

Leu Leu Arg Pro Asn Ser Ala Gly Ser Ser
    530                 535


<210> SEQ ID NO 27
<211> LENGTH: 18
<212> TYPE: DNA
<213> ORGANISM: Artificial sequence
<220> FEATURE:
<223> OTHER INFORMATION: Synthetic Construct - amplification primer

<400> SEQUENCE: 27

tgcagatgct gtgtctgg                                                 18
```

<210> SEQ ID NO 28
<211> LENGTH: 17
<212> TYPE: DNA
<213> ORGANISM: Artificial sequence
<220> FEATURE:
<223> OTHER INFORMATION: Synthetic Construct - amplification primer

<400> SEQUENCE: 28
cgtactggcc caggacc 17

<210> SEQ ID NO 29
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 29
ggttcgtgct aattgagctg 20

<210> SEQ ID NO 30
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 30
atggtggcaa gcttcttgtt 20

<210> SEQ ID NO 31
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 31
tgagctttcc ctcactgtcc 20

<210> SEQ ID NO 32
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 32
tgttcggctt gattaggatg 20

<210> SEQ ID NO 33
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 33
catggcccaa tattccattc 20

<210> SEQ ID NO 34
<211> LENGTH: 21
<212> TYPE: DNA
<213> ORGANISM: Artificial sequence
<220> FEATURE:

<223> OTHER INFORMATION: Synthetic Construct - amplification primer

<400> SEQUENCE: 34
ggtccttgtt cacagaactc c 21

<210> SEQ ID NO 35
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 35
ccgctcctga ttggactaaa 20

<210> SEQ ID NO 36
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 36
cgtgggtcaa ggaagagaac 20

<210> SEQ ID NO 37
<211> LENGTH: 21
<212> TYPE: DNA
<213> ORGANISM: Artificial sequence
<220> FEATURE:
<223> OTHER INFORMATION: Synthetic Construct - amplification primer

<400> SEQUENCE: 37
atgacccgca gcttctaaca g 21

<210> SEQ ID NO 38
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 38
ctccgctcac agagctccta 20

<210> SEQ ID NO 39
<211> LENGTH: 21
<212> TYPE: DNA
<213> ORGANISM: Artificial sequence
<220> FEATURE:
<223> OTHER INFORMATION: Synthetic Construct - amplification primer

<400> SEQUENCE: 39
ccaacatcac taacacaacc t 21

<210> SEQ ID NO 40
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 40
gggagttagt aaggggtttg 20

<210> SEQ ID NO 41
<211> LENGTH: 24
<212> TYPE: DNA
<213> ORGANISM: Artificial sequence
<220> FEATURE:
<223> OTHER INFORMATION: Synthetic Construct - amplification primer

<400> SEQUENCE: 41
caacctatta aacaaaacta aatt 24

<210> SEQ ID NO 42
<211> LENGTH: 27
<212> TYPE: DNA
<213> ORGANISM: Artificial sequence
<220> FEATURE:
<223> OTHER INFORMATION: Synthetic Construct - amplification primer

<400> SEQUENCE: 42
agatttaata gagtgaaaat agagttt 27

<210> SEQ ID NO 43
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 43
ttattagttt aggggatagt tg 22

<210> SEQ ID NO 44
<211> LENGTH: 23
<212> TYPE: DNA
<213> ORGANISM: Artificial sequence
<220> FEATURE:
<223> OTHER INFORMATION: Synthetic Construct - amplification primer

<400> SEQUENCE: 44
acacaataaa caacctacta aat 23

<210> SEQ ID NO 45
<211> LENGTH: 19
<212> TYPE: DNA
<213> ORGANISM: Artificial sequence
<220> FEATURE:
<223> OTHER INFORMATION: Synthetic Construct - amplification primer

<400> SEQUENCE: 45
gagggtaagt ggtgataaa 19

<210> SEQ ID NO 46
<211> LENGTH: 21
<212> TYPE: DNA
<213> ORGANISM: Artificial sequence
<220> FEATURE:
<223> OTHER INFORMATION: Synthetic Construct - amplification primer

<400> SEQUENCE: 46
aacctactaa atccaaaaaa a 21

<210> SEQ ID NO 47
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 47
taggatttta ggtttattgt ta 22

<210> SEQ ID NO 48
<211> LENGTH: 19
<212> TYPE: DNA
<213> ORGANISM: Artificial sequence
<220> FEATURE:
<223> OTHER INFORMATION: Synthetic Construct - amplification primer

<400> SEQUENCE: 48
aaaaataaaa tattaaacc 19

<210> SEQ ID NO 49
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 49
atatgtggga gtgagagata 20

<210> SEQ ID NO 50
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 50
caacaacaaa caataataat aa 22

<210> SEQ ID NO 51
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 51
ttgagttttt ttattgatag tg 22

<210> SEQ ID NO 52
<211> LENGTH: 21
<212> TYPE: DNA
<213> ORGANISM: Artificial sequence
<220> FEATURE:
<223> OTHER INFORMATION: Synthetic Construct - amplification primer

<400> SEQUENCE: 52
tctaaatcct attttcctac t 21

<210> SEQ ID NO 53
<211> LENGTH: 24
<212> TYPE: DNA
<213> ORGANISM: Artificial sequence
<220> FEATURE:
<223> OTHER INFORMATION: Synthetic Construct - amplification primer

<400> SEQUENCE: 53 gttttttat tgatagtgag agat 24

<210> SEQ ID NO 54
<211> LENGTH: 20

<212> TYPE: DNA
<213> ORGANISM: Artificial sequence
<220> FEATURE:
<223> OTHER INFORMATION: Synthetic Construct - amplification primer

<400> SEQUENCE: 54
taacaaacct ttaatccaat 20

<210> SEQ ID NO 55
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 55
tttagtgagg atgatgtaat at 22

<210> SEQ ID NO 56
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 56
caacttaata aaaataaacc ca 22

<210> SEQ ID NO 57
<211> LENGTH: 24
<212> TYPE: DNA
<213> ORGANISM: Artificial sequence
<220> FEATURE:
<223> OTHER INFORMATION: Synthetic Construct - amplification primer

<400> SEQUENCE: 57
ataatgtttt agtaagtgtt ggat 24

<210> SEQ ID NO 58
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 58
acaattacaa acctttaacc 20

<210> SEQ ID NO 59
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 59
aattcattca acatccattc 20

<210> SEQ ID NO 60
<211> LENGTH: 26
<212> TYPE: DNA
<213> ORGANISM: Artificial sequence
<220> FEATURE:
<223> OTHER INFORMATION: Synthetic Construct - amplification primer

<400> SEQUENCE: 60

-continued

```
ggtttaatat tatttattat tttgga                                 26


<210> SEQ ID NO 61
<211> LENGTH: 25
<212> TYPE: DNA
<213> ORGANISM: Artificial sequence
<220> FEATURE:
<223> OTHER INFORMATION: Synthetic Construct - amplification primer

<400> SEQUENCE: 61

ctcttacctt cctatactct ctaaa                                  25


<210> SEQ ID NO 62
<211> LENGTH: 28
<212> TYPE: DNA
<213> ORGANISM: Artificial sequence
<220> FEATURE:
<223> OTHER INFORMATION: Synthetic Construct - amplification primer

<400> SEQUENCE: 62

agagtgtagt tgtaagattt aatagagt                               28
```

METHOD FOR IN VITRO DIAGNOSIS OR PROGNOSIS OF TESTICULAR CANCER

This is a continuation of application Ser. No. 13/739,447 filed Jan. 11, 2013, which is a continuation of application Ser. No. 13/138,000 filed Sep. 23, 2011, which is a continuation of application Ser. No. 12/918,166 filed Aug. 18, 2010, which is a National Stage Application of PCT/FR2009/050390 filed Mar. 10, 2009, and claims the benefit of French Application No. 0851619 filed Mar. 12, 2008. The entire disclosures of the prior applications are hereby incorporated by reference in their entirety.

Testicular cancer represents 1 to 2% of cancers in men, and 3.5% of urological tumors. It is the most common tumor in young men, and rare before 15 years of age and after 50 years of age. The risk is highest in patients who are seropositive for HIV. Seminoma is the most common form of testicular cancer (40%), but many other types of cancer exist, among which are embryonic carcinoma (20%), teratocarcinoma (30%) and choriocarcinoma (1%).

The diagnosis of testicular cancer is first clinical: it often presents in the form of a hard and irregular swelling of the testicle. An ultrasound confirms the intratesticular tumor and Doppler ultrasound demonstrates the increase in vascularization in the tumor. In some cases, a magnetic resonance examination (testicular MRI) can be useful. A thoracic, abdominal and pelvic scan makes it possible to investigate whether there is any lymph node involvement of the cancer. A blood sample for assaying tumor markers is virtually systematic. It makes it possible to orient the diagnosis of the type of tumor. Two main tumor markers are used and assayed in the blood: β-HCG and α-foetoprotein. However, these markers are not very specific and, furthermore, if the concentration of these markers is at physiological levels, this does not mean that there is an absence of tumor. At the current time, the final diagnosis and final prognosis are given after ablation of the affected testicle (orchidectomy), which constitutes the first stage of treatment. Next, depending on the type of cancer and on its stage, a complementary treatment by radiotherapy or chemotherapy is applied. There is therefore a real need for having markers which are specific for testicular cancer and which, in addition, make it possible to establish as early a diagnosis and prognosis as possible.

The rare event represented by the infection of a germline cell by an exogenous provirus results in the integration, into the host's genome, of a proviral DNA or provirus, which becomes an integral part of the genetic inheritance of the host. This endogenous provirus (HERV) is therefore transmissible to the next generation in Mendelien fashion. It is estimated that there are approximately a hundred or so HERV families representing approximately 8% of the human genome. Each of the families has from several tens to thousands of loci, which are the result of intracellular retrotranspositions of transcriptionally active copies. The loci of the contemporary HERV families are all replication-defective, which signifies loss of the infectious properties and therefore implies an exclusively vertical (Mendelien) transmission mode.

HERV expression has been particularly studied in three specific contexts, placentation, autoimmunity and cancer, which are associated with cell differentiation or with the modulation of immunity. It has thus been shown that the envelope glycoprotein of the ERVWE1 locus of the HERV-W family is involved in the fusion process resulting in syncytiotrophoblast formation. It has, moreover, been suggested that the Rec protein, which is a splice variant of the env gene of HERV-K, could be involved in the testicular tumorogenesis process. However, the following question has not yet been answered: are HERVs players or markers in pathological contexts?

The present inventors have now discovered and demonstrated that nucleic acid sequences belonging to loci of the HERV-W family are associated with testicular cancer and that these sequences are molecular markers for the pathological condition. The sequences identified are either proviruses, i.e. sequences containing all or part of the gag, pol and env genes flanked on the 5' and on the 3' by long terminal repeats (LTRs), or isolated LTRs. The DNA sequences identified are respectively referenced as SEQ ID Nos. 1 to 6 in the sequence listing.

The subject of the present invention is therefore a method for in vitro, diagnosis or prognosis of testicular cancer, in a biological sample from a patient suspected of suffering from testicular cancer, which comprises a step of detecting at least one expression product from at least one nucleic acid sequence of the endogenous retroviral family called HERV-W, said sequence being selected from the sequences identified in SEQ ID Nos. 1 to 6 or from the sequences which exhibit at least 99% identity, preferably at least 99.5% identity, and advantageously at least 99.6% identity, with one of the sequences identified in SEQ ID Nos. 1 to 6.

The percentage identity described above has been determined while taking into consideration the nucleotide diversity in the genome. It is known that nucleotide diversity is higher in the regions of the genome that are rich in repeat sequences than in the regions which do not contain repeat sequences. By way of example, D. A. Nickerson et al.,[1] have shown a diversity of approximately 0.3% (0.32%) in regions containing repeat sequences.

The expression product which is detected is preferably at least one mRNA transcript of at least one of the sequences SEQ ID Nos. 1 to 6, but this can also be a polypeptide which is the product of translation of at least one of said transcripts.

When the expression product is an mRNA transcript, it is detected by any suitable method, such as hybridization, sequencing or amplification. The mRNA can be detected directly by bringing it into contact with at least one probe and/or at least one primer which are designed so as to hybridize, under predetermined stringency conditions, to the mRNA transcripts, demonstrating the presence or absence of hybridization to the mRNA and, optionally, quantifying the mRNA. Among the preferred methods, mention may be made of amplification (for example, RT-PCR, NASBA, etc.) or else Northern blotting. The mRNA can also be detected indirectly on the basis of nucleic acids derived from said transcripts, such as cDNA copies, etc.

Generally, the method of the invention comprises an initial step of extracting the mRNA from the sample to be analyzed.

First, the method can comprise:

(i) a step of extracting the mRNA from the sample to be analyzed, (ii) a step of detecting and quantifying the mRNA of the sample to be analyzed, (iii) a step of extracting the mRNA from a healthy sample, (iv) a step of detecting and quantifying the mRNA of the healthy sample, (v) a step of comparing the amount of mRNA expressed in the sample to be analyzed and in the healthy sample; if the amount of mRNA expressed in the sample to be analyzed is determined as being greater than the amount of mRNA expressed in the healthy sample, this can be correlated with the diagnosis or prognosis of a testicular cancer;

and in particular:

(i) extraction of the RNA to be analyzed from the sample, (ii) determination, in the RNA to be analyzed, of a level of expression of at least one RNA sequence in the sample, said RNA sequence being the product of transcription of at least one nucleic acid sequence selected from the sequences identified in SEQ ID Nos. 1 to 6 or from the sequences which include at least 99% identity, preferably at least 99.5% identity, and advantageously at least 99.6% identity, with one of the sequences identified in SEQ ID Nos. 1 to 6, and (iii) comparison of the level of expression of said RNA sequence(s) defined in (ii) with the level of expression of said RNA sequence(s) in a noncancerous biological sample; if the level of expression of the RNA to be analyzed is determined as being greater than the level of expression of the RNA extracted from the noncancerous biological sample, this can be correlated with the diagnosis or prognosis of a testicular cancer.

The transcripts are overexpressed in testicular tumors. In order to detect such an overexpression, a reference point may be necessary, i.e. a control. The amount of mRNA in the healthy sample serves as a reference standard to which the amount of mRNA in the sample to be analyzed can be compared, it being possible for an overexpression of mRNA in the sample to be analyzed, compared with the expression of mRNA in the healthy sample, to be correlated with a diagnosis or prognosis of a testicular cancer. However, since transcription is generally negligible or even nonexistent in the healthy sample, whereas it is significantly higher in the cancer sample, a reference point is not essential, the significant expression of transcripts being an indicator of the disease.

The term "overexpressed sequence" is intended to mean an mRNA sequence which is found in greater amounts or at higher levels than those found for the same mRNA sequence derived from the same type of sample, but which is noncancerous, constituting the reference threshold value.

The sequences of said transcripts are respectively identified in SEQ ID Nos. 7 to 12 (given with reference to the genomic DNA):

SEQ ID No. 7=transcript of the HW4TT locus,

SEQ ID No. 8=transcript of the HW2TT locus,

SEQ ID No. 9=transcript of the HW13TT locus,

SEQ ID No. 10=transcript of the HWXTT locus,

SEQ ID No. 11=transcript of the HW21TT locus,

SEQ ID No. 12=transcript of the ERVWE1 locus.

When the expression product is a polypeptide derived from the translation of at least one of the transcripts, it can be detected, in the method of the invention, using at least one binding partner specific for said polypeptide, in particular an antibody, for example a monoclonal antibody. The method for producing monoclonal antibodies and the selection process are well known to those skilled in the art.

By way of illustration, polypeptide sequences are described and identified in SEQ ID Nos. 14, 16, 18, 20, 22 and 24:

SEQ ID No. 14=Gag protein of HW4TT,

SEQ ID No. 16=protease of HW4TT,

SEQ ID No. 18=Gag protein of HW2TT,

SEQ ID No. 20=protein of HW2TT,

SEQ ID No. 22=Gag protein of HW13TT,

SEQ ID No. 24=Gag protein of HW21TT

SEQ ID No. 26=Env protein of ERVWE1 (Syncytin-1).

The sample from the patient will generally comprise cells (such as the testicular cells).

They may be present in a tissue sample (such as the testicular tissue) or be found in the circulation. In general, the sample is a testicular tissue extract or a biological fluid, such as blood, serum, plasma, urine or else seminal fluid.

The subject of the invention is also an isolated nucleic acid sequence which consists of:

(i) at least one DNA sequence selected from the sequences SEQ ID Nos. 1 to 6, or (ii) at least one DNA sequence complementary to a sequence selected from the sequences SEQ ID Nos. 1 to 6, or (iii) at least one DNA sequence which exhibits at least 99% identity, preferably at least 99.5% identity, and advantageously at least 99.6% identity, with a sequence as defined in (i) and (ii), or (iv) at least one RNA sequence which is the product of transcription of a sequence selected from the sequences as defined in (i), or (v) at least one RNA sequence which is the product of transcription of a sequence selected from the sequences which exhibit at least 99% identity, preferably at least 99.5% identity, and advantageously at least 99.6% identity, with a sequence as defined in (i), or (vi) at least one RNA sequence selected from the sequences SEQ ID Nos. 7 to 12; and the use of at least one isolated nucleic acid sequence, as a molecular marker for in vitro diagnosis or prognosis of testicular cancer, in which the nucleic acid sequence consists of:

(i) at least one DNA sequence selected from the sequences SEQ ID Nos. 1 to 6, or (ii) at least one DNA sequence complementary to a sequence selected from the sequences SEQ ID Nos. 1 to 6, or (iii) at least one DNA sequence which exhibits at least 99% identity with a sequence as defined in (i) and (ii), or (iv) at least one RNA sequence which is the product of transcription of a sequence selected from the sequences as defined in (i), or (v) at least one RNA sequence which is the product of transcription of a sequence selected from the sequences which exhibit at least 99% identity with a sequence as defined in (i), or (vi) at least one RNA sequence selected from the sequences SEQ ID Nos. 7 to 12.

FIGURES

Figure 4:
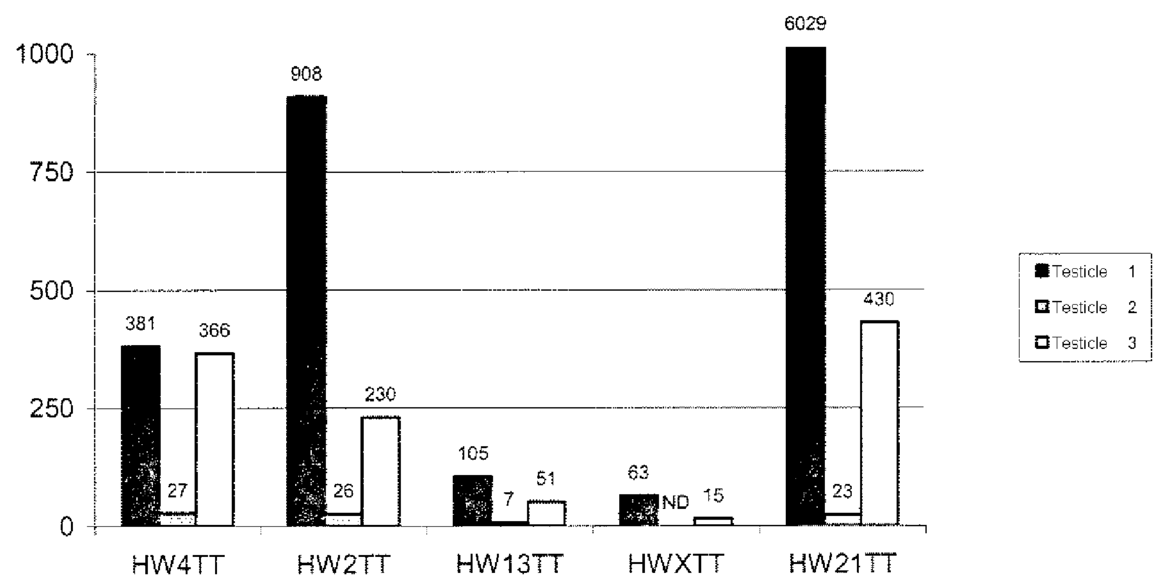
Figure 5:
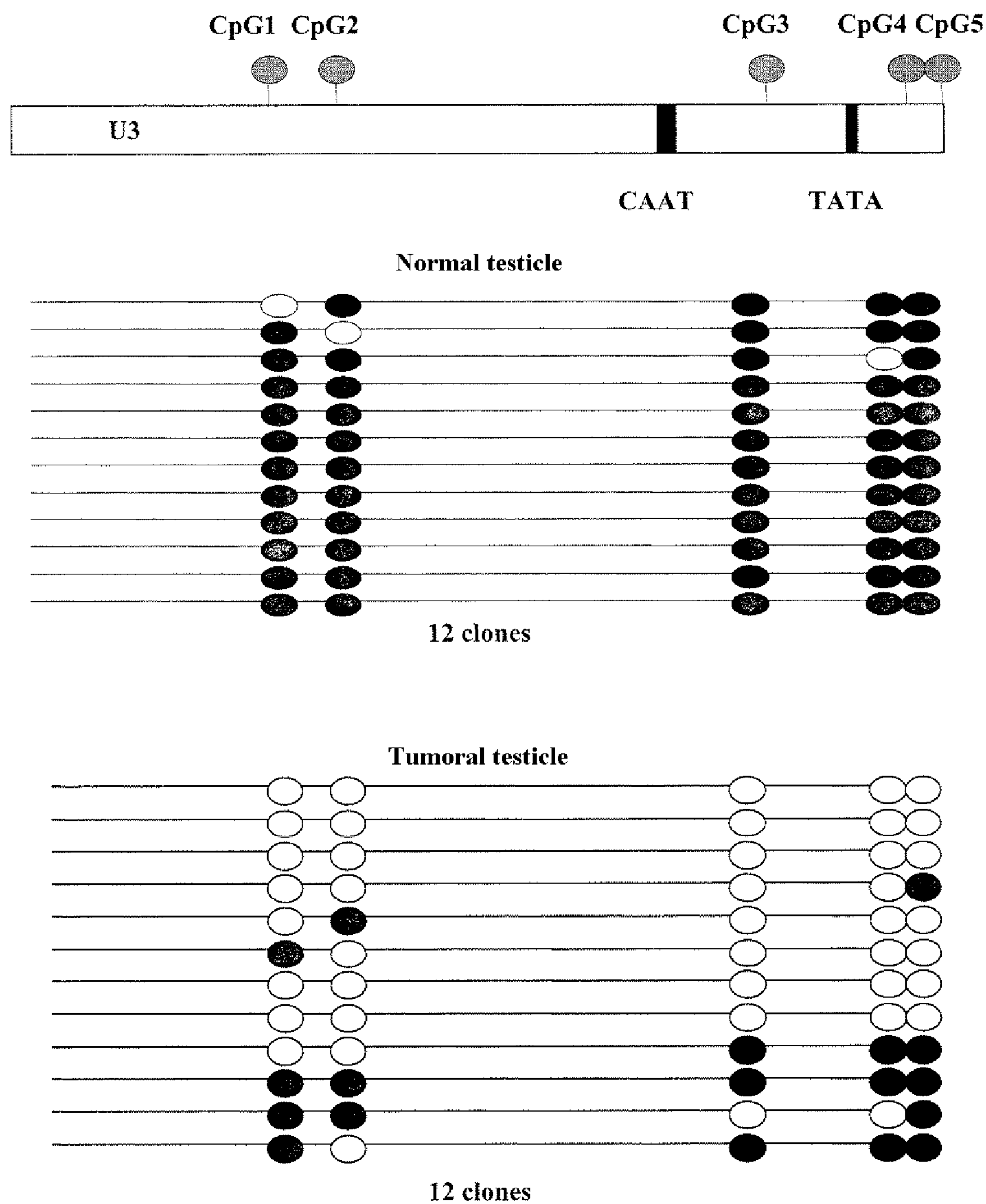
Figure 6:
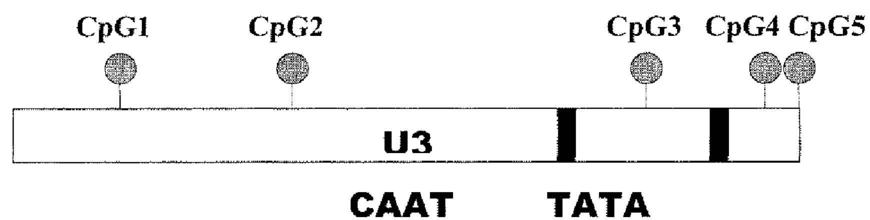
Figure 6:
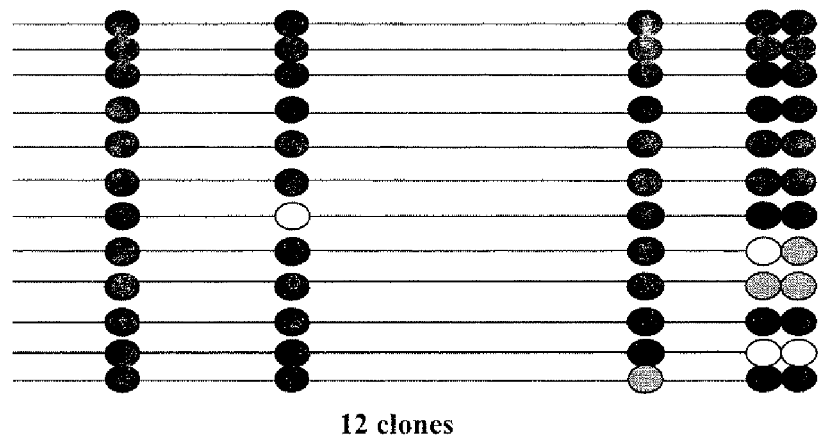
Figure 6:
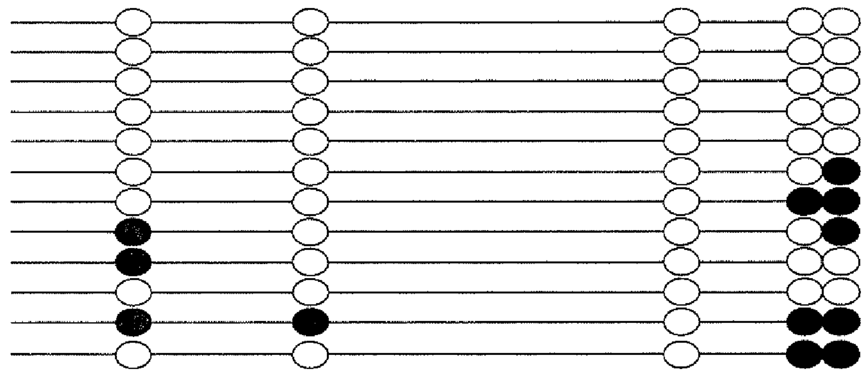
Figure 7:
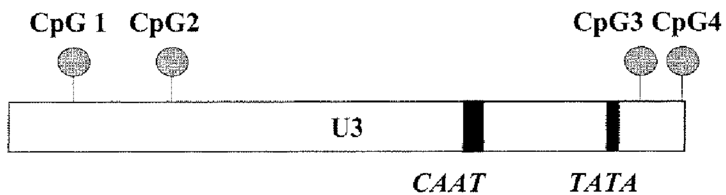
Figure 7:
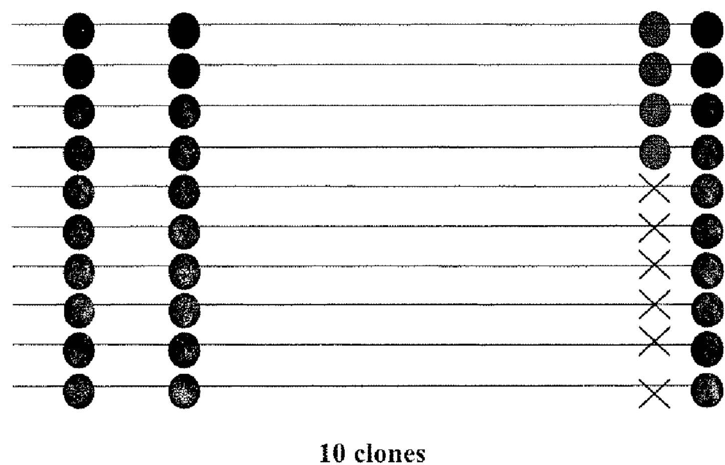
Figure 7:
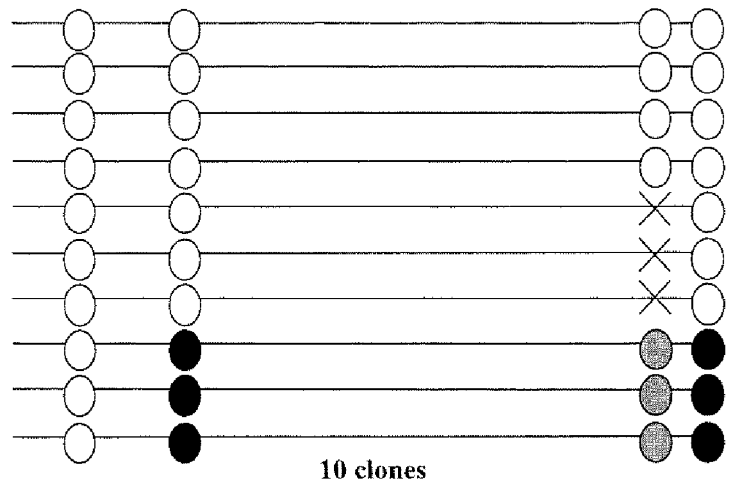
Figure 8:
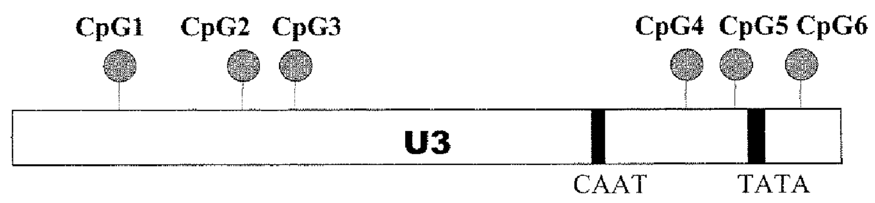
Figure 8:
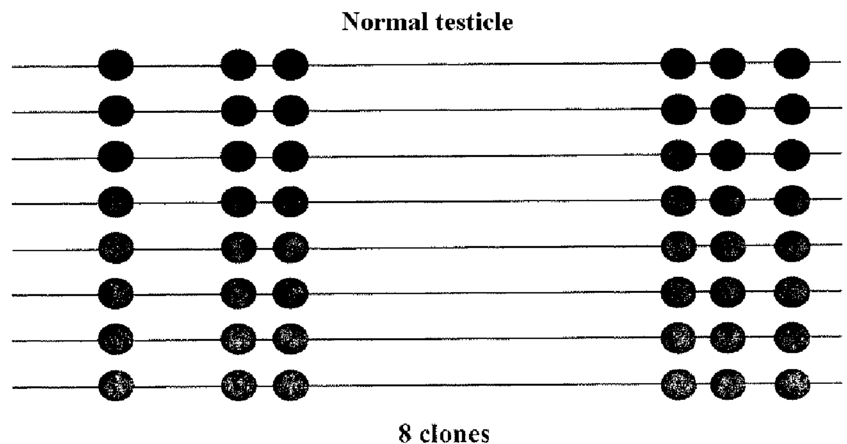
Figure 8:
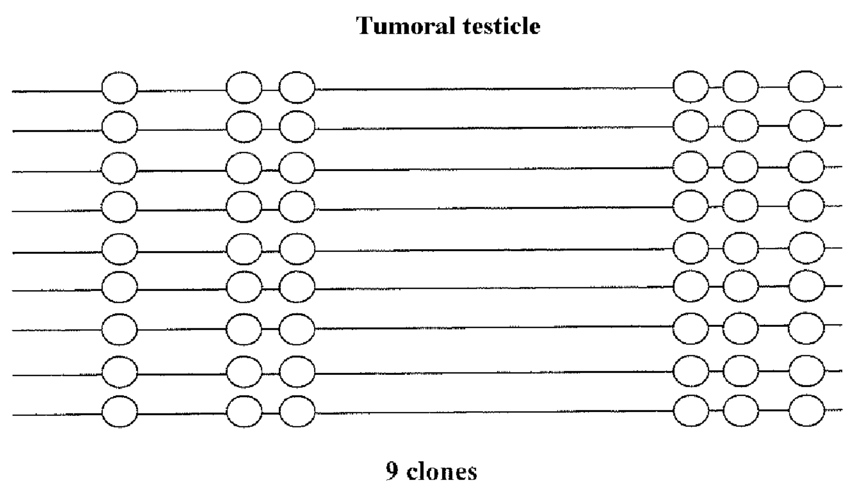
Figure 9:
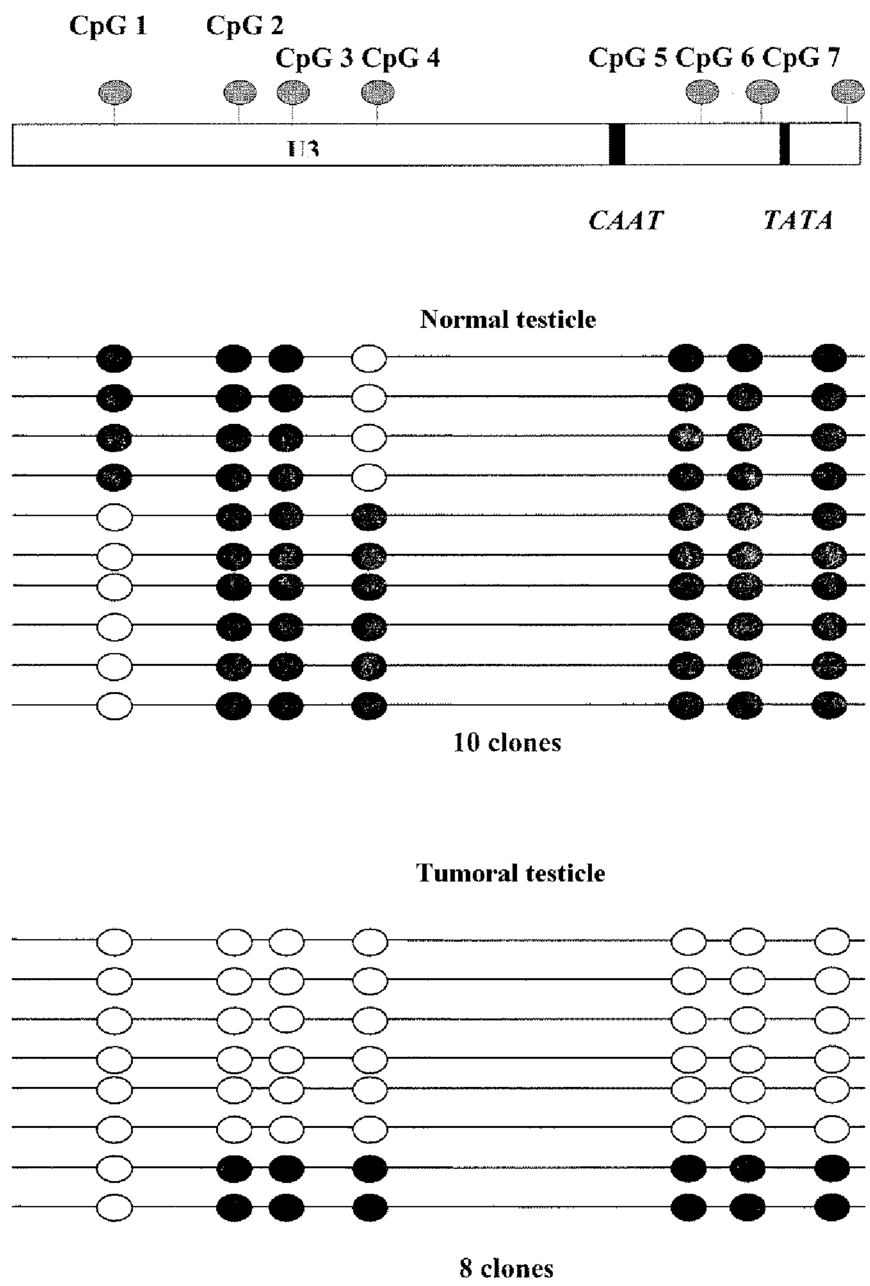
Figure 10:
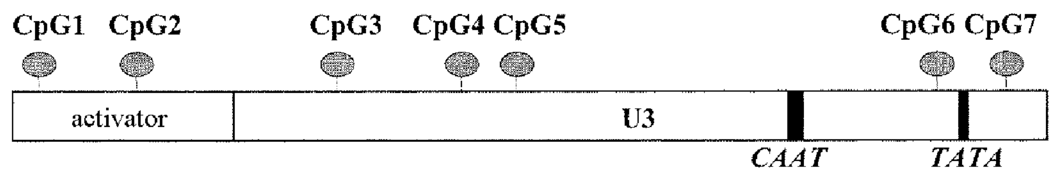
Figure 10:
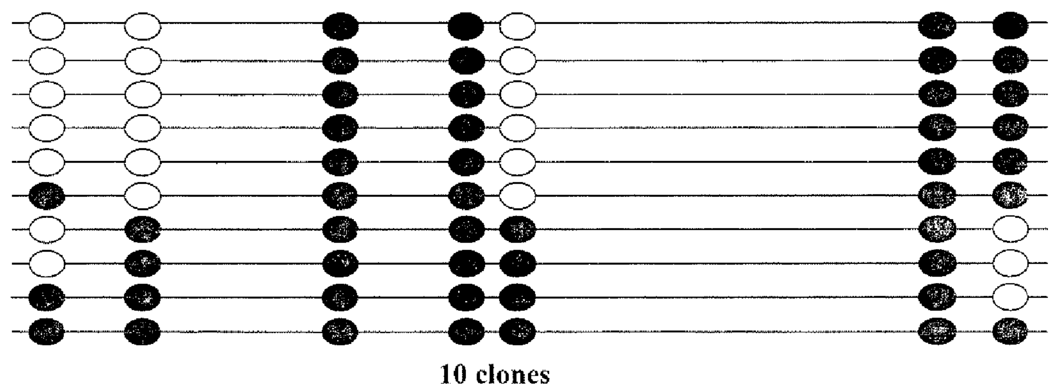
Figure 10:
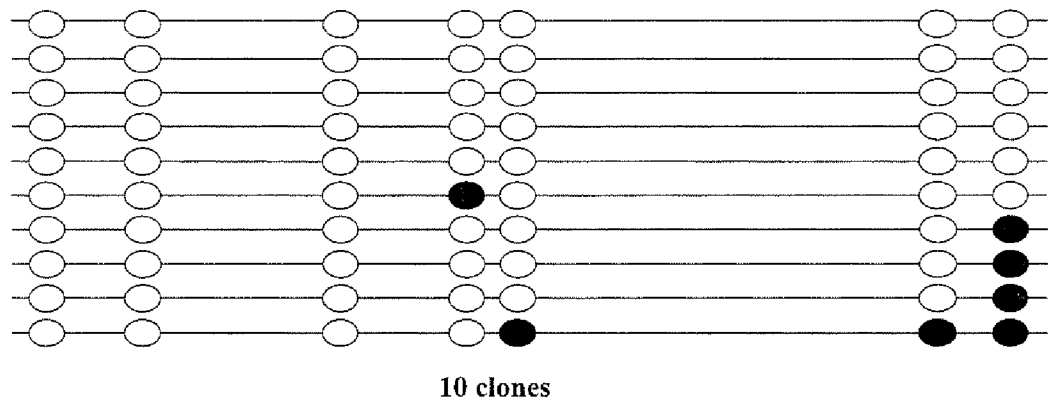

FIG. 4 is a histogram representing the increase in expression of the five loci (HW4TT, HW2TT, HW13TT, HWXTT and HW21TT), respectively, in three pairs of testicular samples (testicle 1, testicle 2 and testicle 3), based on a comparative tumor sample/healthy sample quantification. The loci are represented along the x-axis and the factors of increase of expression between tumor tissue and healthy tissue are represented along the y-axis.

FIGS. 5 to 10 represent the methylation status of the U3 region of unique LTR or of the 5' LTR of the various loci, respectively HW4TT, HW2TT, HW13TT, HWXTT, HW21TT and ERVWE1 in the healthy testicle (normal) and in the tumoral testicle derived from the same patient, after amplification and analysis of the sequences obtained.

EXAMPLES

Example 1: Identification of HERV-W Loci Expressed in Cancerous Tissues

Method:

The identification of expressed HERV-W loci is based on the design of a high-density DNA chip in the GeneChip format proposed by the company Affymetrix. It is a specially developed, custom-made chip, the probes of which correspond to HERV-W loci. The sequences of the HERV-W family were identified from the GenBank nucleic databank using the Blast algorithm (Altschul et al., 1990) with the sequence of the ERVWE1 locus, located on chromosome 7 at 7q21.2 and encoding the protein called syncytin. The sequences homologous to HERV-W were compared to a library containing reference sequences of the HERV-W family (ERVWE1) cut up into functional regions (LTR, gag, pol and env), using the RepeatMasker software (A. F. A. Smit and P. Green). These elements constitute the HERVgDB bank.

The probes making up the high-density chip were defined on a criterion of uniqueness of their sequences in the HERVgDB bank. The HERV-W proviral and solitary LTRs contained in the HERVgDB bank were extracted. Each of these sequences was broken down into a set of sequences of 25 nucleotides (25-mers) constituting it, i.e. as many potential probes. The evaluation of the uniqueness of each probe was carried out by means of a similarity search with all the 25-mers generated for all the LTRs of the family under consideration. This made it possible to identify all the 25-mers of unique occurrence for each family of HERV. Next, some of these 25-mers were retained as probes. For each U3 or U5 target region, a set of probes was formed on the basis of the probes identified as unique.

Figure 1:
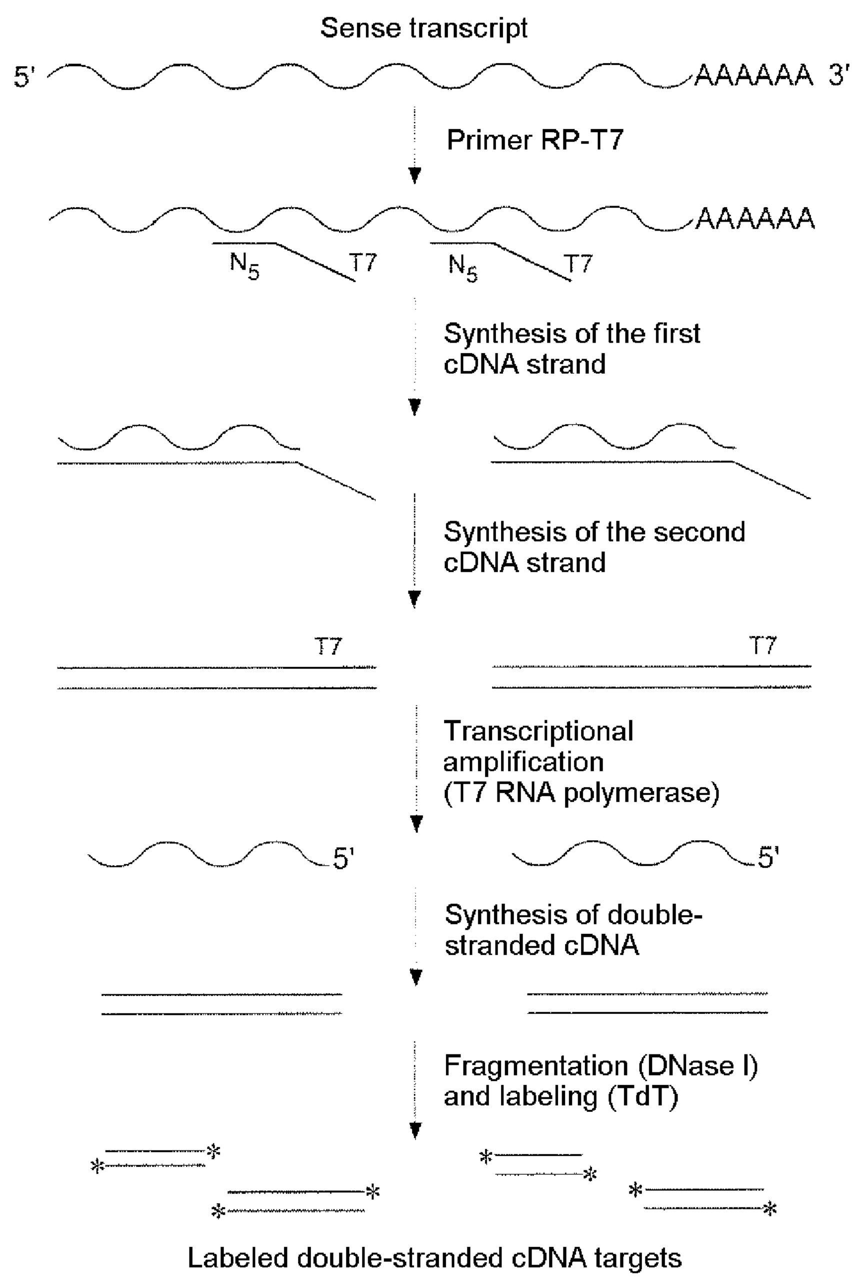
FIG. 1 represents the principle of the WTA method for amplifying RNAs.

The samples analyzed using the HERV high-density chip correspond to RNAs extracted from tumors and to RNAs extracted from the healthy tissues adjacent to these tumors. The tissues analyzed are: uterus, colon, lung, breast, testicle, prostate and ovary. Placental RNAs (health tissue only) were also analyzed. For each sample, 400 ng of total RNA were amplified by means of an unbiased transcriptional method known as WTA. The principle of WTA amplification is the following: primers (RP-T7) comprising a random sequence and a T7 promoter sequence are hybridized to the transcripts; double-standard cDNAs are synthesized and serve as a template for transcriptional amplification by the T7 RNA polymerase; the antisense RNAs generated are converted to double-stranded cDNAs which are then fragmented and labeled by introducing biotinylated nucleotide analogs at the 3'OH ends using terminal transferase (TdT) (cf. FIG. 1).

Figure 2:
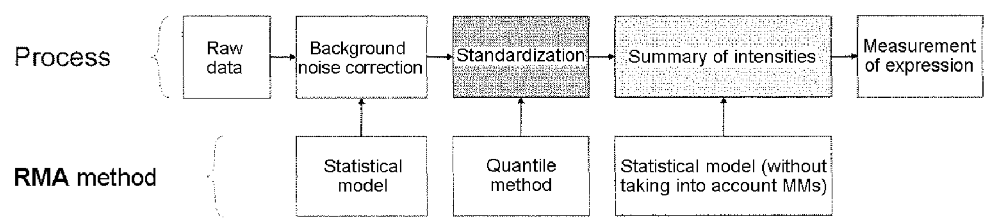
FIG. 2 represents a synoptic scheme of the nature and the sequence of the various steps for preprocessing DNA-chip data according to the RMA method.

For each sample, 16 μg of biotin-labeled amplification products were hybridized to a DNA chip according to the protocol recommended by the company Affymetrix. The chips were then washed and labeled, according to the recommended protocol. Finally, the chips were read by a scanner in order to acquire the image of their fluorescence. The image analysis carried out using the GCOS software makes it possible to obtain numerical values of fluorescence intensity which are preprocessed according to the RMA method (cf.: FIG. 2) before being able to carry out a statistical analysis in order to identify the HERV loci specifically expressed in certain samples.

Comparison of the means of more than two classes of samples was carried out by the SAM procedure applied to a Fisher test.

Figure 3:
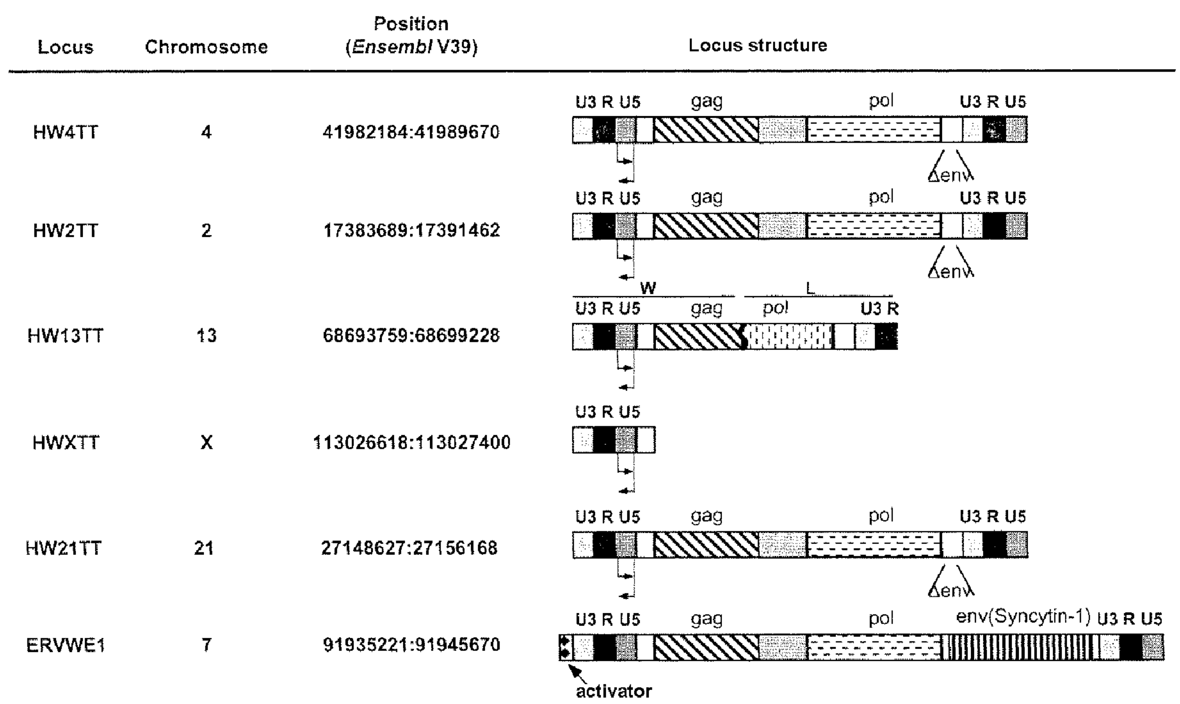
FIG. 3 illustrates the nomenclature, the position and the structure of the HERV-W loci overexpressed and exhibiting a loss of methylation in the tumoral testicle.

Results:

The processing of the data generated by the analysis on DNA chip using this method made it possible to identify six sets of probes corresponding to an overexpression in just one sample: the tumoral testicle. These five sets of probes are specific for six precise loci referenced HW4TT, HW2TT, HW13TT, HWXTT, HW21TT and ERVWE1 (cf.: FIG. 3). These six loci therefore represent markers for testicular cancer. Their nucleotide sequences are respectively identified in SEQ ID Nos. 1 to 6 in the sequence listing and the nucleotide sequences of their respective transcripts are identified in SEQ ID Nos. 7 to 12 in the sequence listing.

The information relating to the abovementioned six loci are summarized in Table 1 below.

TABLE 1

| Locus | SEQ ID No: | Chromosome | Position* |
|---|---|---|---|
| HW4TT | 1 | 4 | 41982184:41989670 |
| HW2TT | 2 | 2 | 17383689:17391462 |
| HW13TT | 3 | 13 | 68693759:68699228 |
| HWXTT | 4 | X | 113026618:113027400 |
| HW21TT | 5 | 21 | 27148627:27156168 |
| ERVWE1 | 6 | 7 | 91935221:91945670 |

*Position relative to ensemble version No. 39 (June 2006) (NCBI No. 36) http: //www.ensembl.org/*Homo_sapiens*/index.html The HW13TT locus is a chimeric provirus of HERV-W/L type resulting from the recombination of an HERV-W provirus and an HERV-L provirus. This chimera is such that the 5' region made up of the sequence starting from the beginning of the 5' LTR to the end of the determined gag fragment is of W type and the 3' region made up of the sequence starting from the subsequent pol fragment to the end of the 3' LTR (U3-R only) is of L type. This results in a fusion of the 3' gag W-5' pol L regions.

A search of open reading frames (ORFs) of at least 150 bases, using the Mac Vector 9.5.2 software, based on the identification of a start codon and of a stop codon, was carried out and the corresponding polypeptides identified.

The ORF1 of HW4TT identified in SEQ ID No. 13 encodes a Gag protein identified in SEQ ID No. 14 and the ORF 2 of HW4TT (SEQ ID No. 15) encodes a protease (SEQ ID No. 16), the ORF1 of HW2TT identified in SEQ ID No. 17 encodes a Gag protein identified in SEQ ID No. 18 and the ORF 2 of HW2TT (SEQ ID No. 19) encodes a protein identified in SEQ ID No. 20, the ORF of HW13TT identified in SEQ ID No. 21 encodes a Gag protein identified in SEQ ID No. 22, the ORF of HW21TT identified in SEQ ID No. 23 encodes a Gag protein identified in SEQ ID No. 24, the ORF of ERVWE1 identified in SEQ ID No. 25 encodes an Env protein identified in SEQ ID No. 26.

Example 2: Validation of the Loci Overexpressed in the Tumoral Testicle and Determination of the Associated Induction Factor Principle:

Five of the six loci identified as overexpressed in the tumoral testicle by means of the high-density HERV chip were validated by real-time RT-PCR on three pairs of testicular samples. The specificity of this overexpression is evaluated by analyzing samples originating from other tissues. To this end, specific amplification systems were developed and used for the loci identified, as described in Table 2 below.

TABLE 2

| Locus | Sense primer (SEQ ID No:) | Antisense primer (SEQ ID No:) |
|---|---|---|
| G6PD gene | TGCAGATGCTGTGTCTGG (27) | CGTACTGGCCCAGGACC (28) |
| HW4TT | GGTTCGTGCTAATTGAGCTG (29) | ATGGTGGCAAGCTTCTTGTT (30) |
| HW2TT | TGAGCTTTCCCTCACTGTCC (31) | TGTTCGGCTTGATTAGGATG (32) |
| HW13TT | CATGGCCCAATATTCCATTC (33) | GGTCCTTGTTCACAGAACTCC (34) |
| HWXTT | CCGCTCCTGATTGGACTAAA (35) | CGTGGGTCAAGGAAGAGAAC (36) |
| HW21TT | ATGACCCGCAGCTTCTAACAG (37) | CTCCGCTCACAGAGCTCCTA (38) |

The expression of these loci is standardized with respect to that of a suitable housekeeping gene: G6PD. This quantification of expression was carried out using an Mx3005P real-time RT-PCR machine, marketed by the company Stratagene.

Results:

The study of the three pairs of testicular samples indicates that the five loci identified, with the exception of HWXTT, the expression of which could not be quantified in the second testicular RNA pair, are overexpressed in the tumoral testicle compared with the health tissue (cf.: FIG. 4). The very marked nature of the overexpression, i.e. a low or even absent transcriptional expression in the healthy testicle and a high expression in the tumoral testicle, reveals the possibility of an epigenic method of regulation of transcription of these loci.

The analysis of pairs of samples originating from other tissues (colon, uterus, breast, ovary, lung and prostate) shows that the overexpression phenomenon is restricted to the tumoral testicle. Consequently, the expression of the identified loci assumes the nature of a marker specific for testicular cancer.

Example 3: Epigenetic Control of Transcription

Principle:

DNA methylation is an epigenetic modification which takes place, in eukaryotics, by the addition of a methyl group to the cytosines of 5'-CpG dinucleotides, and results in transcriptional repression when this modification occurs within the nucleotide sequence of a promoter. Apart from a few exceptions, human endogenous sequences of retroviral origin are restricted, owing to this methylation process, to a silent transcriptional state in the cells of the organism under physiological conditions.

In order to analyze the methylation status of the unique LTR or of the 5' LTR of the five loci, the "bisulfite sequencing PCR" method was used. This method makes it possible, on the basis of sequencing a representative sample of the population, to identify the methylation state of each CG dinucleotide on each of the sequences within the tissue studied.

Since the methylation information is lost during the amplification steps, it is advisable to translate the methylation information actually within the nucleotide sequence by means of the method of treating the genomic DNA with sodium bisulfite. The action of the bisulfite (sulfonation), followed by hydrolytic deamination and then alkaline desulfonation, in fact makes it possible to modify all the cytosines contained in the genomic DNA, into uracil. The speed of deamination of sulfonated cytosines (C) is, however, much higher than that of the sulfonated 5-methyl-Cs. It is therefore possible, by limiting the reaction time to 16 hours, to convert strictly the non-methylated cytosines to uracil (U), while at the same time preserving the cytosines which have a methyl group. After the sodium bisulfite treatment, the sequence of interest is amplified from the genomic DNA derived from the tumoral testicular section and from that derived from the adjacent healthy testicular section, by polymerase chain reaction (PCR) in two stages. The first PCR enables a specific selection of the sequence of interest, the second, "nested", PCR makes it possible to amplify this sequence.

Since the DNA sequence had been modified by the bisulfite, the design of the primers took into account the code change (C to U), and the primers were selected so as to hybridize to a region containing no CpG (their methylation state, and therefore their conversion state, being a priori unknown).

The sequences of the primers used are described in Tables 3 to 8 below.

TABLE 3

| HW4TT locus | | |
|---|---|---|
| Amplification | Sense primer 5'→3' (SEQ ID No.:) | Antisense primer 5'→3' (SEQ ID No.:) |
| First PCR | CCAACATCACTAACACAACCT (39) | GGGAGTTAGTAAGGGGTTTG (40) |
| Nested PCR | CAACCTATTAAACAAAACTAAATT (41) | AGATTTAATAGAGTGAAAATAGAGTTT (42) |

TABLE 4

| HW2TT locus | | |
|---|---|---|
| Amplification | Sense primer 5'→3' (SEQ ID No.:) | Antisense primer 5'→3' (SEQ ID No.:) |
| First PCR | TTATTAGTTTAGGGGATAGTTG (43) | ACACAATAAACAACCTACTAAAT (44) |
| Nested PCR | GAGGGTAAGTGGTGATAAA (45) | AACCTACTAAATCCAAAAAAA (46) |

TABLE 5

| HW13TT locus | | |
|---|---|---|
| Amplification | Sense primer 5'→3' (SEQ ID No.:) | Antisense primer 5'→3' (SEQ ID No.:) |
| First PCR | TAGGATTTTAGGTTTATTGTTA (47) | AAAAATAAAATATTAAACC (48) |
| Nested PCR | ATATGTGGGAGTGAGAGATA (49) | CAACAACAAACAATAATAATAA (50) |

TABLE 6

| HWXTT locus | | |
|---|---|---|
| Amplification | Sense primer 5'→3' (SEQ ID No.:) | Antisense primer 5'→3' (SEQ ID No.:) |
| First PCR | TTGAGTTTTTTTATTGATAGTG (51) | TCTAAATCCTATTTTCCTACT (52) |
| Nested PCR | GTTTTTTTATTGATAGTGAGAGAT (53) | TAACAAACCTTTAATCCAAT (54) |

TABLE 7

| HW21TT locus | | |
|---|---|---|
| Amplification | Sense primer 5'→3' (SEQ ID No.:) | Antisense primer 5'→3' (SEQ ID No.:) |
| First PCR | TTTAGTGAGGATGATGTAATAT (55) | CAACTTAATAAAAATAAACCCA (56) |
| Nested PCR | ATAATGTTTTAGTAAGTGTTGGAT (57) | ACAATTACAAACCTTTAACC (58) |

TABLE 8

| ERVWE1 locus | | |
|---|---|---|
| Amplification | Sense primer 5'→3' (SEQ ID No.:) | Antisense primer 5'→3' (SEQ ID No.:) |
| First PCR | AATTCATTCAACATCCATTC (59) | GGTTTAATATTATTTATTATTTTGGA (60) |
| Nested PCR | CTCTTACCTTCCTATACTCTCTAAA (61) | AGAGTGTAGTTGTAAGATTTAATAGAGT (62) |

After extraction on a gel and purification, the amplicons are cloned into plasmids, and the latter are used to transform competent bacteria. About twelve plasmid DNA mini preparations are carried out using the transformed bacteria and the amplicons contained in the plasmids are sequenced. The sequences obtained are then analyzed (cf.: FIGS. 5 to 10).

Results:

The analysis of the 5' region of the transcripts of the loci identified was carried out by means of the 5' Race technique. It in particular made it possible to show that the transcription is started at the beginning of the R region of the proviral 5' LTR. This reflects the existence of a promoter role for the U3 region of the proviral 5' LTR.

1. Methylation State of the U3 Sequences of the 5' LTR of the HW4TT Locus:

The U3 sequence of the 5' LTR of the HW4TT locus of reference contains 5 CpG sites:

a) in the sample of healthy testicular tissue: out of 12 sequences analyzed, 9 are completely methylated. The other 3 each time exhibit 1 CpG nonmethylated out of the 5 contained in the U3 region. This therefore represents an overall methylation of the U3 region of the 5' LTR of the HW4TT locus amounting to 95% in the healthy testicular sample;

b) in the sample of tumoral testicular tissue: out of 12 sequences analyzed, 5 (i.e. 41.66% of the sequences) are completely demethylated, 3 sequences have 4 CpGs out of 5 nonmethylated, 2 sequences have 2 CpGs out of 5 nonmethylated, 1 sequence has 1 CpG out of 5 nonmethylated, and 1 sequence remains completely methylated. This therefore represents an overall methylation of the U3 region of the 5' LTR of the HW4TT locus amounting to 30% in the tumoral testicular sample.

2. Methylation State of the U3 Sequences of the 5' LTR of the HW2TT Locus:

The U3 sequence of the 5' LTR of the HW2TT locus of reference contains 5 CpG sites:

a) in the sample of healthy testicular tissue: out of 12 sequences analyzed, 9 are completely methylated, 1 has its 2nd CpG nonmethylated, 1 has the CpG at position 4 nonmethylated, 1 has the CpGs at positions 4 and 5 nonmethylated, and 3 sequences have point mutations on one or two CpGs (one in position 3, one in position 5 and one in positions 4 and 5), very probably reflecting PCR artifacts. This therefore represents an overall methylation of the U3 region of the 5' LTR of the HW2TT locus amounting to 92.9% in the healthy testicular sample;

b) in the sample of tumoral testicular tissue: out of 12 sequences analyzed, 6 are completely demethylated, 5 sequences have one or two methylated CpG(s) (1 at position 1, 1 other at position 5, 1 on positions 1 and 5, 2 at positions 4 and 5 and 1 at position 3). Finally, one sequence has 4 CpGs methylated out of 5 (positions 1, 2, 4 and 5). This corresponds to an overall methylation of the U3 region of the 5' LTR of the HW2TT locus amounting to 20% in the tumoral testicular sample.

3. Methylation State of the U3 Sequences of the 5' LTR of the HW13TT Locus:

The U3 sequence of the 5' LTR of the HW13TT locus of reference contains 3 CpG sites:

a) in the sample of healthy testicular tissue: an additional CpG, compared with the reference sequence, is found in 4 of the 10 clones studied for this locus. It is located between CpGs 2 and 3 and is methylated. In the other 6 clones, this site is mutated compared with the reference sequence. The other 3 CpGs of the U3 region are methylated in the 10 sequences analyzed. This therefore represents an overall methylation of the U3 region of the 5' LTR of the HW13TT locus amounting to 100% in the healthy testicular sample;

b) in the sample of tumoral testicular tissue: the additional CpG indicated above is also found. It is demethylated in 4 of the 10 sequences analyzed, mutated in 3 other sequences, and its methylation state is indeterminate in the last 3 sequences. 7 sequences out of 10 are completely demethylated and the other 3 are methylated on the $2^{nd}$ and on the $3^{rd}$ CpG. This corresponds to an overall methylation of the U3 region of the 5' LTR of the HW13TT locus amounting to 20% in the tumoral testicular sample.

4. Methylation State of the U3 Sequences of the Solitary LTR of the HWXTT Locus:

The U3 sequence of the 5' LTR of the HWXTT locus of reference contains 6 CpG sites:

a) in the sample of healthy testicular tissue: the 8 sequences analyzed are completely methylated, which corresponds to a methylation percentage of 100% in the healthy testicular sample;

b) in the sample of tumoral testicular tissue: the 9 sequences analyzed 6 are completely demethylated, which corresponds to a methylation percentage of 0%.

5. Methylation State of the U3 Sequences of the 5' LTR of the HW21TT Locus:

The U3 sequence of the 5' LTR of the HW21TT locus of reference contains 7 CpG sites:

a) in the sample of healthy testicular tissue: the 10 sequences analyzed all have 6 CpGs methylated out of 7; for 6 of the sequences, the $1^{st}$ CpG is nonmethylated and for the other 4 sequences, the $4^{th}$ CpG is nonmethylated. This therefore represents an overall methylation of the U3 region of the 5' LTR of the HW21TT locus amounting to 85.7% in the healthy testicular sample;

b) in the sample of tumoral testicular tissue: out of 8 sequences analyzed, 6 are completely demethylated, 2 others exhibit a profile identical to one of those found in the healthy testicular tissue, namely 6 CpGs methylated and the $1^{st}$ CpG nonmethylated. This corresponds to an overall methylation of the U3 region of the 5' LTR of the HW21TT locus amounting to 21.4% in the tumoral testicular sample.

6. Methylation State of the Sequences of the Activator of the U3 of the 5' LTR of the ERVWE1 Locus:

The ERVWE1 locus comprises, in addition to its U3 promoter region, a known activator located directly upstream of the 5' LTR, and which contains two CpG sites (CpG 1 and 2). The U3 sequence of the 5' LTR of the ERVWE1 locus of reference contains, for its part, 5 CpG sites (CpGs 3 to 7):

a) in the sample of healthy testicular tissue: out of 10 sequences analyzed, 5 sequences have CpGs 1 and 2 (activator) and 5 (U3) nonmethylated, 1 sequence has CpGs 2 and 5 nonmethylated, 2 sequences have CpGs 1 (activator) and 7 (U3) nonmethylated, 1 sequence has CpG 7 only nonmethylated and, finally, 1 is completely methylated for the 7 CpGs. In total, this corresponds to a methylation percentage of 68.57% in the healthy testicular sample;

b) in the sample of tumoral testicular tissue: out of the 10 sequences analyzed, only 3 sequences exhibit, for each one, a unique methylated CpG (CpG 4 or CpG5 or CpG6), the other 7 sequences are completely demethylated, which corresponds to a methylation percentage of 4.29%.

The very high level of methylation of the U3 retroviral promoters of the loci considered, in the healthy tissue, is correlated with the low, or even absent, transcription expression of the U5 regions which correspond to the loci considered, indicating a repression of the transcriptional expression by an epigenetic mechanism. On the other hand, the low level of methylation of these same promoters in the tumoral tissue reflects a lifting of transcriptional inhibition, the result of which is the significantly higher expression demonstrated by means of the high-density HERV DNA chip and by means of the real-time RT-PCR.

LITERATURE REFERENCES

[1] Nickerson D. A. et al., DNA sequence diversity in a 9.7-kb region of the human lipoprotein lipase gene, Nature Genetics, Vol. 19, pp 233-240 (1998).

[2] Cottrell S. E., Molecular diagnostic applications of DNA methylation technology, Clinical Biochemistry 37, pp 595-604 (2004).

The invention claimed is:

1. A method of diagnosing and treating testicular cancer, comprising:

obtaining a testicular sample that is collected from a person suspected of suffering from testicular cancer;

assaying the testicular sample to detect whether one or more HERV-W mRNA transcripts are overexpressed; and diagnosing the person with testicular cancer when there is overexpression of the one or more HERV-W mRNA, transcripts; and treating the person with testicular cancer by performing any of orchidectomy, radiotherapy, or chemotherapy, wherein overexpression is detected when expression of the respective HERV-W mRNA transcript is increased as compared to expression of the respective HERV-W mRNA transcript in a healthy testicular sample and the one or more HERV-W mRNA transcripts are expressed from a genomic sequence having at least 99% sequence identity with any of SEQ ID NOS: 1-6.

2. The method of claim 1, wherein overexpression of the one or more HERV-W mRNA transcripts is detected by detecting cDNA obtained from the one or more HERV-W mRNA transcripts.

3. The method of claim 1, wherein the person has a hard and irregular swelling of a testicle.

4. The method of claim 1, comprising assaying the testicular sample to detect whether an HERV-W mRNA transcript is overexpressed from a genomic sequence having at least 99% sequence identity with SEQ ID NO: 1.

5. The method of claim 1, comprising assaying the testicular sample to detect whether an HERV-W mRNA transcript is overexpressed from a genomic sequence having at least 99% sequence identity with SEQ ID NO: 2.

6. The method of claim 1, comprising assaying the testicular sample to detect whether an HERV-W mRNA transcript is overexpressed from a genomic sequence having at least 99% sequence identity with SEQ ID NO: 3.

7. The method of claim 1, comprising assaying the testicular sample to detect whether an HERV-W mRNA transcript is overexpressed from a genomic sequence having at least 99% sequence identity with SEQ ID NO: 4.

8. The method of claim 1, comprising assaying the testicular sample to detect whether an HERV-W mRNA transcript is overexpressed from a genomic sequence having at least 99% sequence identity with SEQ ID NO: 5.

9. The method of claim 1, comprising assaying the testicular sample to detect whether an HERV-W mRNA transcript is overexpressed from a genomic sequence having at least 99% sequence identity with SEQ ID NO: 6.

10. The method of claim 1, comprising assaying the testicular sample to detect whether an HERV-W mRNA transcript is overexpressed from each of:

(i) a first genomic sequence having at least 99% sequence identity with SEQ ID NO: 1;

(ii) a second genomic sequence having at least 99% sequence identity with SEQ ID NO: 2;

(iii) a third genomic sequence having at least 99% sequence identity with SEQ ID NO: 3;

(iv) a fourth genomic sequence having at least 99% sequence identity with SEQ ID NO: 4;

(v) a fifth genomic sequence having at least 99% sequence identity with SEQ ID NO: 5; and (vi) a sixth genomic sequence having at least 99% sequence identity with SEQ ID NO: 6.

11. The method of claim 1, wherein expression of the one or more HERV-W mRNA transcripts is individually detected.

12. The method of claim 1, wherein expression of the one or more HERV-W mRNA transcripts is detected without performing hybridization on a chip.

13. A method of diagnosing and treating testicular cancer, comprising:

obtaining a testicular sample that is collected from a person suspected of suffering from testicular cancer;

assaying the testicular sample to detect whether one or more HERV-W mRNA transcripts are overexpressed; and diagnosing the person with testicular cancer when there is overexpression of the one or more HERV-W mRNA transcripts, transcripts; and treating the person with testicular cancer by performing any of orchidectomy, radiotherapy, or chemotherapy, wherein overexpression is detected when expression of the respective HERV-W mRNA transcript is increased as compared to expression of the respective HERV-W mRNA transcript in a healthy testicular sample and the one or more HERV-W mRNA transcripts have at least 99% sequence identity with any of SEQ ID NOS: 7-12.

14. The method of claim 13, comprising assaying the testicular sample to detect whether an HERV-W mRNA transcript having at least 99% sequence identity with SEQ ID NO: 7 is overexpressed.

15. The method of claim 13, comprising assaying the testicular sample to detect whether an HERV-W mRNA transcript having at least 99% sequence identity with SEQ ID NO: 8 is overexpressed.

16. The method of claim 13, comprising assaying the testicular sample to detect whether an HERV-W mRNA transcript having at least 99% sequence identity with SEQ ID NO: 9 is overexpressed.

17. The method of claim 13, comprising assaying the testicular sample to detect whether an HERV-W mRNA transcript having at least 99% sequence identity with SEQ ID NO: 10 is overexpressed.

18. The method of claim 13, comprising assaying the testicular sample to detect whether an HERV-W mRNA transcript having at least 99% sequence identity with SEQ ID NO: 11 is overexpressed.

19. The method of claim 13, comprising assaying the testicular sample to detect whether an HERV-W mRNA transcript having at least 99% sequence identity with SEQ ID NO: 12 is overexpressed.

20. The method of claim 13, comprising assaying the testicular sample to detect whether each of the following is overexpressed:

(i) a first HERV-W mRNA transcript having at least 99% sequence identity with SEQ ID NO: 7;

(ii) a second HERV-W mRNA transcript having at least 99% sequence identity with SEQ ID NO: 8;

(iii) a third HERV-W mRNA transcript having at least 99% sequence identity with SEQ ID NO: 9;

(iv) a fourth HERV-W mRNA transcript having at least 99% sequence identity with SEQ ID NO: 10;

(v) a fifth HERV-W mRNA transcript having at least 99% sequence identity with SEQ ID NO: 11; and (vi) a sixth HERV-W mRNA transcript having at least 99% sequence identity with SEQ ID NO: 12.

21. The method of claim 13, wherein the person has a hard and irregular swelling of a testicle.

22. The method of claim 13, wherein expression of the one or more HERV-W mRNA transcripts is individually detected.

23. The method of claim 13, wherein expression of the one or more HERV-W mRNA transcripts is detected without performing hybridization on a chip.

* * * * *